(12) United States Patent
Hoyer et al.

(10) Patent No.: US 11,939,292 B1
(45) Date of Patent: Mar. 26, 2024

(54) AZA-SUBSTITUTED PSILOCIN ANALOGS AND METHODS OF SYNTHESIZING THE SAME

(71) Applicant: Mydecine Innovations Group Inc., Denver, CO (US)

(72) Inventors: Denton W. Hoyer, West Haven, CT (US); Robert F. Roscow, Longmont, CO (US)

(73) Assignee: Mydecine Innovations Group Inc., Denver, CO (US)

( * ) Notice: Subject to any disclaimer, the term of this patent is extended or adjusted under 35 U.S.C. 154(b) by 0 days.

(21) Appl. No.: 18/386,021

(22) Filed: Nov. 1, 2023

Related U.S. Application Data

(63) Continuation of application No. 18/142,010, filed on May 1, 2023, which is a continuation-in-part of application No. PCT/US2022/031945, filed on Jun. 2, 2022, application No. 18/386,021 is a continuation-in-part of application No. PCT/US2021/061826, filed on Dec. 3, 2021.

(60) Provisional application No. 63/121,052, filed on Dec. 3, 2020.

(51) Int. Cl.
  *C07D 209/14* (2006.01)
  *C07D 209/12* (2006.01)
  *C07D 209/16* (2006.01)
  *C07D 471/04* (2006.01)

(52) U.S. Cl.
  CPC ......... *C07D 209/14* (2013.01); *C07D 209/12* (2013.01); *C07D 209/16* (2013.01); *C07D 471/04* (2013.01)

(58) Field of Classification Search
  CPC .................................................. C07D 209/14
  USPC ....................................................... 514/300
  See application file for complete search history.

(56) References Cited

U.S. PATENT DOCUMENTS

| 5,719,135 A | 2/1998 | Buzzetti et al. |
| 6,900,323 B2 * | 5/2005 | Wang ................... A61K 31/495 546/113 |
| 2018/0221396 A1 | 8/2018 | Chadeayne |

FOREIGN PATENT DOCUMENTS

| WO | 2014018888 A1 | 1/2014 |
| WO | 2014033597 A1 | 3/2014 |
| WO | 2020245133 A1 | 12/2020 |
| WO | 2021116503 A2 | 6/2021 |
| WO | 2021155470 A1 | 8/2021 |
| WO | 2022026223 A1 | 2/2022 |
| WO | 2022038299 A1 | 2/2022 |

OTHER PUBLICATIONS

Pubchem, Substance Record for SID 255918009, Modify Date: Aug. 25, 2017 [retrieved on Jan. 25, 2022]. Retrieved from the Internet: <URL: https://pubchem.ncbi.nlm.nih.gov/substance/255918009>. entire document.
Pubchem CID 53412486, Create date: Oct. 30, 2011 (Oct. 30, 2011), entire document, especially p. 2, compound listed.
Malaca et al., "Toxicology and Analysis of Psychoactive Tryptamines", International Journal of Molecular Scinces, Dec. 4, 2020 (Dec. 4, 2020), 21, 9279, pp. 1-30, entire document, especially p. 1, abstract, para 1; p. 2, para 5; Table 1; Figure 1.
Giorgetti et al.. "Detection and phase I metabolism of the 7?azaindole-der!ved synthetic cannabinold 5F-AB-P7 AICA including a preliminary pharmacokinelic evaluation", Drug Testing and Analysis, Sep. 2, 2019 (Sep. 2, 2019), 12, pp. 78-91, entire document, especially p. 78, abstract; Figures 1, 4.
ZINC44713096, Create date: Jul. 21, 2010 (Jul. 21, 2010), entire document, especially p. 1.
International Search Report and Written Opinion in PCT/US21/61826 dated Apr. 11, 2022, 11 pages.
International Search Report and Written Opinion in PCT/US22/31945 dated Nov. 7, 2022, 80 pages.

* cited by examiner

*Primary Examiner* — Niloofar Rahmani
(74) *Attorney, Agent, or Firm* — Berg Hill Greenleaf Ruscitti LLP

(57) ABSTRACT

The present invention is directed to novel chemical compositions of matter and their methods of synthesis, and in particular novel analogs of Psilocin having enhanced physical and pharmacokinetic characteristics.

6 Claims, 11 Drawing Sheets

AZA-SUBSTITUTED PSILOCIN ANALOGS AND METHODS OF SYNTHESIZING THE SAME

CROSS-REFERENCE TO RELATED APPLICATION

This application is a continuation of U.S. application Ser. No. 18/142,010 filed May 1, 2023; which is a bypass continuation-in-part of PCT Application No. PCT/US21/61826 having an international filing date of Dec. 3, 2021, which designated the United States, the specification, figures and claims of which are incorporated by reference in their entirety.#

TECHNICAL FIELD

The present invention is directed to novel chemical compositions of matter, and in particular novel aza-substituted analogs of Psilocin having enhanced physical and pharmacokinetic characteristics.

BACKGROUND

The natural product Psilocybin exists as a prodrug form of the psychoactive molecule Psilocin. This raises the question of why evolution would invest an organism's energy to prepare this prodrug. It has been speculated that this may be due to the oxidative instability of the parent Psilocin. As generally outlined in FIG. 1, bruising of many mushrooms containing Psilocybin results in the formation of a bluish dye which has recently been tied to a series of transformations with molecular oxygen and in-situ enzymes or trace transition metals to form a blue inactive polymer. It is therefore likely the prodrug serves as an air stable form which is rapidly converted to active Psilocin in the gut of an animal by the action of alkaline phosphatase. This instability to oxygen or oxidative enzymes may in like manner limit the pharmaceutical efficacy and reliability of Psilocin formulations, particularly in solutions for administration. The inventions described in this document address this instability with new analogs that may exhibit enhanced resistance to oxidation. Further, these improved analogs may show modified pharmacokinetics, stability, delivery, and bioavailability, and metabolism due to differences in glucuronidation and/or demethylation of the dimethyl amine functionality among other considerations outlined below.

SUMMARY OF THE INVENTION

In one aspect, the present invention includes novel prodrug modifications to psilocin, generally referred to as a compound(s) of the invention. In one preferred aspect, the novel prodrug modifications to psilocin may include modifications configured to allow for the compounds of the invention to retain a serotonin 5-HT receptor subtype selectivity profile similar to psilocin. In another preferred aspect, the invention includes novel modifications to psilocin that may exhibit increased oxidative stability. In another preferred aspect, the invention includes novel modifications to psilocin that may exhibit increased ability to be efficiently delivered through a transdermal and/or transmucosal route to a subject in need thereof.

In another preferred aspect, the invention includes novel modifications to psilocin including one or more "aza" substitutions to the Azaindole group and/or one or more aza substitutions to psilocin a forming an imidazopyridine analog. In another aspect, the present invention includes novel pyrrolopyridines and imidazopyridine analogs of Psilocin, which may be formed by a "nitrogen switch" modification to psilocin, wherein a carbon, forming part of the indole alkaloid ring of Psilocin may be replaced with a nitrogen.

In another, the present invention includes novel psilocin analog having a novel O-linked acyl group modification, which may, or may not be coupled with one or more "aza" substitutions to the Azaindole group and/or one or more aza substitutions to psilocin a forming an imidazopyridine analog. In another aspect, the present invention includes novel pyrrolopyridine analogs of Psilocin having an O-acyl group modification.

In another aspect, the present invention includes novel imidazopyridine analog of Psilocin having an O-acyl group modification. In one embodiment a novel O-linked acyl group modification may include O-linked esters of linear saturated or mono- and di-unsaturated acids, and preferably naturally occurring saturated or mono- and di-unsaturated acids. In a preferred embodiment, an O-linked esters of linear saturated or linear mono-, di- or polyunsaturated acids may include a $C_1$-$C_{18}$, or preferably a $C_7$-$C_{13}$ linear saturated or linear mono-, di- or polyunsaturated acids. Additional embodiments may include additional modification, include modified amine groups, as well as alkanes, and preferably linear alkanes bound to an amine group, such as diisopropylamine.

In additional aspects, any of the foregoing may be optionally substituted, or a prodrug, therapeutically active metabolite, hydrate, solvate, or pharmaceutically acceptable salt thereof.

In additional aspects, any of the foregoing may be optionally substituted, or a prodrug, therapeutically active metabolite, hydrate, solvate, or pharmaceutically acceptable salt thereof.

Another aspect of the invention may include an aza substituted psilocin analog compound according to Formula XV:

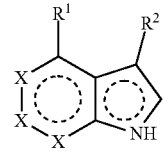

Formula (XVI)

wherein X is independently N, or CH, and wherein at least one X is N; $R^1$ is O, or —OH, $R^2$ is an amine, or a linear alkane-$R^3$, wherein $R^3$ is $(CH_3)_2NH$ (dimethylamine), or $CH_3CH(CH_3)NHCH(CH_3)CH_3$ (diisopropylamine); and wherein said dashed lines represents possible double bond positions according to the configuration of X being N, and $R^1$ being O or —OH. In additional aspects, any of the foregoing may be optionally substituted, or a prodrug, therapeutically active metabolite, hydrate, solvate, or pharmaceutically acceptable salt thereof.

Another aspect of the invention may include an aza substituted psilocin analog compound according to Formula XV:

Formula (XVI)

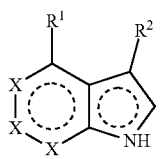

wherein X is independently N, or CH, and wherein at least one X is N; $R^1$ is H, O, —OH, —OP(O)(OH)$_2$, a protecting group, an O-linked acyl, said acyl having a general formula of R'—C(=O)-D, wherein R' is optionally an O, and wherein D is an alkane; $R^2$ is an amine, or a linear alkane-$R^3$, wherein $R^3$ is (CH3)2NH (dimethylamine), or CH$_3$CH(CH3)NHCH(CH3)CH3 (diisopropylamine); and wherein said dashed lined represents possible double bond positions according to the configuration of X and $R^1$. In additional aspects, any of the foregoing may be optionally substituted, or a prodrug, therapeutically active metabolite, hydrate, solvate, or pharmaceutically acceptable salt thereof. Exemplary saturated ester or an unsaturated acid ester may include, but not be limited to those identified in Tables 1 and 2 below.

Another aspect of the invention may include a psilocin analog compound according to Formula XVI:

Formula (XVI)

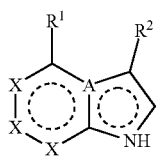

wherein X is independently N, or CH; A is N, or C, however where A is N, X, is CH, and wherein said dashed lines represents possible double bond positions according to the configuration of A, or X being N or CH and $R^1$; $R^1$ is O, or —OH; $R^2$ is an amine, or a linear alkane-$R^3$, wherein $R^3$ is (CH3)2NH (dimethylamine), or CH$_3$CH(CH3)NHCH(CH3)CH3 (diisopropylamine). In additional aspects, any of the foregoing may be optionally substituted, or a prodrug, therapeutically active metabolite, hydrate, solvate, or pharmaceutically acceptable salt thereof.

Another aspect of the invention may include a psilocin analog compound according to Formula XVI:

Formula (XVI)

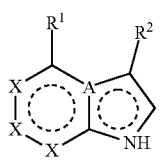

wherein X is independently N, or CH; A is N, or C, however where A is N, X, is CH, and wherein said dashed lines represents possible double bond positions according to the configuration of A, X, or $R^1$; $R^1$ is H, O, —OH, —OP(O)(OH)$_2$, a protecting group, an O-linked acyl, said acyl having a general formula of R'—C(=O)-D, wherein R' is optionally an O, and wherein D is an alkane; $R^2$ is an amine, or a linear alkane-$R^3$, wherein $R^3$ is (CH$_3$)$_2$NH (dimethyl-amine), or CH$_3$CH(CH3)NHCH(CH3)CH3 (diisopropylamine). In additional aspects, any of the foregoing may be optionally substituted, or a prodrug, therapeutically active metabolite, hydrate, solvate, or pharmaceutically acceptable salt thereof. Exemplary saturated ester or an unsaturated acid ester may include, but not be limited to those identified in Tables 1 and 2 below.

Another aspect of the invention may include a psilocin analog compound according to Formula XVII, also referred to herein:

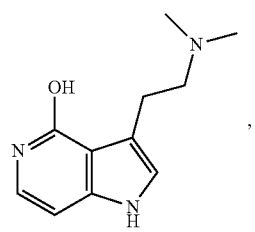

or a prodrug, therapeutically active metabolite, hydrate, solvate, or pharmaceutically acceptable salt thereof.

Another aspect of the invention may include a psilocin analog compound according to Formula XVII, also referred to herein as MY205B:

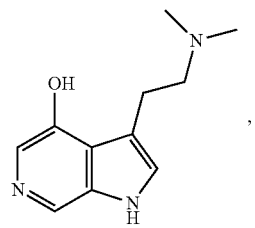

or a prodrug, therapeutically active metabolite, hydrate, solvate, or pharmaceutically acceptable salt thereof.

Another aspect of the invention may include a psilocin analog compound according to Formula XIX, also referred to herein as MY205C:

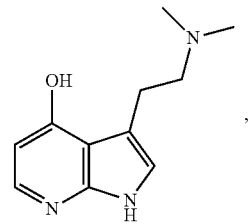

or a prodrug, therapeutically active metabolite, hydrate, solvate, or pharmaceutically acceptable salt thereof.

Another aspect of the invention may include a psilocin analog compound according to Formula XX, also referred to herein as MY205DT:

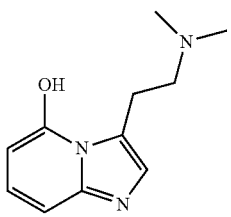

or a prodrug, therapeutically active metabolite, hydrate, solvate, or pharmaceutically acceptable salt thereof.

Another aspect of the invention may include a psilocin analog compound according to Formula XXI, also referred to herein as MY331A:

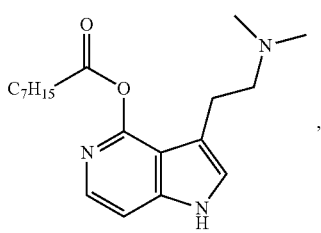

or a prodrug, therapeutically active metabolite, hydrate, solvate, or pharmaceutically acceptable salt thereof.

Another aspect of the invention may include a psilocin analog compound according to Formula XXII, also referred to herein as MY331B:

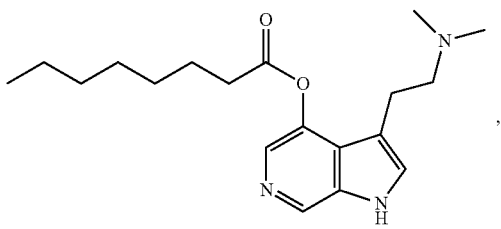 [SMILES: CCCCCCCC(=O)Oc1cncc2[nH]cc(CCN(C)C)c12]

or a prodrug, therapeutically active metabolite, hydrate, solvate, or pharmaceutically acceptable salt thereof.

Another aspect of the invention may include a psilocin analog compound according to Formula XXIII, also referred to herein as MY333B:

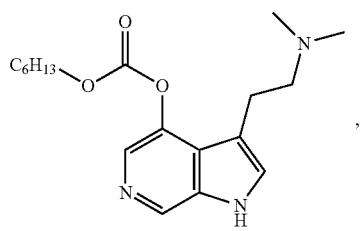

or a prodrug, therapeutically active metabolite, hydrate, solvate, or pharmaceutically acceptable salt thereof.

Another aspect of the invention may include an aza substituted psilocin analog according to Formula XIII:

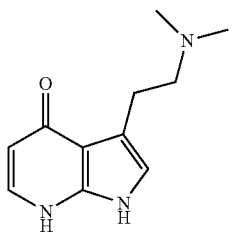

(Formula XIII)

In another aspect, the present invention includes methods of synthesizing novel analogs of Psilocin identified herein as the compound according to Formulas I-XXIII, or a pharmaceutically acceptable salt, solvate, stereoisomer, tautomer, or prodrug thereof as described herein.

In another aspect, the present invention includes novel analogs of Psilocin identified herein as the compound according to Formulas I-XXIII, or a pharmaceutically acceptable salt, solvate, stereoisomer, tautomer, or prodrug thereof as described herein. Additional aspects of the current invention include a compound of Formula I-XXIII, or a pharmaceutically acceptable salt, solvate, stereoisomer, tautomer, or prodrug thereof, for use in recreational, phycological, or medical therapies.

Additional aspects of the present invention provides a systems, methods, and compositions for novel psilocin analogs according to the compounds of Formula I-XVI, (also referred to as a/the compound(s) or composition(s) of the invention), and a pharmaceutically acceptable carrier or diluent, which may preferably further include a method of treatment of the human or animal body using one or more of the novel compounds, or pharmaceutical compositions described herein.

Additional aspects of the present invention provide a method for treating a disease or condition for which modulation of serotonin receptor activity is beneficial comprising: administering to a subject in need thereof, a therapeutically effective amount of a one or more compounds of the invention, or a pharmaceutically acceptable composition, also generally referred to as a pharmaceutical composition or a pharmaceutical composition of the invention containing a therapeutically effective amount of a one or more compounds of the invention and a pharmaceutically carrier.

In another aspect, the present invention include novel prodrug modifications to psilocin configured to facilitate transdermal delivery of the compound.

Additional aspects of the invention may become evident based on the specification and figures presented below.

DETAILED DESCRIPTION OF THE INVENTION

Figure 1:
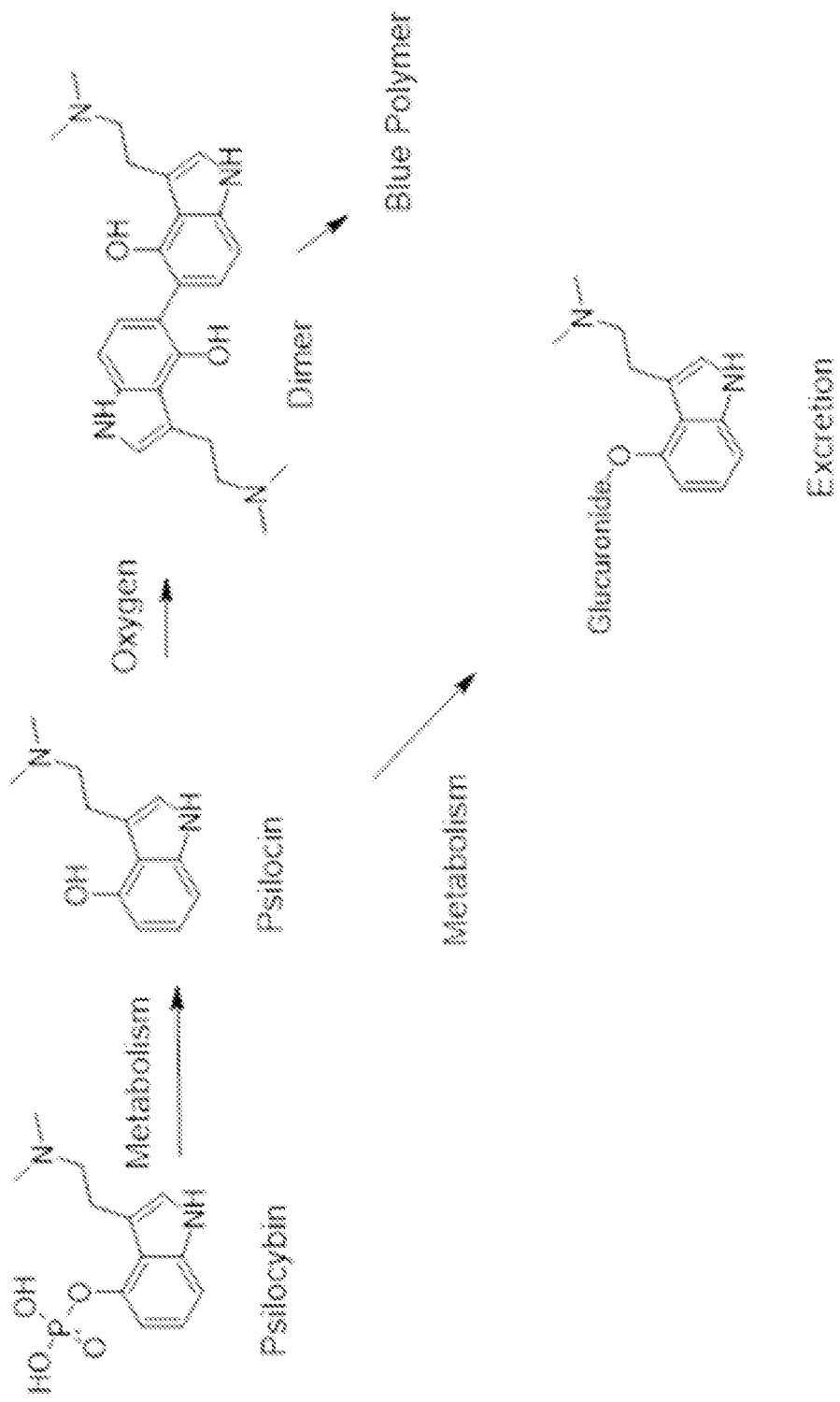
FIG. 1: shows the in vivo oxidative and metabolic pathway of psilocybin.
Figure 2:
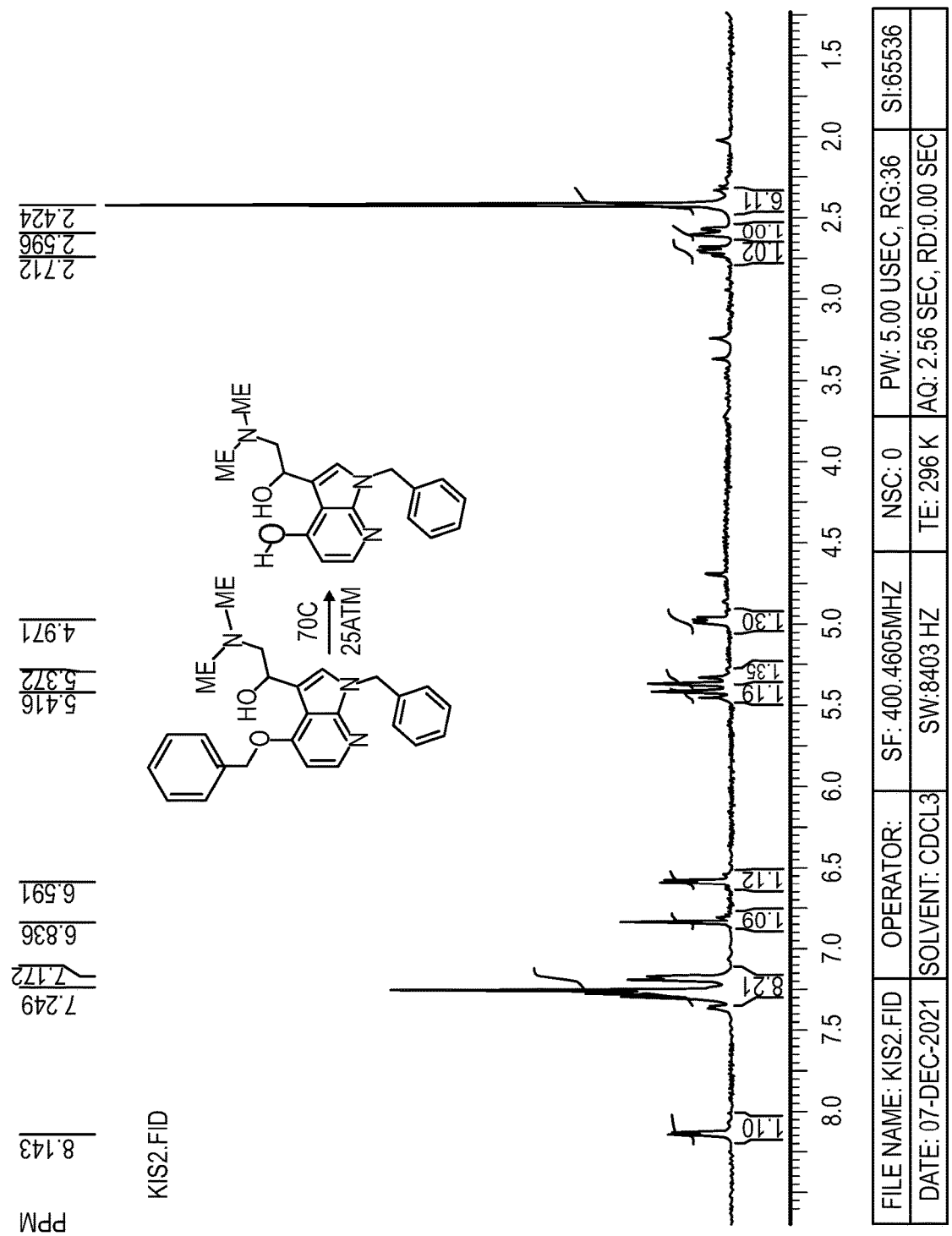
FIG. 2: shows confirmation of synthesis of ava substituted psilocin intermediates in one embodiment thereof.
Figure 3:
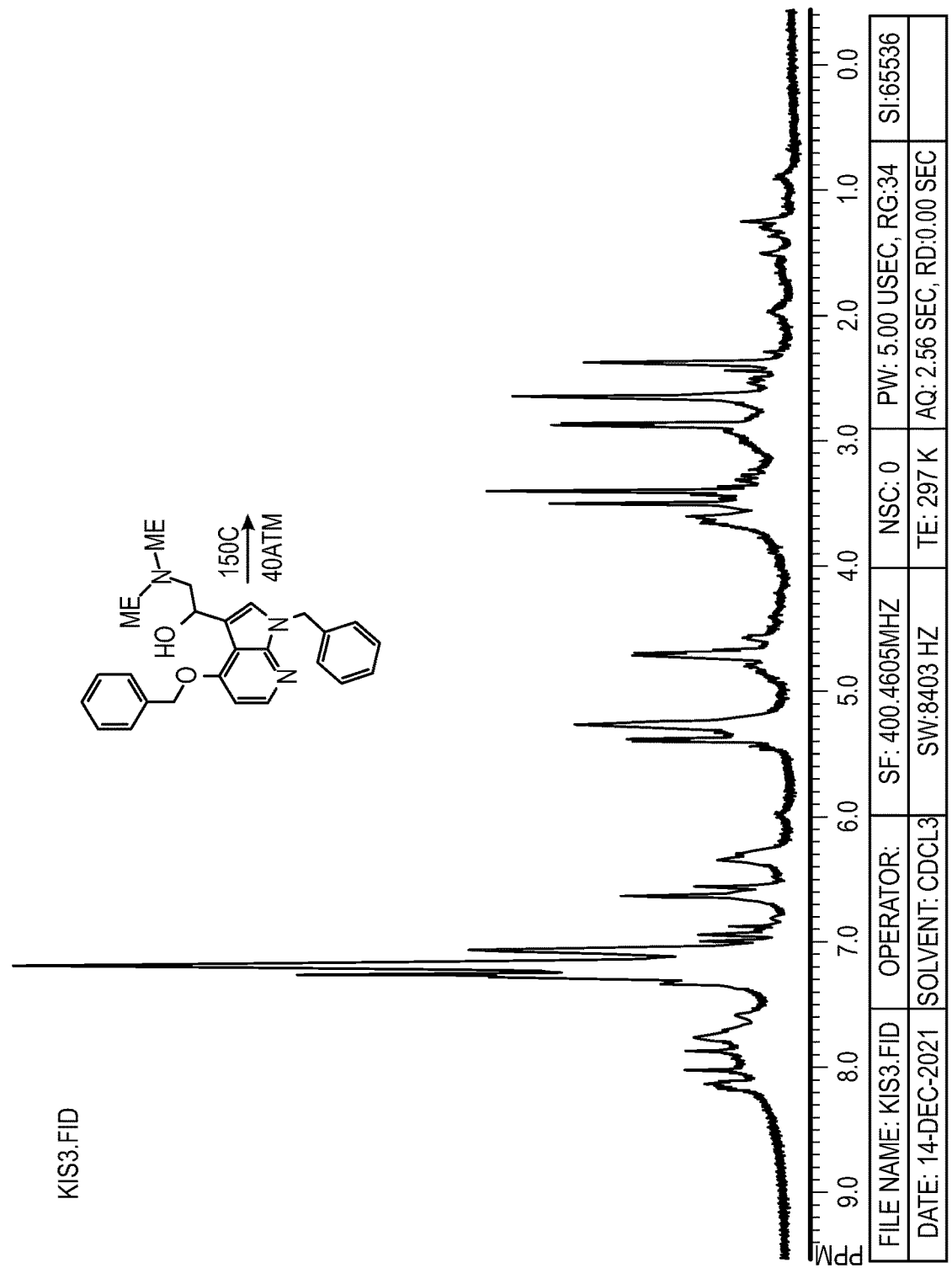
FIG. 3: shows confirmation of synthesis of ava substituted psilocin intermediates in one embodiment thereof.
Figure 4:
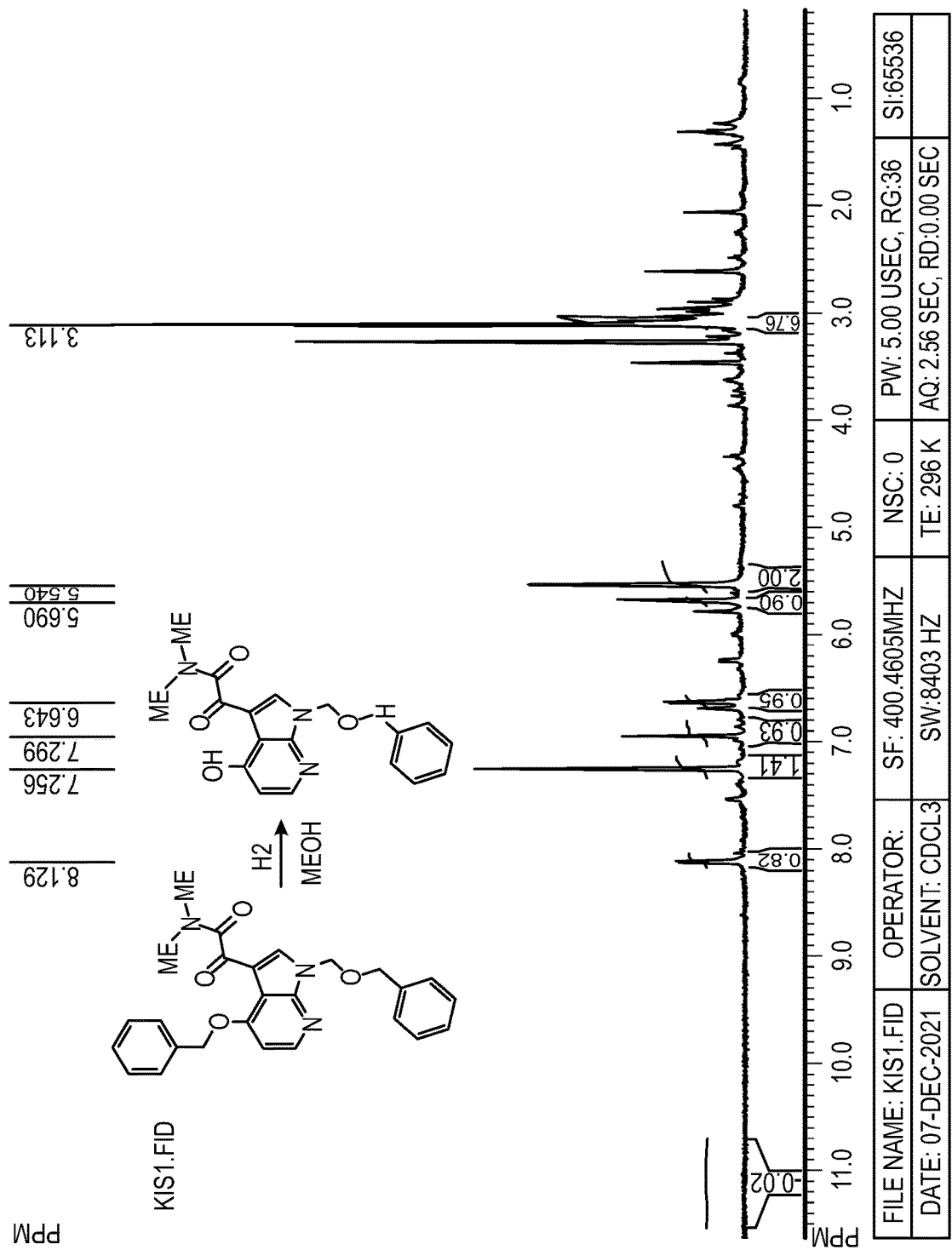
FIG. 4: shows confirmation of synthesis of ava substituted psilocin intermediates in one embodiment thereof.
Figure 5:
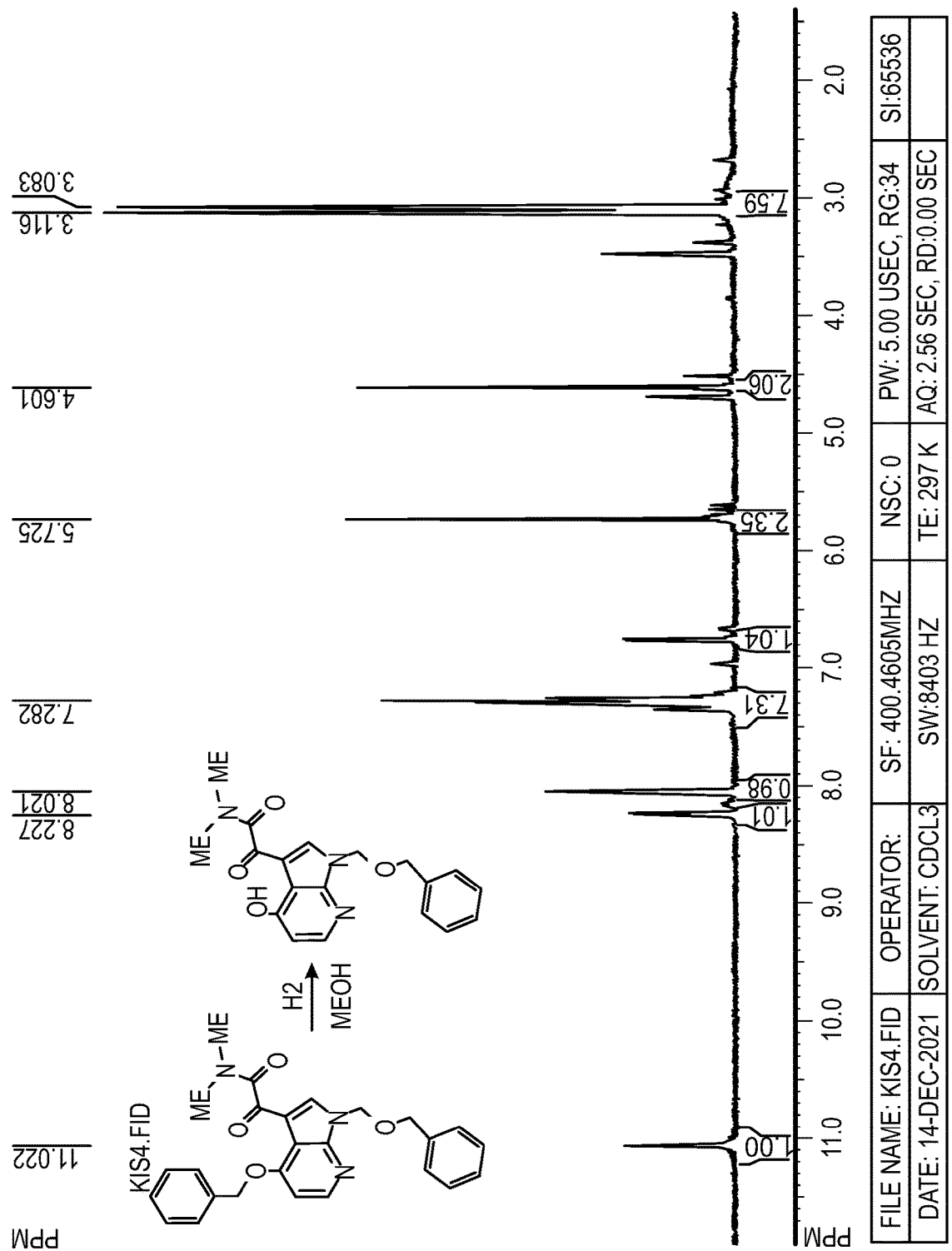
FIG. 5: shows confirmation of synthesis of ava substituted psilocin intermediates in one embodiment thereof.
Figure 6:
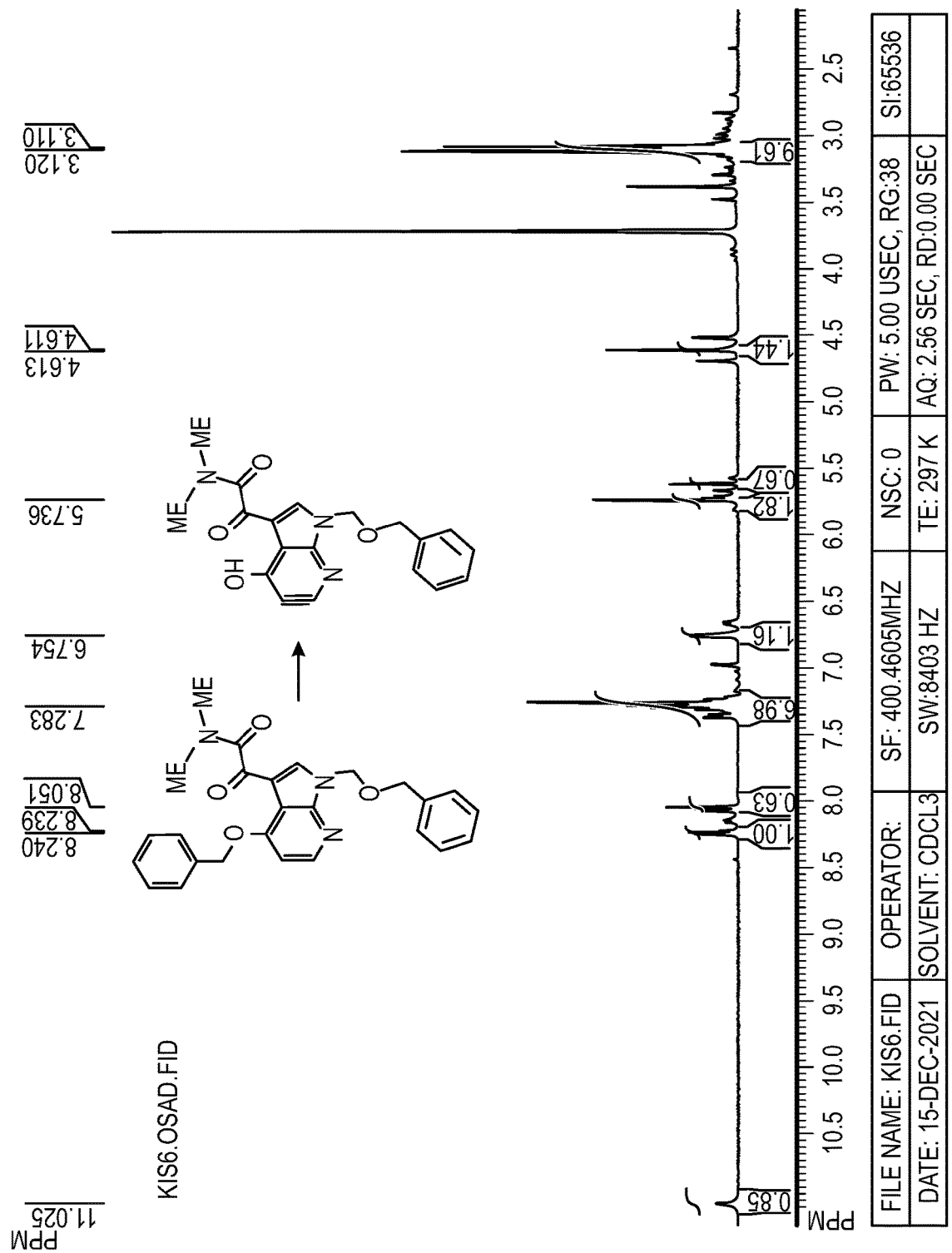
FIG. 6: shows confirmation of synthesis of ava substituted psilocin intermediates in one embodiment thereof.
Figure 7:
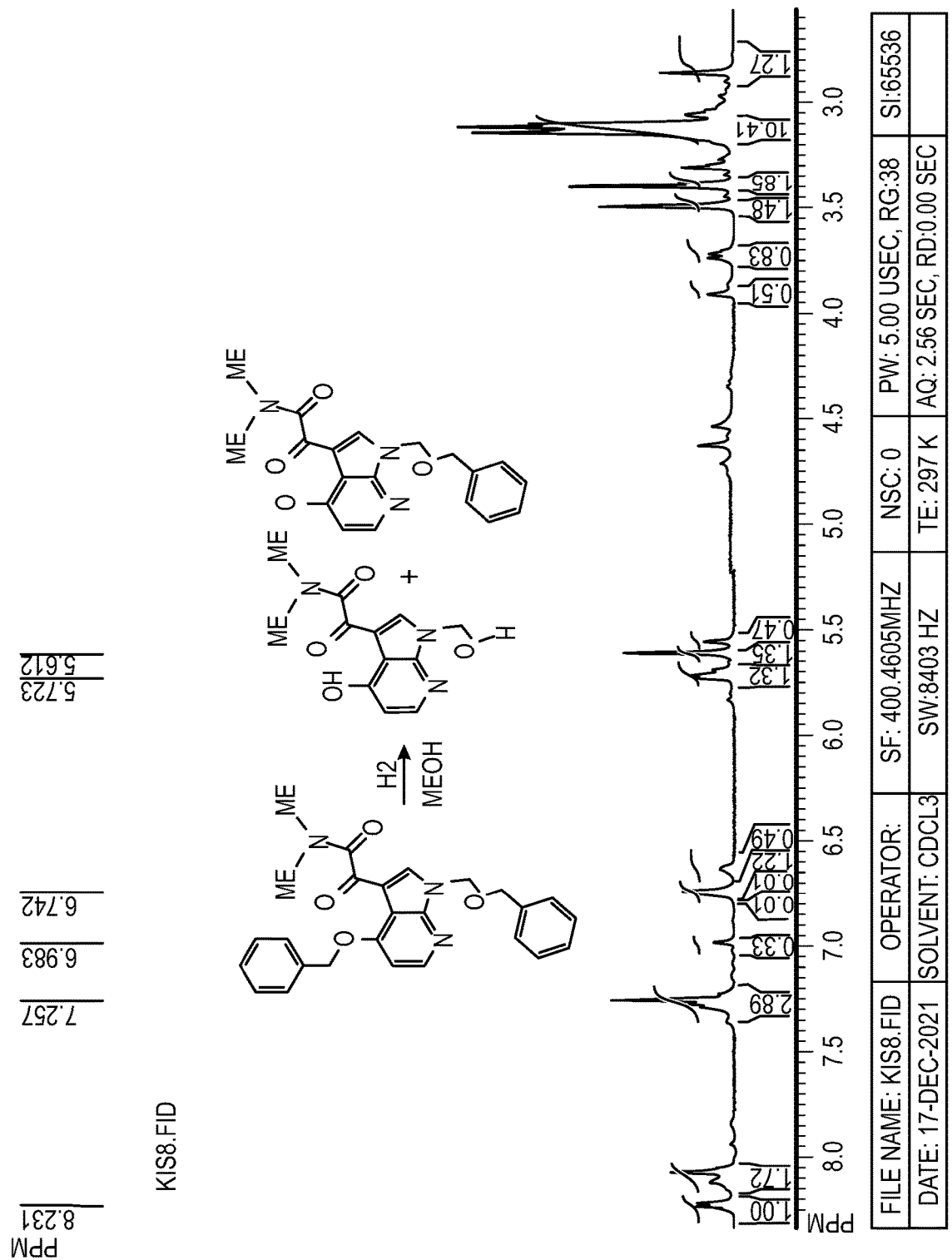
FIG. 7: shows confirmation of synthesis of ava substituted psilocin intermediates in one embodiment thereof.
Figure 8:
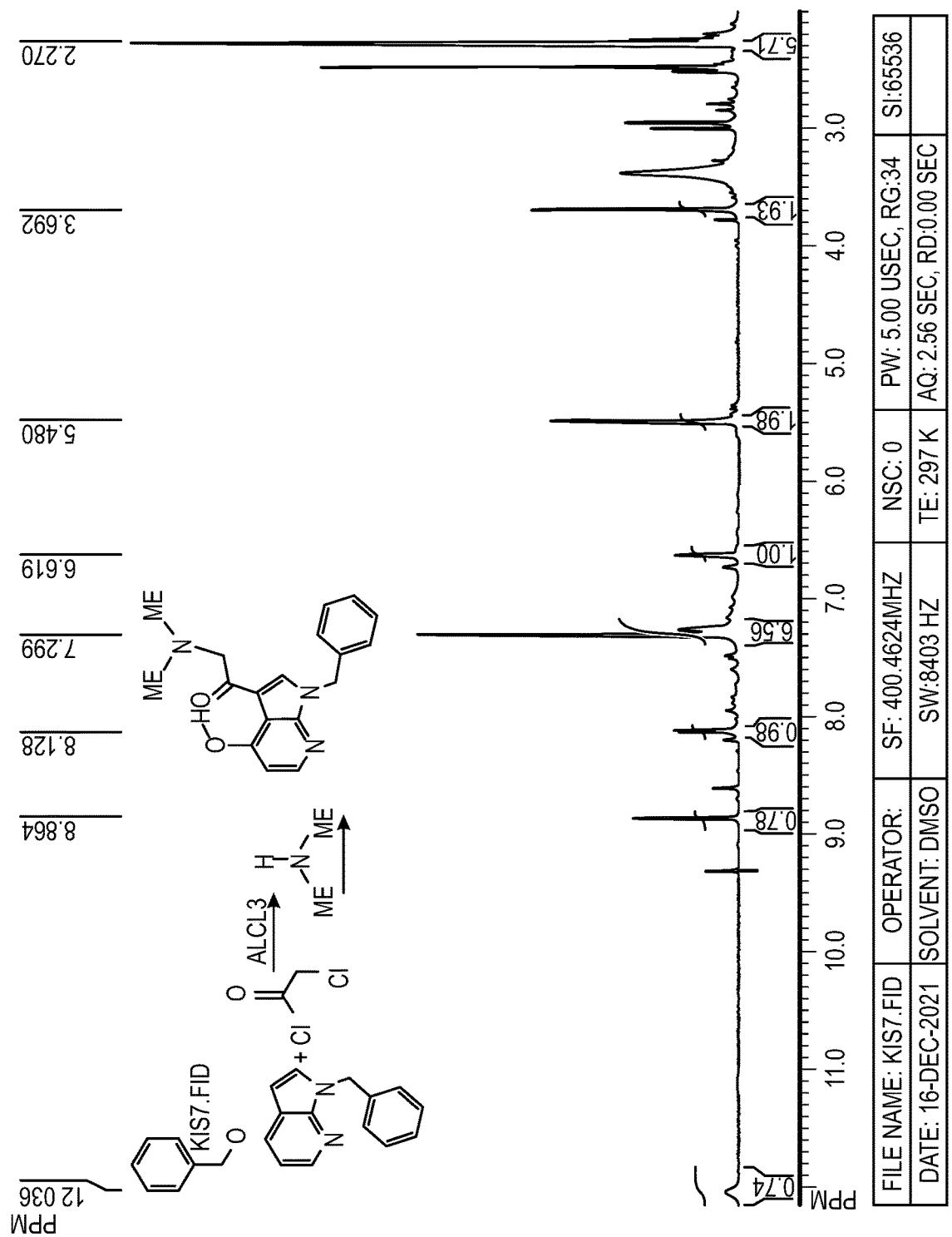
FIG. 8: shows confirmation of synthesis of ava substituted psilocin intermediates in one embodiment thereof.
Figure 9A:
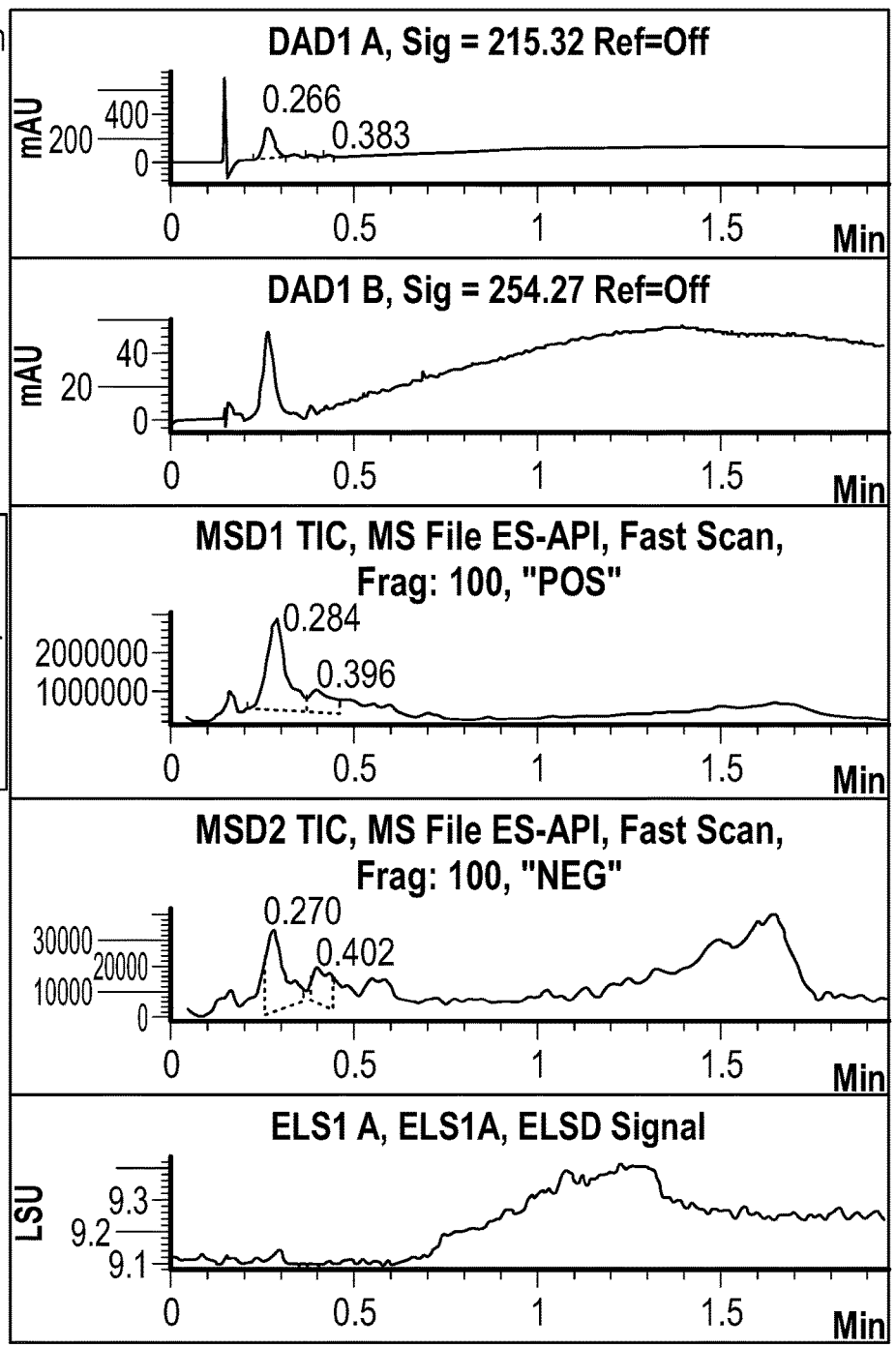
FIGS. 9A-C: shows confirmation of synthesis of ava substituted psilocin intermediates in one embodiment thereof.
Figure 9B:
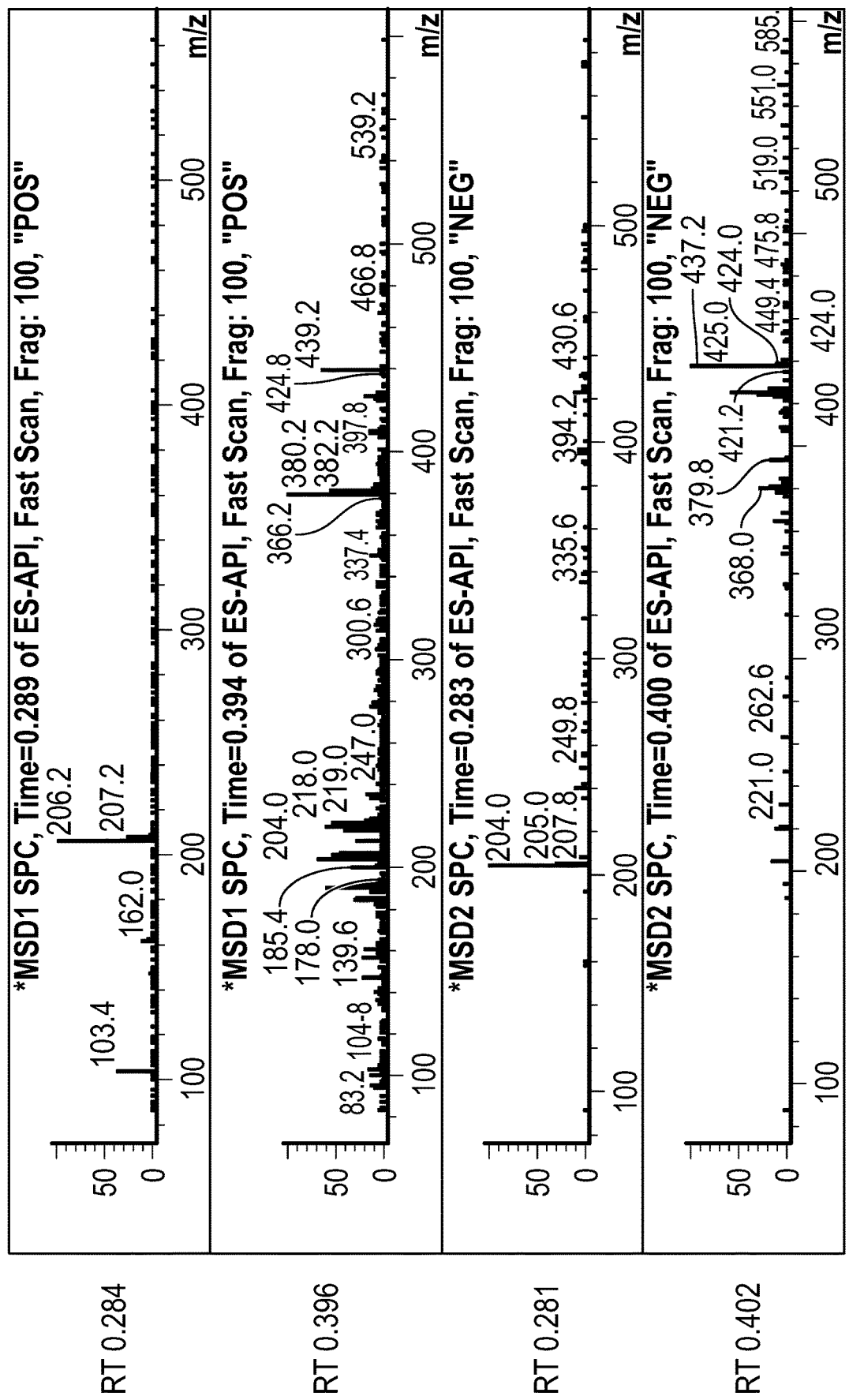
Figure 9C:
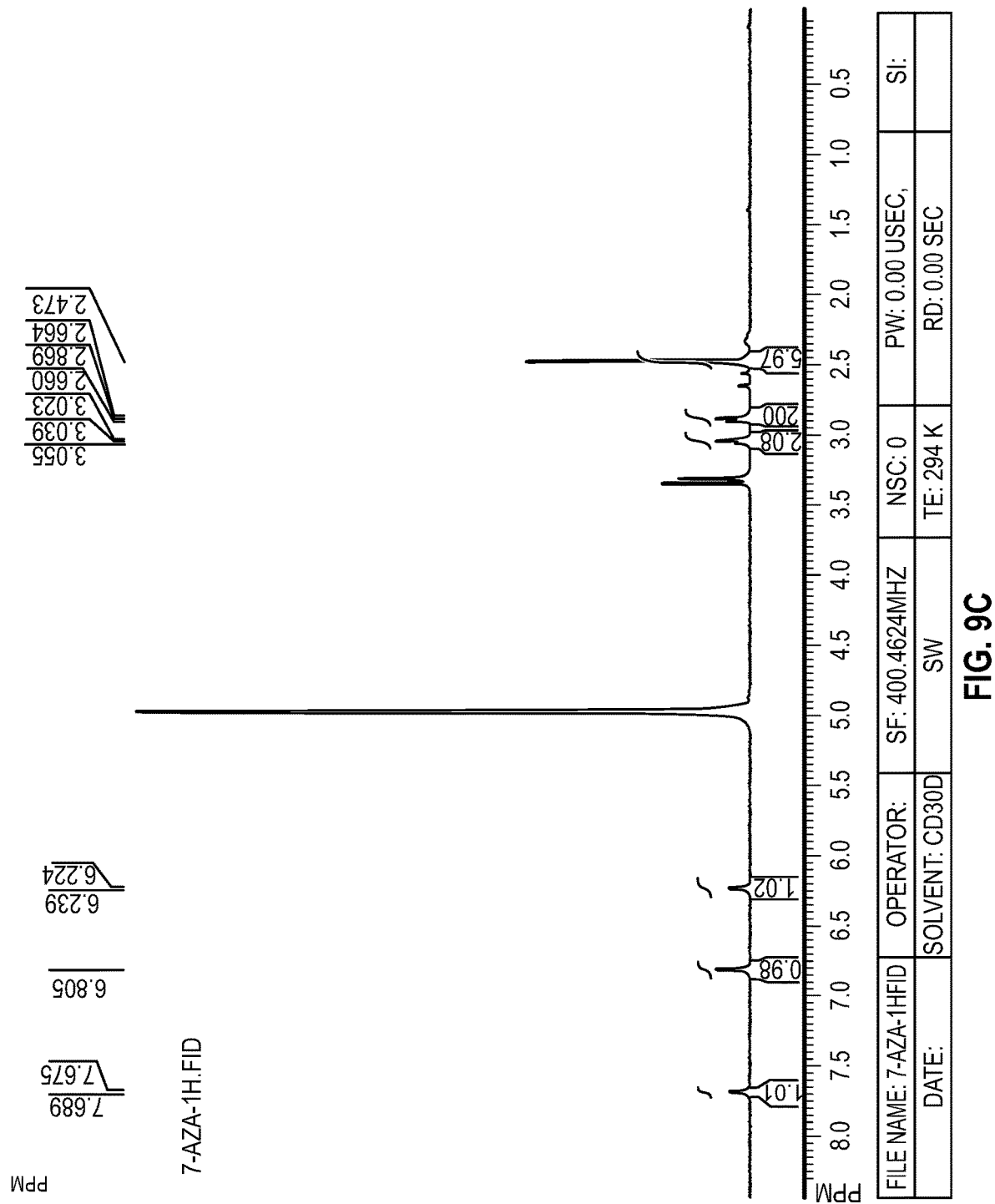

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The invention includes novel modifications to psilocin that in certain embodiments exhibit increased oxidative stability. In another preferred embodiment, the invention includes novel modifications to psilocin that may exhibit increased ability to be efficiently delivered through a transdermal and/or transmucosal route to a subject in need thereof.

On one embodiment, the invention include one or more novel Psilocin analogs having increased resistance to oxidation in the presence of by molecular oxygen, among other novel pharmacokinetic properties. As shown above, the compounds of Formulas I-IV and XIII-XV describe novel analogs of Psilocin containing one or more N or aza substitutions to their Azaindole groups, and in the case of the compound of Formula V and XVII forming and imidazopyridine structure. The carbon to nitrogen replacement in the Psilocin analog may increase oxidation potential such that the degradation by oxygen is inhibited. This can be measured by calculating of the HOMO energies of the analog compounds of the invention compared to the parent Psilocin and more specifically by an "average local ionization energy" analysis. The more aza substitutions in the Psilocin analogs may also affect the degree to which glucuronidation occur, which is a major metabolic route of elimination from the body. For example, the analog compounds of the invention according to Formulas I-VI and XIII-XV (5-Aza) and Formulas V and XVI (imidazopyridine) in particular, are predicted to show reduced glucuronidation and therefore slowed excretion. Notably, the analog compounds of the invention may further provide prodrug formulations to enhance oxidative stability.

In another preferred embodiment, the invention includes novel modifications to psilocin glucuronides that may exhibit increased water-solubility and/or bioavailability. In another preferred embodiment, the invention includes novel modifications to psilocin including one or more aza substitutions to the Azaindole group and/or one or more aza substitutions to psilocin a forming an imidazopyridine analog. In another embodiment, the present invention includes novel pyrrolopyridines and/or imidazopyridine analogs of Psilocin, which may be formed by a "nitrogen switch" modification to psilocin, wherein a carbon, forming part of the indole alkaloid ring of Psilocin may be replaced with a nitrogen.

Another embodiment of the invention may include an aza substituted psilocin analog compound selected from the group consisting of:

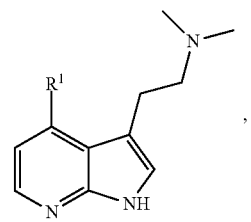
(Formula I)

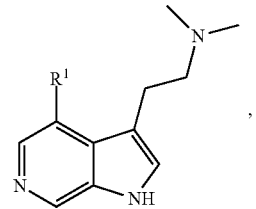
(Formula II)

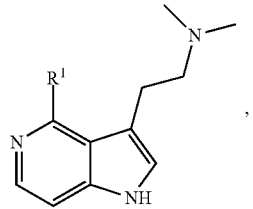
(Formula III)

wherein $R^1$ is —OH, or O.

Another embodiment of the invention may include a compound according to (Formula IV)

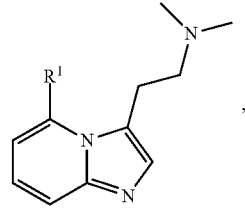
(Formula IV)

wherein $R^1$ is —OH.

Another embodiment of the invention may include an aza substituted psilocin analog according to Formula XIII:

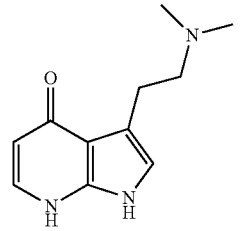
(Formula XIII)

In additional embodiments, any of the foregoing may be optionally substituted, or a prodrug, therapeutically active metabolite, hydrate, solvate, or pharmaceutically acceptable salt thereof.

In additional embodiments, any of the foregoing may be optionally substituted, or a prodrug, therapeutically active metabolite, hydrate, solvate, or pharmaceutically acceptable salt thereof.

Another embodiment of the invention may include an aza substituted psilocin analog compound according to Formula XV:

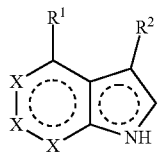

Formula (XVI)

wherein X is independently N, or CH, and wherein at least one X is N; $R^1$ is O, or —OH, $R^2$ is an amine, or a linear alkane-$R^3$, wherein $R^3$ is (CH3)2NH (dimethylamine), or $CH_3CH(CH3)NHCH(CH3)CH3$ (diisopropylamine); and wherein said dashed lines represents possible double bond positions according to the configuration of X being N, and $R^1$ being O or —OH. In additional aspects, any of the foregoing may be optionally substituted, or a prodrug, therapeutically active metabolite, hydrate, solvate, or pharmaceutically acceptable salt thereof.

Another embodiment of the invention may include an aza substituted psilocin analog compound according to Formula XVI:

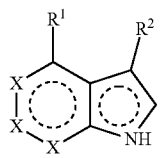

Formula (XVI)

wherein X is independently N, or CH, and wherein at least one X is N; $R^1$ is H, O, —OH, —OP(O)(OH)$_2$, a protecting group, an O-linked acyl, said acyl having a general formula of R'—C(=O)-D, wherein R' is optionally an O, and wherein D is an alkane; $R^2$ is an amine, or a linear alkane-$R^3$, wherein $R^3$ is (CH3)2NH (dimethylamine), or $CH_3CH(CH3)NHCH(CH3)CH3$ (diisopropylamine); and wherein said dashed lined represents possible double bond positions according to the configuration of X and $R^1$. In additional aspects, any of the foregoing may be optionally substituted, or a prodrug, therapeutically active metabolite, hydrate, solvate, or pharmaceutically acceptable salt thereof. In additional embodiments, any of the foregoing may be optionally substituted, or a prodrug, therapeutically active metabolite, hydrate, solvate, or pharmaceutically acceptable salt thereof.

In certain other embodiments, D is a $C_1$-$C_{18}$ linear saturated alkane, or a $C_1$-$C_{18}$ linear unsaturated alkane. In another embodiment, a saturated linear alkane of the compound of Formula XV includes a saturated linear ester selected from the group consisting of:

HCO$_2$, H$_3$CCO$_2$, H$_3$C(CH$_2$)CO$_2$, H$_3$C(CH$_2$)$_2$CO$_2$, H$_3$C(CH$_2$)$_3$CO$_2$, H$_3$C(CH$_2$)$_4$CO$_2$,

H$_3$C(CH$_2$)$_5$CO$_2$, H$_3$C(CH$_2$)$_6$CO$_2$, H$_3$C(CH$_2$)$_7$CO$_2$, H$_3$C(CH$_2$)$_8$CO$_2$,

H$_3$C(CH$_2$)$_9$CO$_2$, H$_3$C(CH$_2$)$_{10}$CO$_2$, H$_3$C(CH$_2$)$_{11}$CO$_2$, H$_3$C(CH$_2$)$_{12}$CO$_2$,

H$_3$C(CH$_2$)$_{13}$CO$_2$, H$_3$C(CH$_2$)$_{14}$CO$_2$, H$_3$C(CH$_2$)$_{15}$CO$_2$, and H$_3$C(CH$_2$)$_{16}$CO$_2$ and wherein any of the foregoing may be optionally substituted.

In another preferred embodiment, a linear unsaturated acid ester of the linear ester of the compound of Formula XV includes a mono- or poly-unsaturated linear fatty acid ester selected from the group consisting of:

CH$_3$(CH$_2$)CH=CH(CH$_2$)$_7$CO$_2$,
CH$_3$(CH$_2$)$_3$CH=CH(CH$_2$)$_7$CO$_2$,
CH$_3$(CH$_2$)$_5$CH=CH(CH$_2$)$_7$CO$_2$,
CH$_3$CH$_2$CH=CHCH$_2$CH=CHCH$_2$CH=CH(CH$_2$)$_7$CO$_2$,
CH$_3$(CH$_2$)$_4$CH=CHCH$_2$CH=CH(CH$_2$)$_7$CO$_2$,
CH$_3$CH$_2$CH=CHCH$_2$CH=CHCH$_2$CH=CHCH$_2$CH=CH(CH$_2$)$_4$CO$_2$,
CH$_3$(CH$_2$)$_6$CH=CH(CH$_2$)$_7$COO, CH$_3$(CH$_2$)$_4$CH=CHCH$_2$CH=CH(CH$_2$)$_7$CO$_2$, and wherein any of the foregoing may be optionally substituted.

In further embodiments, $R^1$ of the compound of Formula XV can be selected from the group consisting of:

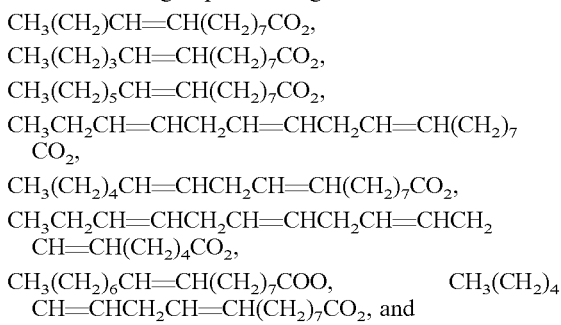

and

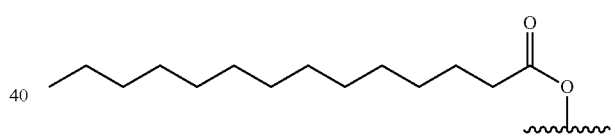

In further embodiments, $R^2$ of Formula XV can be selected from the group consisting of:

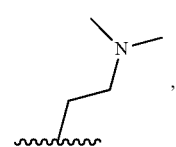 [SMILES: *CCN(C)C]

and

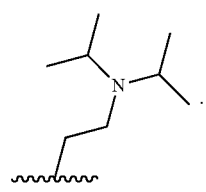 [SMILES: *CCN(C(C)C)C(C)C]

Another aspect of the invention may include a psilocin analog compound according to Formula XVI:

Formula (XVI)

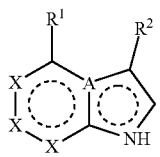

wherein X is independently N, or CH; A is N, or C, however where A is N, X, is CH, and wherein said dashed lines represents possible double bond positions according to the configuration of A, or X being N or CH and $R^1$; $R^1$ is O, or —OH; $R^2$ is an amine, or a linear alkane-$R^3$, wherein $R^3$ is (CH3)2NH (dimethylamine), or CH3CH(CH3)NHCH(CH3)CH3 (diisopropylamine). In additional aspects, any of the foregoing may be optionally substituted, or a prodrug, therapeutically active metabolite, hydrate, solvate, or pharmaceutically acceptable salt thereof.

Another aspect of the invention may include a psilocin analog compound according to Formula XVI:

Formula (XVI)

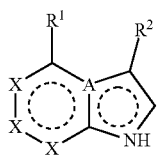

wherein X is independently N, or CH; A is N, or C, however where A is N, X, is CH, and wherein said dashed lines represents possible double bond positions according to the configuration of A, X, or $R^1$; $R^1$ is H, I, —OH, —OP(O)(OH)$_2$, a protecting group, an O-linked acyl, said acyl having a general formula of R'—C(=O)-D, wherein R' is optionally an O, and wherein D is an alkane; $R^2$ is an amine, or a linear alkane-$R^3$, wherein $R^3$ is (CH3)2NH (dimethylamine), or CH3CH(CH3)NHCH(CH3)CH3 (diisopropylamine). In additional aspects, any of the foregoing may be optionally substituted, or a prodrug, therapeutically active metabolite, hydrate, solvate, or pharmaceutically acceptable salt thereof.

In certain other embodiments, D is a $C_1$-$C_{18}$ linear saturated alkane, or a $C_1$-$C_{18}$ linear unsaturated alkane. In another embodiment, a saturated linear alkane of the compound of Formula XVI includes a saturated linear ester selected from the group consisting of:
HCO$_2$, H$_3$CCO$_2$, H$_3$C(CH$_2$)CO$_2$, H$_3$C(CH$_2$)$_2$CO$_2$, H$_3$C(CH$_2$)$_3$CO$_2$, H$_3$C(CH$_2$)$_4$CO$_2$,
H$_3$C(CH$_2$)$_5$CO$_2$, H$_3$C(CH$_2$)$_6$CO$_2$, H$_3$C(CH$_2$)$_7$CO$_2$, H$_3$C(CH$_2$)$_8$CO$_2$,
H$_3$C(CH$_2$)$_9$CO$_2$, H$_3$C(CH$_2$)$_{10}$CO$_2$, H$_3$C(CH$_2$)$_{11}$CO$_2$, H$_3$C(CH$_2$)$_{12}$CO$_2$,
H$_3$C(CH$_2$)$_{13}$CO$_2$, H$_3$C(CH$_2$)$_{14}$CO$_2$, H$_3$C(CH$_2$)$_{15}$CO$_2$, and H$_3$C(CH$_2$)$_{16}$CO$_2$ and wherein any of the foregoing may be optionally substituted.

In another preferred embodiment, a linear unsaturated acid ester of the linear ester of the compound of Formula XVI includes a mono- or poly-unsaturated linear fatty acid ester selected from the group consisting of:
CH$_3$(CH$_2$)CH=CH(CH$_2$)$_7$CO$_2$,
CH$_3$(CH$_2$)$_3$CH=CH(CH$_2$)$_7$CO$_2$,
CH$_3$(CH$_2$)$_5$CH=CH(CH$_2$)$_7$CO$_2$,
CH$_3$CH$_2$CH=CHCH$_2$CH=CHCH$_2$CH=CH(CH$_2$)$_7$CO$_2$,
CH$_3$(CH$_2$)$_4$CH=CHCH$_2$CH=CH(CH$_2$)$_7$CO$_2$,
CH$_3$CH$_2$CH=CHCH$_2$CH=CHCH$_2$CH=CHCH$_2$CH=CH(CH$_2$)$_4$CO$_2$,
CH$_3$(CH$_2$)$_6$CH=CH(CH$_2$)$_7$COO, CH$_3$(CH$_2$)$_4$CH=CHCH$_2$CH=CH(CH$_2$)$_7$CO$_2$, and
wherein any of the foregoing may be optionally substituted.

In further embodiments, $R^1$ of the compound of Formula XVI can be selected from the group consisting of:

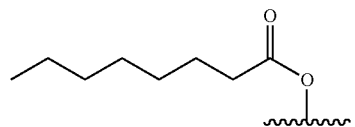 [SMILES: *OC(=O)CCCCCCC]

and

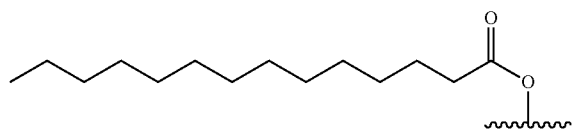 [SMILES: *OC(=O)CCCCCCCCCCCCC]

In further embodiments, $R^2$ of Formula XVI can be selected from the group consisting of:

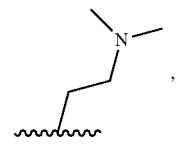 [SMILES: *CCN(C)C]

and

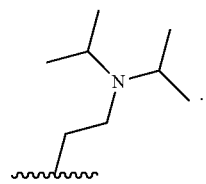 [SMILES: *CCN(C(C)C)C(C)C]

In another preferred embodiment, the present invention includes novel pyrrolopyridine analogs of Psilocin having an O-acyl group modification, which may facilitate transdermal delivery and/or bioavailability of the compound. In another aspect, the present invention includes novel imidazopyridine analog of Psilocin having an O-acyl group modification. In one embodiment a novel O-linked acyl group modification may include O-linked esters of linear saturated and mono- and di-unsaturated acids, and preferably naturally occurring mono- and di-, or polyunsaturated acids. In a preferred embodiment, an O-linked esters of linear saturated or unsaturated acids may include a $C_1$-$C_{18}$, or preferably a $C_7$-$C_{13}$ linear saturated or unsaturated acids.

In another embodiment, the present invention includes a novel analog of Psilocin according to Formula V:

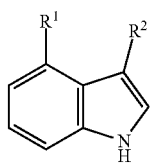

(Formula V)

wherein $R^1$ is H, a protecting group, a protected oxygen, an O-linked acyl, said acyl having a general formula of R'—C(=O)-D, wherein R' is O, and wherein D is an alkane, such as a saturated linear alkane, or an unsaturated linear alkane. $R^2$ may be an amine, or a linear alkane-$R^3$, wherein $R^3$ is $(CH_3)_2NH$ (dimethylamine), or $(CH_3)_2NH$ (diisopropylamine). In one embodiment, the linear alkane-$R^3$ may comprise $CH_2CH_2$—$R^3$.

In another aspect, the present invention includes a novel analog of Psilocin according to Formula V:

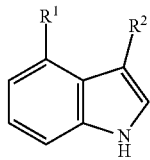

(Formula V)

In another embodiment, the present invention includes a novel analog of Psilocin according to Formula V wherein: $R^1$ is H, a protecting group, a protected oxygen, an O-linked acyl, said acyl having a general formula of R'—C(=O)-D, wherein R' is O, and wherein D is an alkane, is an alkane, such as a saturated linear alkane, or an unsaturated linear alkane. In alternative embodiments, D may include an O-linked ester of a saturated ester or an unsaturated acid ester, or a linear saturated ester, or a linear unsaturated acid ester. In this embodiment, $R^2$ may be an amine, or a linear alkane-$R^3$, wherein $R^3$ is $(CH_3)_2NH$ (dimethylamine), or $CH_3CH(CH_3)NHCH(CH_3)CH_3$ (diisopropylamine). In one embodiment, the linear alkane-$R^3$ may comprise, a $C_2$ linear alkane coupled with —$R^3$, such as preferably $CH_2CH_2$—$R^3$, such that $R^2$ may include $CH_2CH_2$-dimethylamine, or a $C_2$ linear alkane-diisopropylamine.

In additional aspects, any of the foregoing may be optionally substituted, or a prodrug, therapeutically active metabolite, hydrate, solvate, or pharmaceutically acceptable salt thereof. In certain other embodiments, D is a $C_1$-$C_{18}$ linear saturated alkane, or a $C_1$-$C_{18}$ linear unsaturated alkane.

In another embodiment, a saturated linear alkane of the compound of Formula V includes a saturated linear ester selected from the group consisting of:

$HCO_2$, $H_3CCO_2$, $H_3C(CH_2)CO_2$, $H_3C(CH_2)_2CO_2$, $H_3C(CH_2)_3CO_2$, $H_3C(CH_2)_4CO_2$, $H_3C(CH_2)_5CO_2$, $H_3C(CH_2)_6CO_2$, $H_3C(CH_2)_7CO_2$, $H_3C(CH_2)_8CO_2$, $H_3C(CH_2)_9CO_2$, $H_3C(CH_2)_{10}CO_2$, $H_3C(CH_2)_{11}CO_2$, $H_3C(CH_2)_{12}CO_2$, $H_3C(CH_2)_{13}CO_2$, $H_3C(CH_2)_{14}CO_2$, $H_3C(CH_2)_{15}CO_2$, and $H_3C(CH_2)_{16}CO_2$ and wherein any of the foregoing may be optionally substituted.

In another preferred embodiment, a linear unsaturated acid ester of the linear ester of the compound of Formula V includes a mono- or poly-unsaturated linear fatty acid ester selected from the group consisting of:

$CH_3(CH_2)CH=CH(CH_2)_7CO_2$, $CH_3(CH_2)_3CH=CH(CH_2)_7CO_2$, $CH_3(CH_2)_5CH=CH(CH_2)_7CO_2$, $CH_3CH_2CH=CHCH_2CH=CHCH_2CH=CH(CH_2)_7CO_2$, $CH_3(CH_2)_4CH=CHCH_2CH=CH(CH_2)_7CO_2$, $CH_3CH_2CH=CHCH_2CH=CHCH_2CH=CHCH_2CH=CH(CH_2)_4CO_2$, $CH_3(CH_2)_6CH=CH(CH_2)_7COO$, $CH_3(CH_2)_4CH=CHCH_2CH=CH(CH_2)_7CO_2$, and wherein any of the foregoing may be optionally substituted.

In further embodiments, $R^1$ of the compound of Formula V can be selected from the group consisting of:

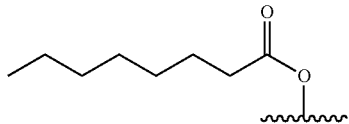 [SMILES: *OC(=O)CCCCCCC]

and

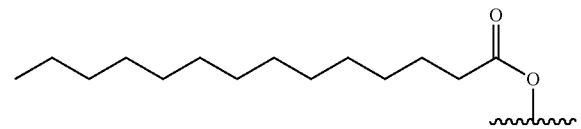 [SMILES: *OC(=O)CCCCCCCCCCCCC]

In still further embodiments, wherein $R^2$ of the compound of Formula V can be selected from the group consisting of:

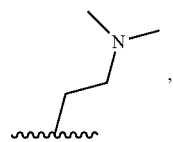 [SMILES: *CCN(C)C]

and

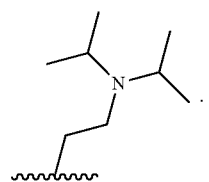 [SMILES: *CCN(C(C)C)C(C)C]

In another embodiment, the present invention includes a novel analog of Psilocin according to Formula VII, and its method of synthesis:

(Formula VII)

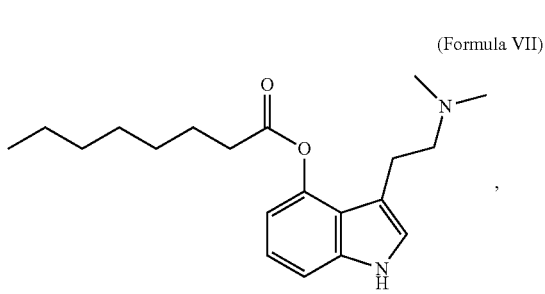 [SMILES: CCCCCCCC(=O)Oc1cccc2[nH]cc(CCN(C)C)c12]

or a prodrug, therapeutically active metabolite, hydrate, solvate, or pharmaceutically acceptable salt thereof.

In another embodiment, the present invention includes a novel analog of Psilocin according to Formula VIII, and its method of synthesis:

(Formula VIII)

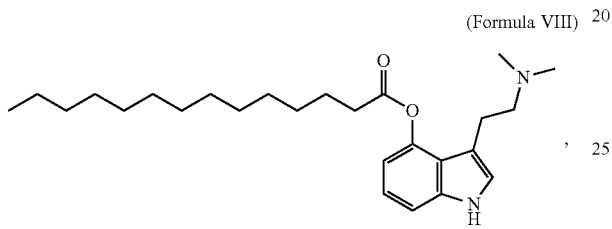

or a prodrug, therapeutically active metabolite, hydrate, solvate, or pharmaceutically acceptable salt thereof.

In another embodiment, the present invention includes a novel analog of Psilocin according to Formula X, and its method of synthesis:

(Formula X)

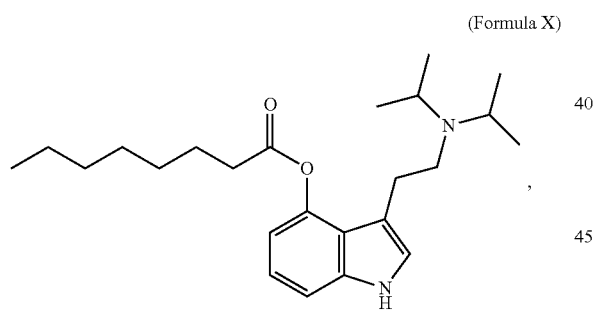

or a prodrug, therapeutically active metabolite, hydrate, solvate, or pharmaceutically acceptable salt thereof.

In another embodiment, the present invention includes a novel analog of Psilocin according to Formula XII, and its method of synthesis:

(Formula XII)

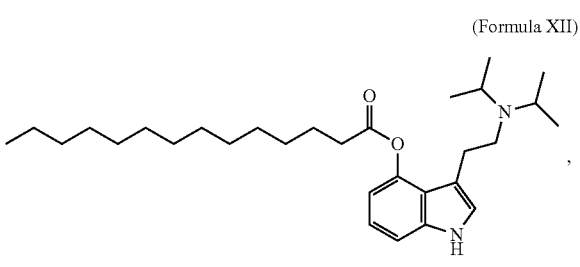 [SMILES: CCCCCCCCCCCCCC(=O)Oc1cccc2[nH]cc(CCN(C(C)C)C(C)C)c12]

or a prodrug, therapeutically active metabolite, hydrate, solvate, or pharmaceutically acceptable salt thereof.

Another aspect of the invention may include a compound selected from the group consisting of:

(Formula I)

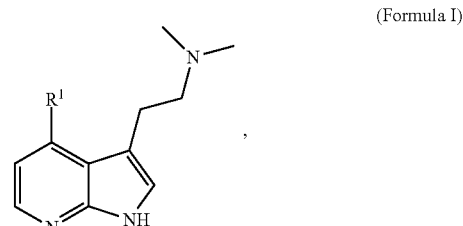

(Formula II)

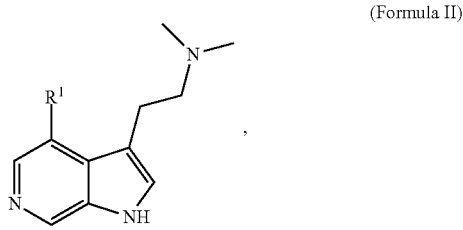

(Formula III)

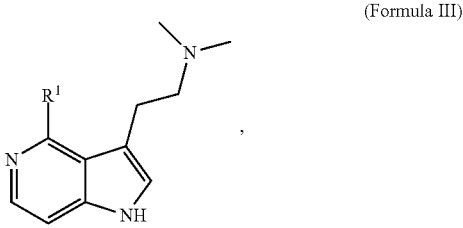

(Formula IV)

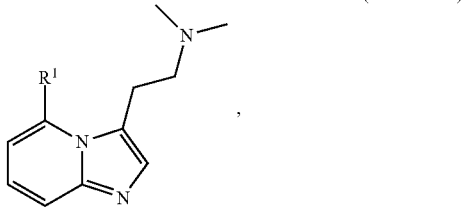

wherein
R$^1$ is H, —OH, —OP(O)(OH)$_2$, a protecting group, an O-linked acyl, said acyl having a general formula of R'—C(=O)-D, wherein R' is optionally an O, and wherein D is an alkane, and preferably a C$_1$-C$_{18}$ linear alkane, or an O-linked ester of a saturated ester or an unsaturated acids ester, and preferably a C$_1$-C$_{18}$ linear saturated ester or a linear unsaturated acid ester, wherein said saturated linear alkane comprises a saturated linear ester selected from the group consisting of:
HCO$_2$, H$_3$CCO$_2$, H$_3$C(CH$_2$)CO$_2$, H$_3$C(CH$_2$)$_2$CO$_2$, H$_3$C(CH$_2$)$_3$CO$_2$, H$_3$C(CH$_2$)$_4$CO$_2$,
H$_3$C(CH$_2$)$_5$CO$_2$, H$_3$C(CH$_2$)$_6$CO$_2$, H$_3$C(CH$_2$)$_7$CO$_2$, H$_3$C(CH$_2$)$_8$CO$_2$,
H$_3$C(CH$_2$)$_9$CO$_2$, H$_3$C(CH$_2$)$_{10}$CO$_2$, H$_3$C(CH$_2$)$_{11}$CO$_2$, H$_3$C(CH$_2$)$_{12}$CO$_2$,
H$_3$C(CH$_2$)$_{13}$CO$_2$, H$_3$C(CH$_2$)$_{14}$CO$_2$, H$_3$C(CH$_2$)$_{15}$CO$_2$, H$_3$C(CH$_2$)$_{16}$CO$_2$, wherein said unsaturated linear alkane comprises a mono- or poly-unsaturated linear fatty acid ester selected from the group consisting of:
CH$_3$(CH$_2$)CH=CH(CH$_2$)$_7$CO$_2$,
CH$_3$(CH$_2$)$_3$CH=CH(CH$_2$)$_7$CO$_2$,
CH$_3$(CH$_2$)$_5$CH=CH(CH$_2$)$_7$CO$_2$, CH₃CH₂CH=CHCH₂CH=CHCH₂CH=CH(CH₂)₇ CO₂,
CH₃(CH₂)₄CH=CHCH₂CH=CH(CH₂)₇CO₂,
CH₃CH₂CH=CHCH₂CH=CHCH₂CH=CHCH₂ CH=CH(CH₂)₄CO₂,
CH₃(CH₂)₆CH=CH(CH₂)₇COO, CH₃(CH₂)₄ CH=CHCH₂CH=CH(CH₂)₇CO₂, and wherein any of the foregoing may be optionally substituted, and wherein the compounds includes a prodrug, therapeutically active metabolite, hydrate, solvate, or pharmaceutically acceptable salt thereof.

Another aspect of the invention may include a compound according to the following:

(Formula 1A)

wherein
X², X³, and X⁴ is independently N, or CH;
A is N, or C, however where A is N, X², X³, and X⁴ are CH, and wherein said dashed line represents possible double bond positions according to the configuration of A, and X², X³, and X⁴ being N or CH;
X¹ is C, or R¹ which is H, —OH, —OP(O)(OH)₂, a protecting group, an O-linked acyl, said acyl having a general formula of R'—C(=O)-D, wherein R' is optionally an O, and wherein D is an alkane, and preferably a C₁-C₁₈ linear alkane, or an O-linked ester of a saturated ester or an unsaturated acids ester, and preferably a C₁-C₁₈ linear saturated ester or a linear unsaturated acid ester,
wherein said saturated linear alkane optionally comprises a saturated linear ester selected from the group consisting of:
HCO₂, H₃CCO₂, H₃C(CH₂)CO₂, H₃C(CH₂)₂CO₂, H₃C(CH₂)₃CO₂, H₃C(CH₂)₄CO₂,
H₃C(CH₂)₅CO₂, H₃C(CH₂)₆CO₂, H₃C(CH₂)₇CO₂, H₃C(CH₂)₈CO₂,
H₃C(CH₂)₉CO₂, H₃C(CH₂)₁₀CO₂, H₃C(CH₂)₁₁CO₂, H₃C(CH₂)₁₂CO₂,
H₃C(CH₂)₁₃CO₂, H₃C(CH₂)₁₄CO₂, H₃C(CH₂)₁₅CO₂, H₃C(CH₂)₁₆CO₂,
wherein said unsaturated linear alkane ester optionally comprises a mono- or poly-unsaturated linear fatty acid ester selected from the group consisting of:
CH₃(CH₂)CH=CH(CH₂)₇CO₂,
CH₃(CH₂)₃CH=CH(CH₂)₇CO₂,
CH₃(CH₂)₅CH=CH(CH₂)₇CO₂,
CH₃CH₂CH=CHCH₂CH=CHCH₂CH=CH(CH₂)₇ CO₂,
CH₃(CH₂)₄CH=CHCH₂CH=CH(CH₂)₇CO₂,
CH₃CH₂CH=CHCH₂CH=CHCH₂CH=CHCH₂ CH=CH(CH₂)₄CO₂,
CH₃(CH₂)₆CH=CH(CH₂)₇COO, CH₃(CH₂)₄ CH=CHCH₂CH=CH(CH₂)₇CO₂,
and wherein any of the foregoing may be optionally substituted.

Additional embodiments of the current invention include a compound of Formula I-XXIII, or a pharmaceutically acceptable salt, solvate, stereoisomer, tautomer, or prodrug thereof, for use in recreational, psychological, or medical therapies.

Another aspect of the invention may include a psilocin analog compound according to Formula XVII, also referred to herein:

or a prodrug, therapeutically active metabolite, hydrate, solvate, or pharmaceutically acceptable salt thereof.

Another aspect of the invention may include a psilocin analog compound according to Formula XVII, also referred to herein as MY205B:

or a prodrug, therapeutically active metabolite, hydrate, solvate, or pharmaceutically acceptable salt thereof.

Another aspect of the invention may include a psilocin analog compound according to Formula XIX, also referred to herein as MY205C:

or a prodrug, therapeutically active metabolite, hydrate, solvate, or pharmaceutically acceptable salt thereof.

Another aspect of the invention may include a psilocin analog compound according to Formula XX, also referred to herein as MY205DT:

or a prodrug, therapeutically active metabolite, hydrate, solvate, or pharmaceutically acceptable salt thereof.

Another aspect of the invention may include a psilocin analog compound according to Formula XXI, also referred to herein as MY331A:

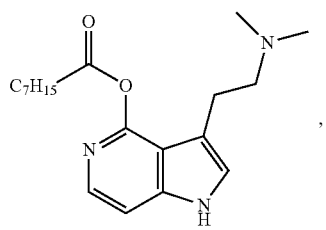

or a prodrug, therapeutically active metabolite, hydrate, solvate, or pharmaceutically acceptable salt thereof.

Another aspect of the invention may include a psilocin analog compound according to Formula XXII, also referred to herein as MY331B:

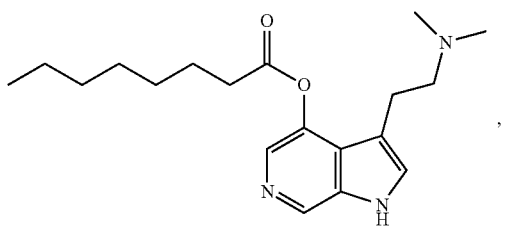 [SMILES: CCCCCCCC(=O)Oc1cncc2[nH]cc(CCN(C)C)c12]

or a prodrug, therapeutically active metabolite, hydrate, solvate, or pharmaceutically acceptable salt thereof.

Another aspect of the invention may include a psilocin analog compound according to Formula XXIII, also referred to herein as MY333B:

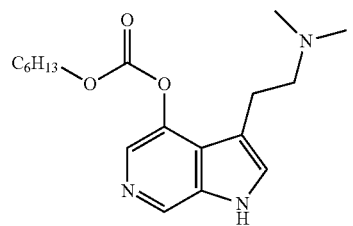

or a prodrug, therapeutically active metabolite, hydrate, solvate, or pharmaceutically acceptable salt thereof.

One embodiment of the present invention provides a systems, methods, and compositions for novel psilocin analogs according to the compounds of Formula I-XXIII (also referred to as a/the compound(s) of the invention) and a pharmaceutically acceptable carrier or diluent, which may preferably further include a method of treatment of the human or animal body using one or more of the novel compounds, or pharmaceutical compositions described herein.

In another embodiment, the present invention provides the use of one or more of the novel psilocin analogs according to the compounds of Formula I-XXIII are serotonin receptor agonists. As used herein, a "serotonin receptor agonists" means a substance, and preferably a compound of the invention, having the function of acting on a serotonin receptor, and includes, for example, a 5-HT2A, 5-HT2C and 5-HT1A 5-HT2A receptor agonist. As used herein, an "agonist" means a substance, and preferably a compound of the invention, having the function of binding/activating to a receptor or to produce a biological response. In another embodiment, the present invention provides the use of one or more of the novel psilocin analogs according to the compounds of Formula I-XXIII for the treatment of a disease or condition, and preferably a disease or condition in a subject that is may be treated by activating of one or more serotonin receptors by the agonist action of one or more compounds of the invention in a subject in need thereof.

A compound of Formula I-XXIII, or a pharmaceutically acceptable salt thereof, for use in the modulation of serotonin receptor activity in research, pharmaceutical, and biotechnology development. A compound of Formula I-XXIII, or a pharmaceutically acceptable salt thereof, for use in the treatment of a disease or condition in which modulation of serotonin receptor activity is beneficial.

A method for treating a disease or condition for which modulation of serotonin receptor activity is beneficial comprising the steps of administering to a subject in need thereof, a therapeutically effective amount of a compound of I-XXIII, or a pharmaceutically acceptable salt thereof. A method for treating a disease or condition for which modulation of serotonin receptor is beneficial comprising the steps of administering to a subject in need thereof, a therapeutically effective amount of a combination comprising a compound of Formula I-XXIII, or a pharmaceutically acceptable salt thereof, and at least one further therapeutic agent, wherein said further therapeutic agent may optionally be a serotonin receptor agonist, or a Monoamine Oxidase Inhibitors (MAOIs).

A method for treating a disease or condition for which modulation of serotonin receptor is beneficial comprising: administering to a subject in need thereof, a therapeutically effective amount of a combination comprising a compound of Formula I-XXIII, or a pharmaceutically acceptable salt thereof, and at least one further therapeutic agent, wherein said further therapeutic agent is selected from the group consisting of: 1) a tryptamine compound, or a tryptamine compound and an entactogen. As used herein, "tryptamine" means compounds having affinity for a serotonin receptor and may include, but not be limited to: substituted tryptamines, psilocybin, psilocin, N,N-dimethyltryptamine, 5-methoxy-N,N-dimethyltryptamine, N,N-Dipropyltryptamine, 5-methoxy-N,N-Dipropyltryptamine, baeocystin ([3-[2-(methylamino)ethyl]-1H-indol-4-yl] di hydrogen phosphate), norbaeocystin ([3-(2-aminoethyl)-1H-indol-4-yl] dihydrogen phosphate), aeruguinascin (N,N,N-trimethyl-4-phosphorl-oxytryptamine), 4-acetoxy-N,N-dimethyltryptamine, 3-(2'-dimethylaminoethyl)-4-acetoxy-indole. As used herein, "entactogens" means a compounds having the effect of releasing serotonin, norepinephrine and dopamine such as 3,4-methylenedioxyamphetamine (MDMA), 2,5-dimethoxy-4-bromophenethylamine, 3,4-methylenedioxyN-ethylamphetamine, a-lfamethyltryptamine and alpha-ethyltryptamine.

The use of a compound of Formula I-XXIII, or a pharmaceutically acceptable salt thereof, in the manufacture of a pharmaceutical composition for use the treatment of a disease or condition for which modulation of serotonin receptor is beneficial. A pharmaceutical composition comprising a compound of Formula I-XXIII, or a pharmaceutically acceptable salt thereof, for use in the treatment of a disease or condition for which modulation of serotonin receptor is beneficial. A pharmaceutical composition comprising a compound of Formula I-XXIII, or a pharmaceutically acceptable salt thereof, and at least one further therapeutic agent, wherein said further therapeutic agent is optionally selected from the group consisting of: 1) a tryptamine compound, and/or an entactogen for use in the treatment of a disease or condition for which modulation of serotonin receptor activity is beneficial.

A compound of the invention or pharmaceutical composition comprising the compound may be administered to a "subject," and preferably a human subject, by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. The subject may be a eukaryote, an animal, a vertebrate animal, a mammal, a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), an ape (e.g., gorilla, chimpanzee, orangutan, gibbon), or a human.

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary, shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrants will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet. Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents. Exemplary tablets contain up to about 80 wt % drug, from about 10 wt % to about 90 wt % binder, from about O wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated. The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-, pulsed-, controlled-, targeted and programmed release. Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams, or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

The invention now being generally described will be more readily understood by reference to the following examples, which are included merely for the purposes of illustration of certain embodiments of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Novel Psilocin Prodrug Analogs

In one embodiment, the invention include one or more novel Psilocin prodrug analogs an O-linked moiety that may enhance the compounds lipophilicity and thereby facilitate transdermal delivery of the compound. As shown above, the compounds of Formulas I-V, VII-VIII, X, and XII describe novel analogs of Psilocin containing one or more O-linked acyl modifications at positions $R^1$. As further shown above, the compounds of the invention may further describe novel analogs of Psilocin containing one or more N or aza substitutions to their Azaindole groups as well as one or more O-linked Acyl modifications at position $R^1$. In one embodiment a novel O-linked acyl group modification may include, but not be limited to, O-linked esters of linear saturated and/or unsaturated acids, such as mono- and poly-unsaturated acids, and preferably naturally occurring mono- and di-unsaturated acids. In a preferred embodiment, an O-linked esters of linear saturated or mono- and di-unsaturated acids may include a $C_1$-$C_{18}$ linear saturated or mono- or polyunsaturated acids. (See Table 1 and 2 below)

Example 2: Synthesis of Novel Analog
3-(2-(dimethylamino)ethyl)-1H-indol-4-yl Acetate As shown in Scheme 1 below, the present invention provides for the step wise production of novel analog 3-(2-(dimethylamino)ethyl)-1H-indol-4-yl acetate also referred to herein as MY246 and Formula XIII:

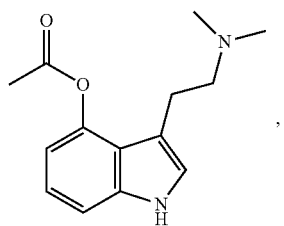 [SMILES: CC(=O)Oc1cccc2[nH]cc(CCN(C)C)c12]

according to the following scheme:

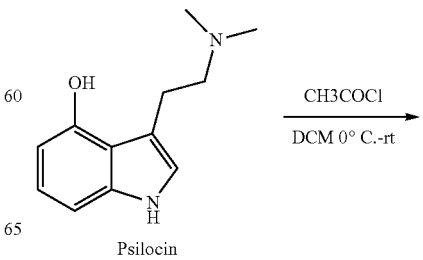

Scheme 1

-continued

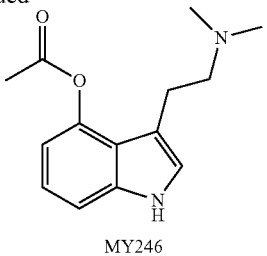

MY246

As described in Scheme 1 above, in this embodiment, the present inventors demonstrated the synthesis of the novel psilocin prodrug analog compound MY246, also referred to herein as Formula XIII. In this embodiment, to a clear solution of Psilocin (0.20 g, 0.98 mmol, 1 eq) in anhydrous DCM (10 mL) at 0-5° C. under nitrogen was added acetyl chloride (0.15 g, 1.96 mmol, 2.0 eq) slowly via a syringe. The resultant mixture was allowed warm to 23±2° C. (RT) and stirred at that temperature for 16 h. The reaction mixture was analyzed by TLC to check the progress and completion of the reaction (Silica plate, 1% concentrated $NH_4OH$ aq/10% MeOH in DCM). The reaction mixture was quenched with water (10 mL) and sat. $NaHCO_3$ aq (10 mL), and the layers were separated. The DCM layer was dried over $Na_2SO_4$, concentrated under vacuum to give a residue, which was purified by silica gel chromatography eluting with 10% (10% $NH_4OH$ aq/MeOH) in DCM to give a pale yellow oil, which contained small amount of starting material (by TLC). This solid was suspended in a mixture of EtOAc (0.2 mL)/hexanes (0.8 mL), stirred at rt for 2 h and filtered, washed with hexanes (1 mL), dried in vacuum to afford 3-(2-(dimethylamino)ethyl)-1H-indol-4-yl acetate as white solid (0.081 g, yield 33%, Lot #: MNC(01)-4R-4). $^1H$ NMR (600 MHz, $CDCl_3$): 8.10 (br s, 1H), 7.22 (d, J=7.8 Hz, 1H), 7.15 (t, J=7.8 Hz, 1H), 7.00 (s, 1H), 6.72 (dd, J=0.6 and 7.8 Hz, 1H), 2.94 (m, 2H), 2.62 (m, 2H), 2.42 (s, 3H), 2.33 (s, 6H). $^{13}C$ NMR (150 MHz, $CDCl_3$): 170.0, 144.1, 138.6, 122.3, 122.1, 119.9, 113.2, 112.3, 109.2, 60.9, 45.6, 24.9, 21.2. LCMS (ES) m/z calc. for $C_{14}H_{19}N_2O_2$ $(M+1)^+$, 247.14; found, 247.06.

Example 3: Synthesis of Novel Analog 3-(2-(dimethylamino)ethyl)-1H-indol-4-yl Octanoate As shown in Scheme 2 below, the present invention provides for the step wise production of novel analog 3-(2-(dimethylamino)ethyl)-1H-indol-4-yl octanoate also referred to herein as MY330 and Formula VII:

according to the following scheme:

Scheme 2

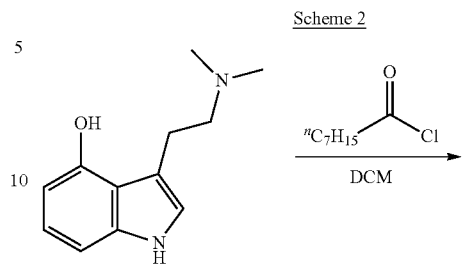

Psilocin

MY330

As described in Scheme 2 above, in this embodiment, the present inventors demonstrated the synthesis of the novel psilocin prodrug analog compound MY330, also referred to herein as Formula VII. In this embodiment, to a clear solution of Psilocin (0.41 g, 2.0 mmol, 1 eq) in anhydrous DCM (40 mL) at 0° C. to 5° C. under nitrogen was added Octanoyl chloride (0.75 mL, 4.3 mmol, 2.2 eq) slowly via a syringe. The resultant mixture was allowed warm to rt and stirred at that temperature for 16 h. TLC indicated that the reaction was near finished (desired product Rf 0.21; starting material Psilocin Rf 0.2; Silica plate, 0.4% concentrated $NH_4OH$ aq/4% MeOH in EtOAc). The reaction mixture was cooled to 0° C. to 5° C., quenched with water (20 mL) and sat. $NaHCO_3$ aq (10 mL), and the layers were separated. The DCM layer was dried over $Na_2SO_4$, concentrated under vacuum to give a crude oil. The crude oil was purified by silica gel chromatography eluting with 2%~4% (10% $NH_4OH$ aq/MeOH) in DCM to give a pale yellow oil (0.6 g) which contained small amount of starting material (by NMR). This oil was dissolved in 10% EtOAc/hexanes (10 mL), stirred at rt for 5 h and precipitation formed. The precipitation was collected by filtration, washed with 10% EtOAc/hexanes (10 mL), dried in vacuum to afford the desired product 3-(2-(dimethylamino)ethyl)-1H-indol-4-yl octanoate as off-white solid (0.42 g, yield 63%). Melting Point: 69° C. to 70° C. $^1H$ NMR (600 MHz, $CDCl_3$): δ 8.10 (br s, 1H), 7.22 (d, J=8.4 Hz, 1H), 7.15 (t, J=7.8 Hz, 1H), 6.99 (d, J=1.8 Hz, 1H), 6.81 (dd, J=1.2 and 7.8 Hz, 1H), 2.93 (dt, J=1.8 and 7.8 Hz, 2H), 2.69 (t, J=7.8 Hz, 2H), 2.62 (t, J=7.8 Hz, 2H), 2.33 (s, 6H), 1.82-1.85 (m, 2H), 1.46-1.48 (m, 2H), 1.32-1.40 (m, 6H), 0.93 (t, J=7.2 Hz, 3H). $^{13}C$ NMR (150 MHz, $CDCl_3$): δ 172.7, 144.2, 138.6, 122.1, 122.0, 120.0, 113.3, 112.3, 108.9, 60.8, 45.6, 34.5, 31.7, 29.2, 29.0, 25.0, 24.9, 22.6, 14.1. LCMS m/z=331 $[M+1]^+$

Example 4: Synthesis of Novel Analog 3-(2-(dimethylamino)ethyl)-1H-indol-4-yl Tetradecanoate As shown in Scheme 3 below, the present invention provides for the step wise production of novel analog MY414 also referred to herein and Formula VIII:

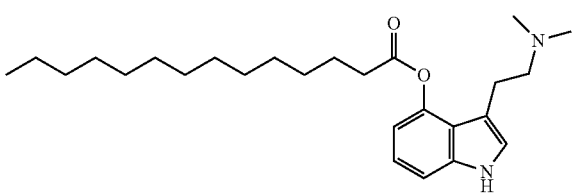 [SMILES: CCCCCCCCCCCCCC(=O)Oc1cccc2[nH]cc(CCN(C)C)c12]

according to the following scheme:

Scheme 3

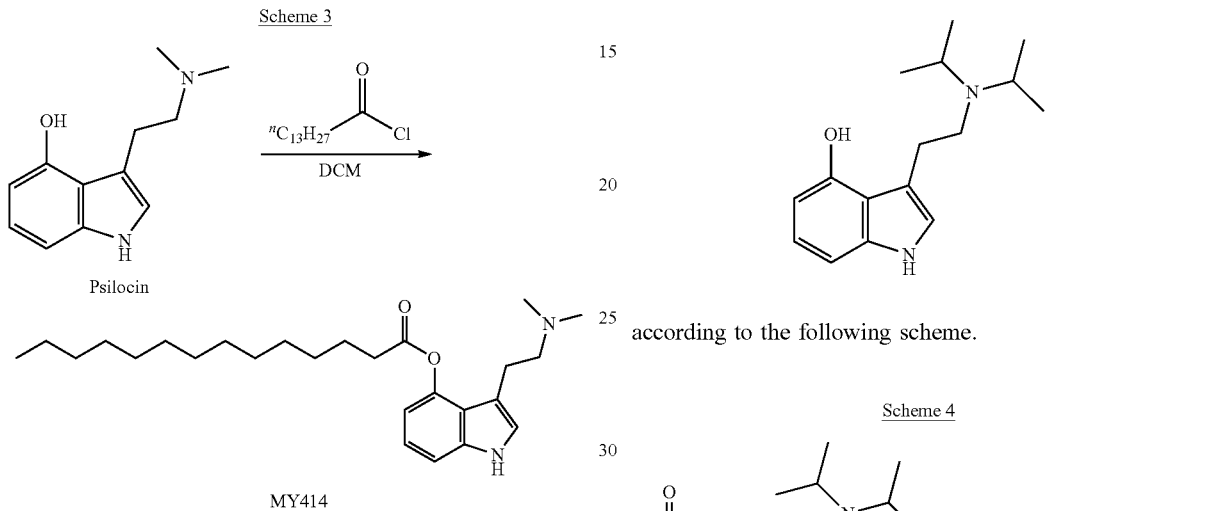

MY414

As described in Scheme 3 above, in this embodiment, the present inventors demonstrated the synthesis of the novel psilocin prodrug analog compound MY414, also referred to herein as Formula VIII. In this embodiment, to a clear solution of Psilocin (0.31 g, 1.5 mmol, 1 eq) in anhydrous DCM (30 mL) at 0~5° C. under nitrogen was added Myristoyl chloride (0.83 g, 3.3 mmol, 2.2 eq) slowly via a syringe. The resultant mixture was allowed warm to rt and stirred at that temperature for 16 h. TLC indicated that the reaction was near finished (desired product Rf 0.22; starting material Psilocin Rf 0.2; Silica plate, 0.4% concentrated $NH_4OH$ aq/4% MeOH in EtOAc). The reaction mixture was cooled to 0~5° C., quenched with water (20 mL) and sat. $NaHCO_3$ aq (10 mL), and the layers were separated. The DCM layer was dried over $Na_2SO_4$, concentrated under vacuum to give a crude oil. The crude oil was purified by silica gel chromatography eluting with 2% (10% $NH_4OH$ aq/MeOH) in EtOAc to give a pale yellow oil (0.41 g). This oil was slurried in hexanes (10 mL) and heated to reflux to form a clear solution. The clear solution was cooled slowly to rt, and then keep in −20° C. for 16 h, white precipitation formed at −20° C. The precipitation was collected by filtration, washed with hexanes (10 mL), dried in vacuum to afford the desired product 3-(2-(dimethylamino)ethyl)-1H-indol-4-yl tetradecanoate as off-white solid (0.31 g, yield 49%). Melting Point: 58° C. to 59° C. $^1$H NMR (600 MHz, $CDCl_3$): δ 8.08 (br s, 1H), 7.23 (d, J=7.8 Hz, 1H), 7.15 (t, J=7.8 Hz, 1H), 7.00 (d, J=1.8 Hz, 1H), 6.81 (dd, J=0.6 and 7.8 Hz, 1H), 2.93 (dt, J=0.6 and 7.2 Hz, 2H), 2.69 (t, J=7.2 Hz, 2H), 2.62 (t, J=7.2 Hz, 2H), 2.33 (s, 6H), 1.80-1.85 (m, 2H), 1.45-1.48 (m, 2H), 1.27-1.38 (m, 18H), 0.91 (t, J=7.2 Hz, 3H). $^{13}$C NMR (150 MHz, $CDCl_3$): δ 172.7, 144.2, 138.6, 122.1, 122.0, 120.0, 113.3, 108.9, 60.7, 45.5, 34.5, 31.9, 29.7, 29.6, 29.5, 29.4, 29.3, 29.3, 29.3, 29.2, 24.9, 24.8, 22.7, 14.1. LCMS m/z=415 [M+1]$^+$ Example 5: Synthesis of novel analog 3-(2-(diisopropylamino)ethyl)-1H-indol-4-ol As shown in Scheme 4 below, the present invention provides for the step wise production of novel analog 3-(2-(dimethylamino)ethyl)-1H-pyrrolo[2,3-c]pyridin-4-ol also referred to herein as MY260 and Formula IX:

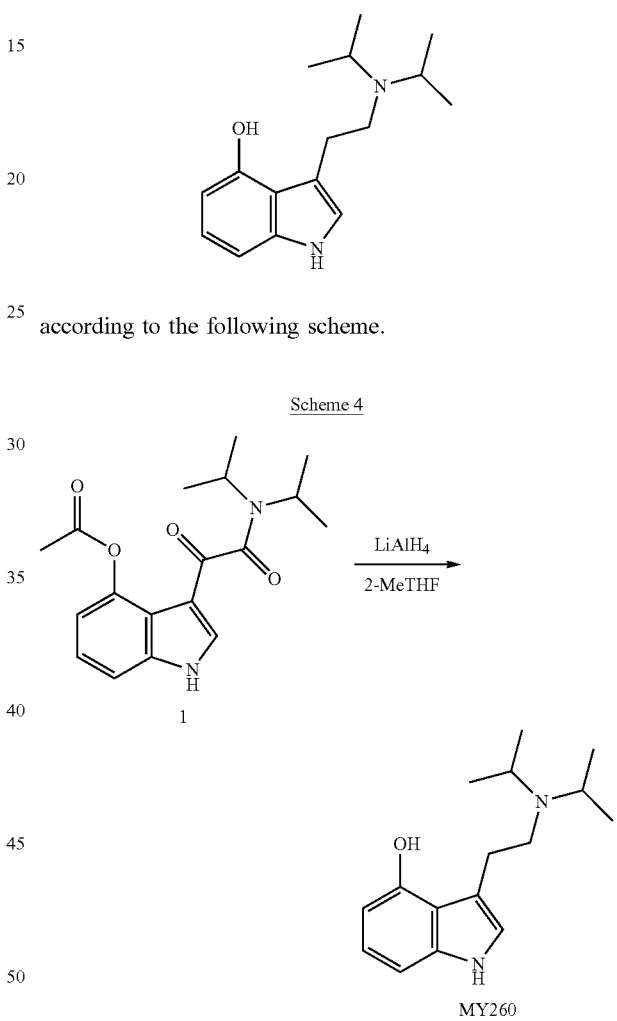

according to the following scheme.

As described in Scheme 4 above, in this embodiment, the present inventors demonstrated the synthesis of the novel psilocin prodrug analog compound MY260, also referred to herein as Formula IX. In this embodiment, to a suspension of compound 1 (0.8 g, 2.42 mmol, 1 eq.) in anhydrous 2-MeTHF (25 mL) at 0° C. to 5° C. under nitrogen was added 2.3 M $LiAlH_4$ solution in 2-MeTHF (5.0 mL, 11.5 mmol, 4.7 eq) slowly over a period of 5 minutes via a syringe. The resultant mixture was allowed warm to room temperature and then heated to reflux (internal 75° C., oil bath 85-95° C.) for 6 h. The reaction mixture was analyzed by TLC to check the progress of the reaction and confirm the completion of the reaction (β-Hydroxy intermediate Rf 0.2; Desired product Rf 0.4; Starting material Rf 0.45; Silica plate, 1% concentrated NH$_4$OH aq/10% MeOH in DCM). Heating was discontinued and the reaction mixture was cooled to room temperature and then cooled to 0° C. to 5° C. with ice-water bath. Quench the reaction by drop wise addition of the acetone (2 mL), with vigorous stirring, maintaining the temperature of the resulting slurry at about 20° C. to 25° C. by adjusting the rate of addition. An aqueous solution of citric acid (0.27 g citric acid monohydrate (1.2 mmol, 0.5 eq) in water (0.7 mL) was then added drop wise to the reaction slurry. The resulting suspension was stirred at room temperature for 30 to 40 minutes, anhydrous sodium sulphate (2 g) was added, followed by Silica gel (2 g, 230~400 mesh). The reaction mixture was diluted with 10% MeOH/DCM (30 mL), stirred at room temperature for 30 minutes, and filtered through celite. The filtrate was concentrated under vacuum to obtained desired product 3-(2-(diisopropylamino)ethyl)-1H-indol-4-ol (MY260, 0.54 g, yield: 85%) as a beige glass solid which was used for next step without further purification. $^1$H NMR (600 MHz, CDCl$_3$): δ 12.94 (br s, 1H), 7.83 (br s, 1H), 7.06 (t, J=7.8 Hz, 1H), 6.85 (dd, J=1.2 and 8.4 Hz, 1H), 6.84 (d, J=2.4 Hz, 1H), 6.56 (dd, J=1.2 and 7.8 Hz, 1H), 3.14 (m, 2H), 3.00 (m, 2H), 2.82 (m, 2H), 1.04 (d, J=6.0 Hz, 12H). $^{13}$C NMR (150 MHz, CDCl$_3$): δ 151.9, 138.4, 123.4, 120.5, 118.9, 114.6. 106.5, 102.3, 50.4, 48.2, 27.7, 19.4. LCMS m/z=261 [M+1]$^+$.

Notably, synthesis of Compound 1 of Scheme 4, follows the synthesis pathway shown below as Scheme 8. To this mixture was slowly added add 2.3 M LiAlH$_4$ solution in 2-MeTHF (11.5 mmol, 4.7 eq). The reaction mixture was allowed to warm to (23±2) ° C. and then the reaction mixture heated under reflux using an oil bath. The progress of the reaction was monitored to completion by TLC. The compounds were purified by chromatography and concentrated under a vacuum to obtain the product MY260.

Scheme 8

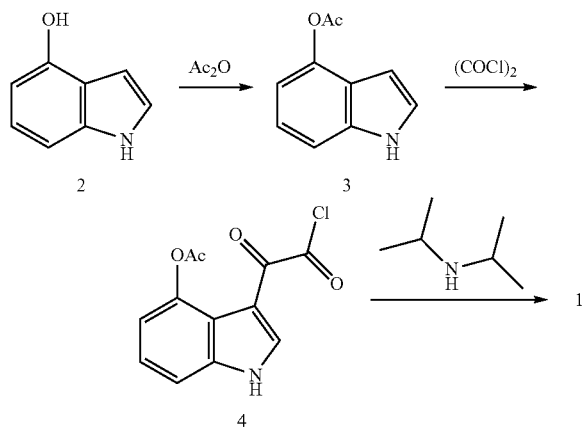

General Synthesis Pathway of Compound 1 (3-(2-(diisopropylamino)-2-oxoacetyl)-1H-indol-4-yl acetate

Example 6: Synthesis of Novel Analog 3-(2-(diisopropylamino)ethyl)-1H-indol-4-yl Octanoate As shown in Scheme 5 below, the present invention provides for the step wise production of novel analog MY386 also referred to herein and Formula X:

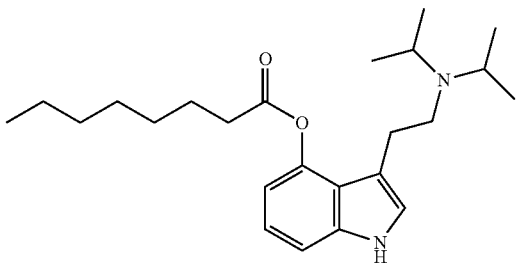 [SMILES: CCCCCCCC(=O)Oc1cccc2[nH]cc(CCN(C(C)C)C(C)C)c12]

according to the following scheme:

Scheme 5

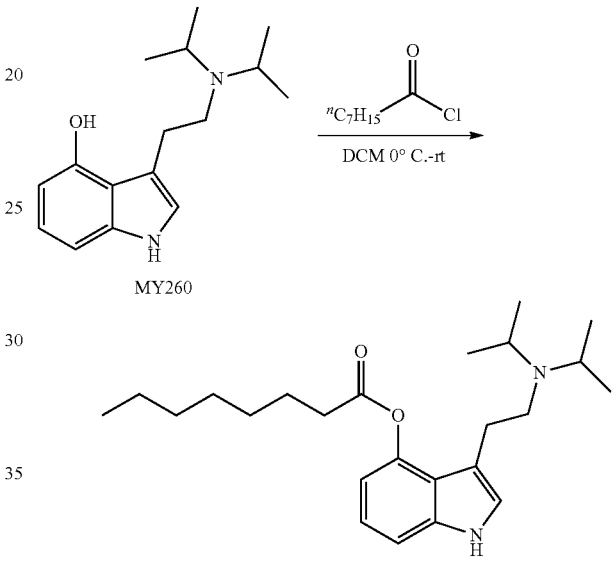

As described in Scheme 5 above, in this embodiment, the present inventors demonstrated the synthesis of the novel psilocin prodrug analog compound MY386, also referred to herein as Formula X. In this embodiment, to a clear solution of MY260 (0.15 g, 0.59 mmol, 1 eq) in anhydrous DCM (20 mL) at 0-5° C. under nitrogen was added n-Octanoyl chloride (0.21 g, 1.31 mmol, 2.2 eq) slowly via a syringe. The resultant mixture was allowed to warm to 23±2° C. (RT) and stirred at that temperature for 16 h. The reaction mixture was analyzed by TLC to check the progress and completion of the reaction (Silica plate, 0.5% concentrated NH$_4$OH aqueous/5% MeOH in EtOAc). The reaction mixture was quenched with water (10 mL) and sat. NaHCO$_3$ aqueous (10 mL). The DCM layer was separated and dried over Na$_2$SO$_4$, concentrated under vacuum to give a residue, which was purified by silica gel chromatography eluted with 4% (10% NH$_4$OH aqueous/MeOH) in EtOAc to give a pale yellow oil, which was dried under vacuum and stored in −20° C. freezer and obtained 3-(2-(diisopropylamino)ethyl)-1H-indol-4-yl octanoate as off-white solid (0.19 g, yield 82%, Lot #: MNC(05)-4R-5). $^1$H NMR (600 MHz, CDCl$_3$): 8.03 (br s, 1H), 7.23 (d, J=7.2 Hz, 1H), 7.15 (t, J=7.2 Hz, 1H), 7.00 (s, 1H), 6.80 (d, J=7.2 Hz, 1H), 3.11 (m, 2H), 2.86 (m, 2H), 2.74 (m, 2H), 2.68 (m, 2H), 1.80-1.84 (m, 2H), 1.45-1.48 (m, 2H), 1.32-1.40 (m, 6H), 1.08 (m, 12H), 0.93 (t, J=7.2 Hz, 3H). $^{13}$C NMR (150 MHz, CDCl$_3$): 172.8, 144.4, 138.4, 122.0, 121.9, 120.0, 114.1, 112.3, 108.9, 48.4, 46.2, 34.5, 31.7, 29.2, 29.0, 28.2, 25.0, 24.9, 22.6, 20.9, 14.1. LCMS (ES) m/z calc. for $C_{24}H_{39}N_2O_2$ (M+1)$^+$, 387.30; found, 387.35

Example 7: Synthesis of Novel Aza Analog 3-(2-(diisopropylamino)ethyl)-1H-indol-4-yl Acetate As shown in Scheme 6 below, the present invention provides for the step wise production of novel Aza analog 3-(2-(diisopropylamino)ethyl)-1H-indol-4-yl acetate also referred to herein as MY302 and Formula XI:

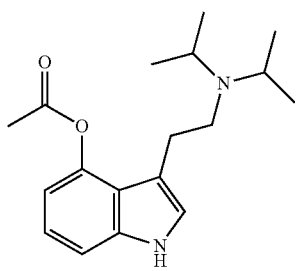 [SMILES: CC(=O)Oc1cccc2[nH]cc(CCN(C(C)C)C(C)C)c12]

according to the following scheme:

Scheme 6

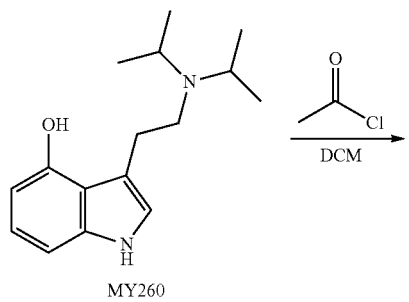

As described in Scheme 6 above, in this embodiment, the present inventors demonstrated the synthesis of the novel psilocin prodrug analog compound MY302, also referred to herein as Formula XI. In this embodiment, to a clear solution of compound MY260 (0.096 g, 0.368 mmol, 1 eq) in anhydrous DCM (10 mL) at 0~5° C. under nitrogen was added acetyl chloride (0.1 g, 1.27 mmol, 3.4 eq) slowly via a syringe. The resultant mixture was allowed warm to 23±2° C. (RT) and stirred for 16 h. The reaction mixture was analyzed by TLC to check the progress of the reaction and confirm the completion of the reaction (desired product Rf 0.2; starting material Rf 0.22; Silica plate, 0.5% concentrated NH$_4$OH aq/5% MeOH in DCM). The reaction mixture was cooled to 0~5° C., quenched with water (10 mL) and sat. NaHCO$_3$ aq (5 mL), and the layers were separated. The DCM layer was dried over Na$_2$SO$_4$, concentrated under vacuum to get a crude oil. The crude oil was purified by silica gel chromatography eluting with 2%~4% (10% NH$_4$OH aq/MeOH) in DCM and obtained a pale yellow solid product (0.07 g) which contained small amount of starting material (by TLC). This solid was suspended in a mixture of EtOAc (0.3 mL)/hexanes (1 mL), stirred at rt for 16 h and filtered, washed with 15% EtOAc/hexanes (1 mL), dried under vacuum to get the desired product 3-(2-(diisopropylamino)ethyl)-1H-indol-4-yl acetate as off-white solid (0.028 g, yield 25%). Melting Point: 105° C.~106° C. $^1$H NMR (600 MHz, CDCl$_3$): δ 7.94 (br s, 1H), 7.16 (d, J=8.4 Hz, 1H), 7.06 (t, J=7.8 Hz, 1H), 6.93 (s, 1H), 6.72 (dd, J=0.6 and 7.8 Hz, 1H), 3.00 (m, 2H), 2.76 (m, 2H), 2.64 (m, 2H), 2.32 (s, 3H), 0.95 (d, J=6.6 Hz, 12H). 13C NMR (150 MHz, CDCl$_3$): δ 170.1, 144.3, 138.4, 122.1, 122.0, 114.0, 112.3, 109.1, 48.4, 46.8, 28.3, 21.3, 20.9. LCMS m/z=303 [M+1]$^+$

Example 8: Synthesis of Novel Psilocin Prodrug Analog 3-(2-(diisopropylamino)ethyl)-1H-indol-4-yl Tetradecanoate As shown in Scheme 7 below, the present invention provides for the step wise production of novel Aza analog MY470 also referred to herein and Formula XII:

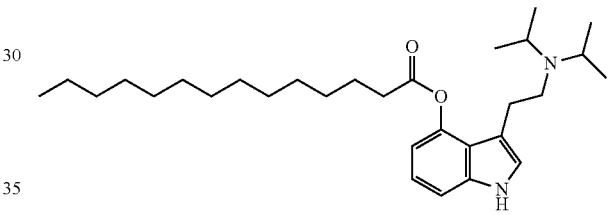

according to the following scheme:

Scheme 7

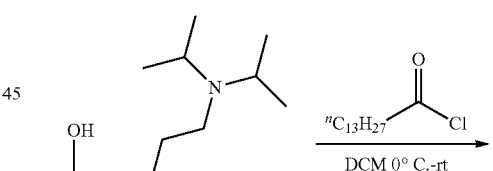

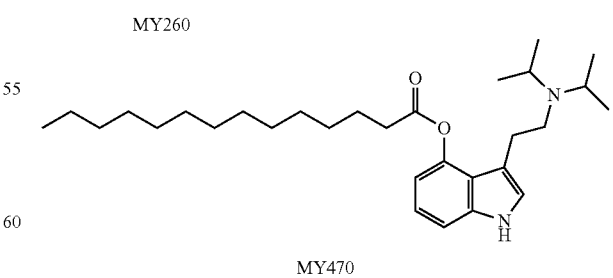

As described in Scheme 7 above, in this embodiment, the present inventors demonstrated the synthesis of the novel psilocin prodrug analog compound MY470, also referred to herein as Formula XII. In this embodiment, to a clear solution of MY260 (0.15 g, 0.57 mmol, 1 eq) in anhydrous DCM (20 mL) at 0-5° C. under nitrogen was added Myristoyl chloride (0.31 g, 1.26 mmol, 2.2 eq) slowly via a syringe. The resultant mixture was allowed to warm to 23±2° C. (RT) and stirred for 16 h, at that temperature. The reaction mixture was analyzed by TLC to check the progress of the reaction and confirm the completion of the reaction (Silica plate, 0.5% concentrated $NH_4OH$ aqueous/5% MeOH in EtOAc). The reaction mixture was quenched with water (10 mL) and saturated $NaHCO_3$ aqueous solution (10 mL), and the layers were separated (organic and aqueous). The DCM layer was dried over $Na_2SO_4$, concentrated under vacuum to get the crude product (oil). The crude oil was purified by silica gel chromatography eluted with 4% (10% $NH_4OH$ aqueous/MeOH) in EtOAc to get a pale yellow oil, which was stored in in −20° C. freezer and obtained 3-(2-(diisopropylamino)ethyl)-1H-indol-4-yl tetradecanoate as off-white solid (0.19 g, yield 90%, Lot #: MNC(06)-4R-7). $^1$H NMR (600 MHz, $CDCl_3$): 8.03 (br s, 1H), 7.23 (d, J=7.8 Hz, 1H), 7.15 (t, J=7.8 Hz, 1H), 7.01 (s, 1H), 6.80 (dd, J=0.6 and 7.8 Hz, 1H), 3.10 (m, 2H), 2.84 (m, 2H), 2.74 (m, 2H), 2.68 (t, J=7.8 Hz, 2H), 1.80-1.85 (m, 2H), 1.45-1.48 (m, 2H), 1.27-1.39 (m, 18H), 1.05 (d, J=7.2 Hz, 12H), 0.91 (t, J=7.2 Hz, 3H). $^{13}$C NMR (150 MHz, $CDCl_3$): 172.8, 144.5, 138.4, 122.0, 121.9, 120.1, 114.1, 112.3, 108.9, 48.4, 46.2, 34.5, 31.9, 29.7, 29.7, 29.6, 29.5, 29.5, 29.4, 29.3, 29.3, 28.2, 24.9, 22.7, 20.9, 14.1. LCMS (ES) m/z calc. for $C_{30}H_{51}N_2O_2$ (M+1)$^+$, 471.40; found, 471.32

Example 9: Novel Pyrrolopyridines and an Imidazopyridine Analogs of Psilocin Having Increase Stability and Oxidation Resistance On one embodiment, the invention include one or more novel Psilocin analogs having increased resistance to oxidation in the presence of by molecular oxygen, among other novel pharmacokinetic properties. As shown above, the compounds of Formulas I-V, VII-VIII, X, and XII describe novel analogs of Psilocin containing one or more N or aza substitutions to their Azaindole groups, and in the case of the compound of Formula V forming and imidazopyridine structure. The carbon to nitrogen replacement in the Psilocin analog may increase oxidation potential such that the degradation by oxygen is inhibited. This can be measured by calculating the HOMO energies of the analog compounds of the invention compared to the parent Psilocin and more specifically by an "average local ionization energy" analysis. The more aza substitutions in the Psilocin analogs may also affect the degree to which glucuronidation occur, which is a major metabolic route of elimination from the body. For example, the analog compounds of the invention according to Formulas I-IV (5-Aza) and Formula V (imidazopyridine) in particular, are predicted to show reduced glucuronidation and therefore slowed excretion. Notably, the analog compounds of the invention may further provide prodrug formulations to enhance oxidative stability.

Example 10. Synthesis of Novel Azatrypamine Isomer

In one embodiment, azatrypamine isomers may be synthesized according to the general scheme 9 provided below. The synthesis of exemplary compound 5 (3-[2-(dimethylamino)ethyl]-1H-pyrrolo[2,3-b]pyridin-4-ol) is illustrative. The core azaindole (Compound 1A) was protected with two benzyl groups to prepare compound 3. This protection at N-1 increase the reactivity at the pyrrole ring at C-3. The protecting group should be electron releasing to provide this reactivity and therefore acylation at N-1 is deactivating. The activated compound 3 is then treated with an acid chloride, here oxalyl chloride is used but other acylhalides work as well. Acylation with oxalyl chloride provides compound 4 with all atoms for the final compound in place. Reduction and deprotection with sodium in liquid ammonia removes both benyzyl groups and reduces the oxalyl group to desired product 5 in low yield. Also formed is the partially reduced amino alcohol 6. This alcohol may be converted to product 5 by further reduction with triethylsilyl hydride in trifluoroacetic acid. Another route to compound 5 includes reduction of compound 4 with lithium aluminum hydride which furnishes the partially reduced compound 7. Protecting group removal with sodium in liquid ammonia produces compound 6 which may be further reacted with triethylsilyl hydride to provide desired azatryptamine 5. In certain embodiments, the invention includes the Compounds and methods for synthesizing them as described in Scheme 10.

Scheme 9

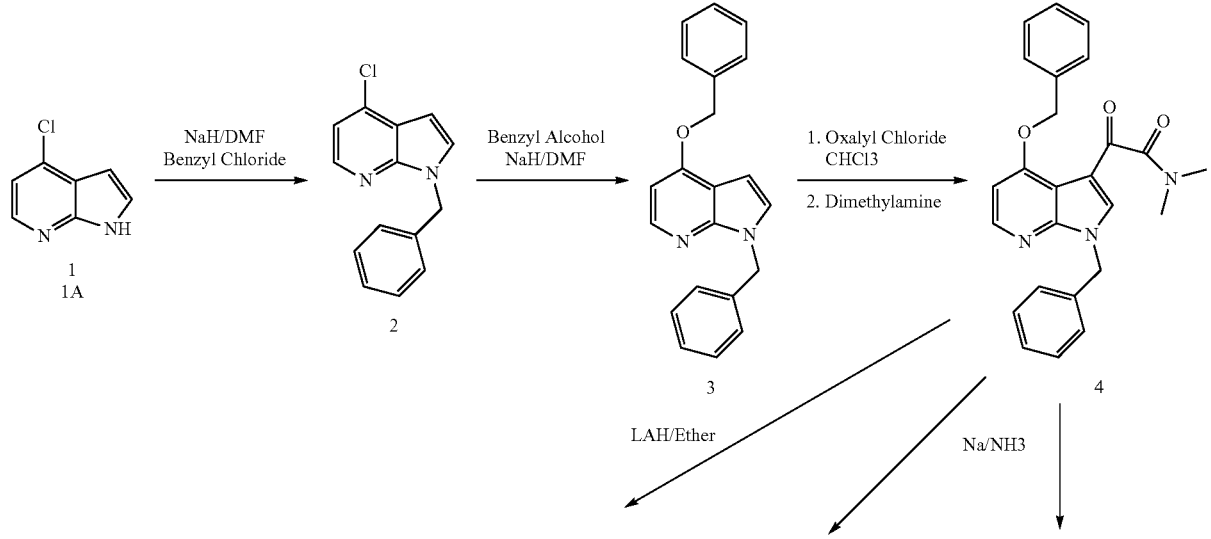

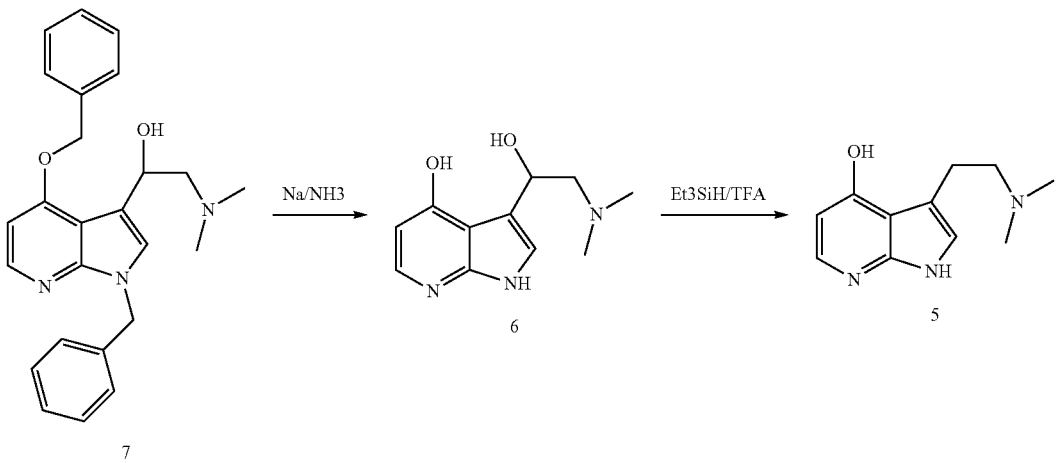

7

Example 11. Step-Wise Synthesis of Novel Azatrypamine Isomers

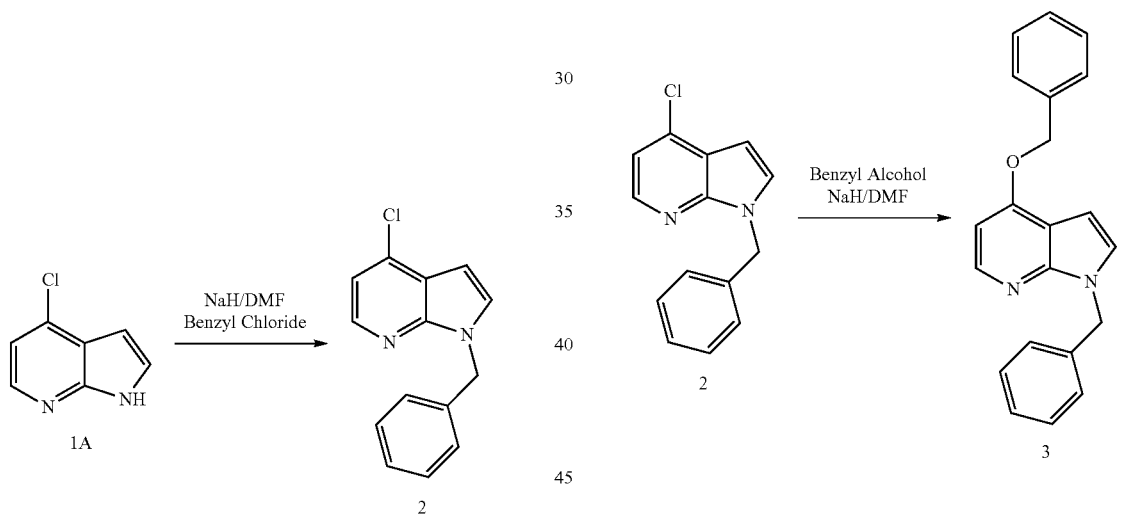

To a suspension of sodium hydride (0.6 g, 25.0 mmol) in N,N-dimethylformamide (25 mL) was added 4-chloro-1H-pyrrolo[2,3-b]pyridine (3.1 g, 20.1 mmol) at 0° C. The suspension was stirred at ambient temperature for 0.5 hours. The mixture was cooled to 0° C. and freshly distilled benzyl chloride (2.8 g, 22.2 mmol) was added. The reaction mixture was allowed to warm to ambient temperature and stirred for 5 hours. The reaction mixture was quenched with ice and extracted with ethyl acetate. The organic layer washed twice with water, brine, and dried over anhydrous sodium sulfate, filtered and concentrated in vacuo. The crude material was purified using flash chromatography (20% ethyl acetate/hexane) to provide 4-chloro-1-((2-(benzyl)-1H-pyrrolo[2,3-b]pyridine as a viscous oil. Yield 4.29 g, 88%.

To a suspension of sodium hydride (1.0 g, 41.4 mmol) in N,N-dimethylformamide (45 mL) was added freshly distilled dry benzyl alcohol (5.4 g, 50.0 mmol) at 0° C. and the suspension was stirred at ambient temperature for 0.5 hours. The mixture was cooled to 0° C. and 4-chloro-1-((2-(benzyl)-1H-pyrrolo[2,3-b]pyridine (4.0 g, 16.5 mmol), Compound 2, was added. The reaction mixture was allowed to warm to ambient temperature and stirred for 12 hours. The reaction mixture was quenched with ice and extracted with ethyl acetate. The organic layer was washed with water, brine and dried over anhydrous sodium sulfate, filtered and concentrated in vacuo. Yield 4.15 g, 80%. LC/MS M+H=315.2. In certain embodiments, the invention includes Compounds 2 and 3 and methods for synthesizing Compounds 2 and 3 as described above.

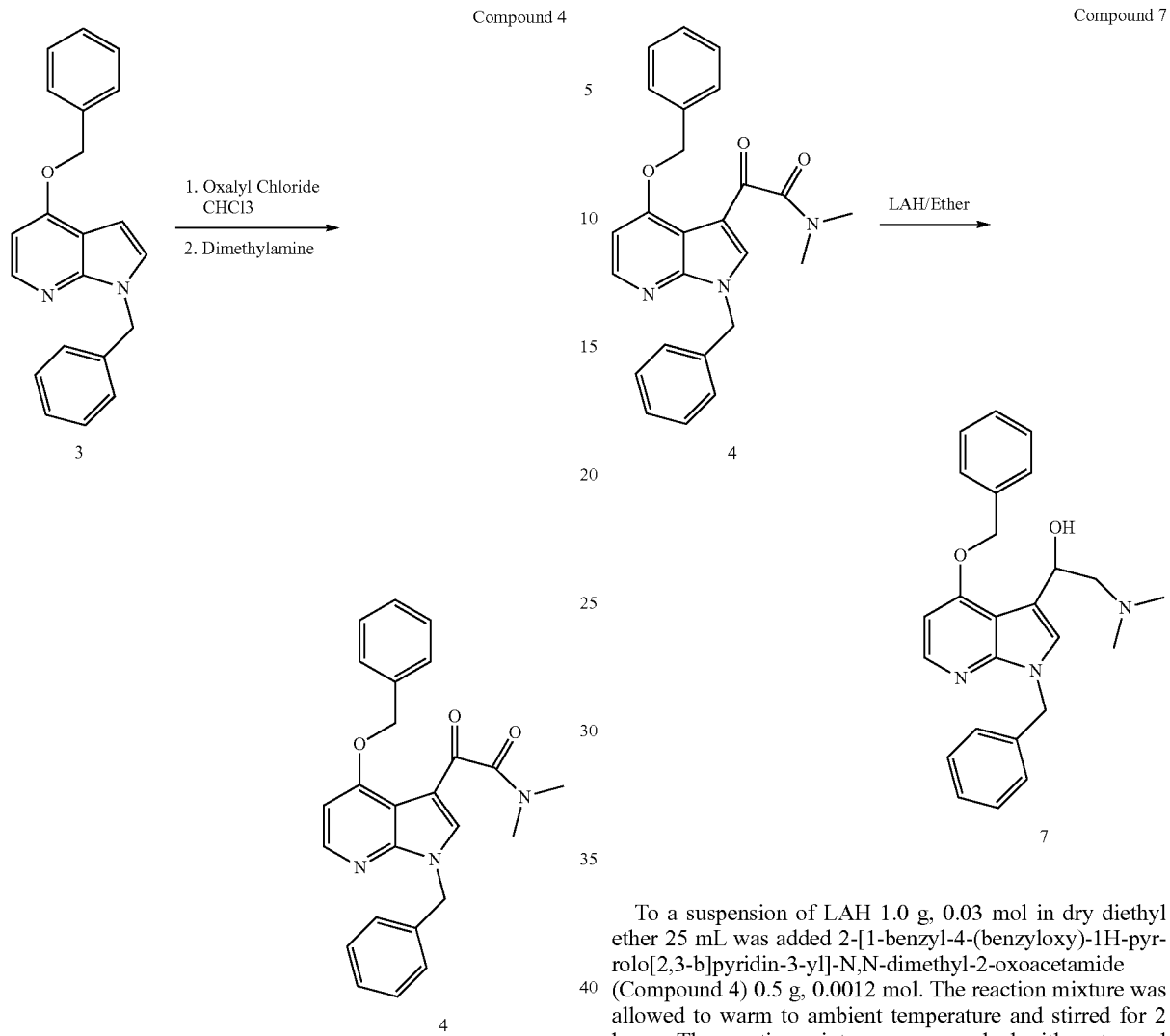

Compound 4

Compound 7

To an ice-cooled solution of 4-benzyl-oxo-1-((2-(benzyl)-1H-pyrrolo[2,3-b]pyridine 0.9 g, Compound 3, (1-benzyl-4-(benzyloxy)-1H-pyrrolo[2,3-b]pyridine) 2.9 mmol in anhydrous CHCl$_3$ (30 ml), oxalyl chloride 0.8 g, 6.3 mmol followed by anhydrous pyridine 1 ml, 13.0 mmol was added. The mixture was allowed to attain room temp. and further stirred for 5 h. The mixture was concentrated under vacuum to remove excess of unreacted oxalyl chloride. The resultant syrup was resuspended in CH$_2$Cl$_2$ (30 ml) and added to excess of cooled dimethylamine solution (40% in H2O). Water was added (100 ml) and aqueous phase was extracted with dichloromethane (20 mL×3), and dried with anhydrous sodium sulfate. The volatiles were removed in vacuo to give a yellow oil. The crude material was purified using flash chromatography (50% ethyl acetate/hexane). White solid. Yield 1.02 g, 86%. LC/MS M+H=414.2. In certain embodiments, the invention includes Compounds 3, and 4 and methods for synthesizing Compounds 3, and 4 as described above.

To a suspension of LAH 1.0 g, 0.03 mol in dry diethyl ether 25 mL was added 2-[1-benzyl-4-(benzyloxy)-1H-pyrrolo[2,3-b]pyridin-3-yl]-N,N-dimethyl-2-oxoacetamide (Compound 4) 0.5 g, 0.0012 mol. The reaction mixture was allowed to warm to ambient temperature and stirred for 2 hours. The reaction mixture was quenched with water and filtered. The organic layer dried over anhydrous sodium sulfate, filtered and concentrated in vacuo. LC/MS M+H=402.2 In certain embodiments, the invention includes Compound 7 and methods for synthesizing Compound 7 as described above.

Compound 5

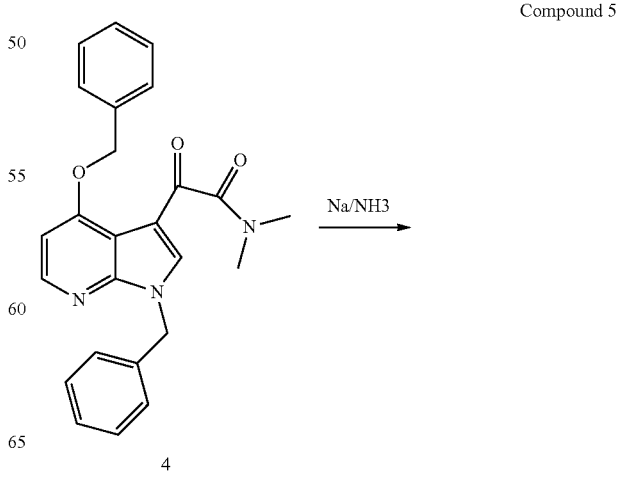

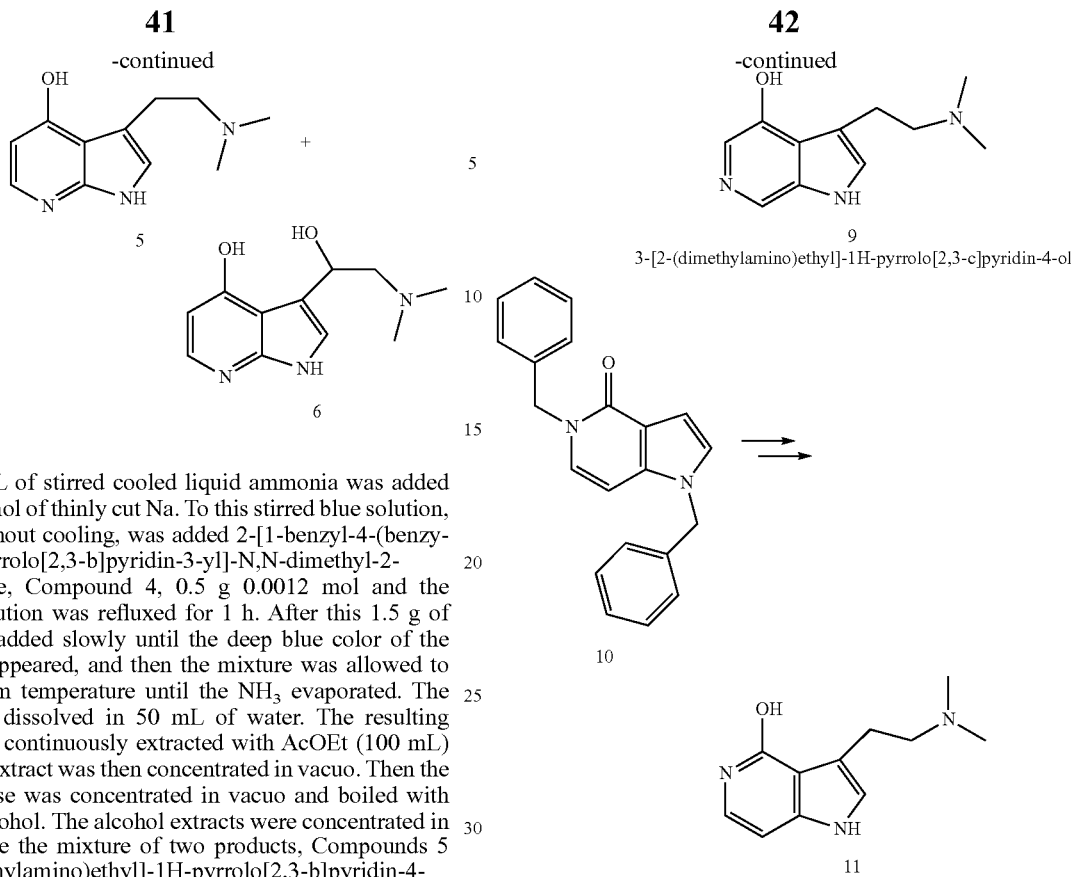

To 100 mL of stirred cooled liquid ammonia was added 0.5 g 0.022 mol of thinly cut Na. To this stirred blue solution, after 1 h without cooling, was added 2-[1-benzyl-4-(benzyloxy)-1H-pyrrolo[2,3-b]pyridin-3-yl]-N,N-dimethyl-2-oxoacetamide, Compound 4, 0.5 g 0.0012 mol and the resulting solution was refluxed for 1 h. After this 1.5 g of NH₄Cl was added slowly until the deep blue color of the solution disappeared, and then the mixture was allowed to stand at room temperature until the NH$_3$ evaporated. The residue was dissolved in 50 mL of water. The resulting solution was continuously extracted with AcOEt (100 mL) for 2 h. The extract was then concentrated in vacuo. Then the aqueous phase was concentrated in vacuo and boiled with isopropyl alcohol. The alcohol extracts were concentrated in vacuo to give the mixture of two products, Compounds 5 (3-[2-(dimethylamino)ethyl]-1H-pyrrolo[2,3-b]pyridin-4-ol) (LC/MS M+H=206.2) in low yield and partially reduced Compound 6 (LC/MS M+H=222.2). The partially reduced Compound 6 may be further converted to Compound 5 by reduction with triethylsilane in trifluoracetic acid. In certain embodiments, the invention includes Compounds 4, 5, and 6 and methods for synthesizing Compounds 4, 5, and 6 as described above.

Example 12. Step-Wise Synthesis of Novel Aza Analogs

In an analogous manner Compounds 8 and 10 as shown below may be prepared and converted to their respective Compounds 9 and 11 (Scheme 10).

Scheme 10. Preparation of 5 and 6-Aza analogs.

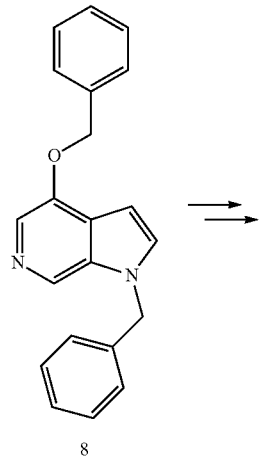

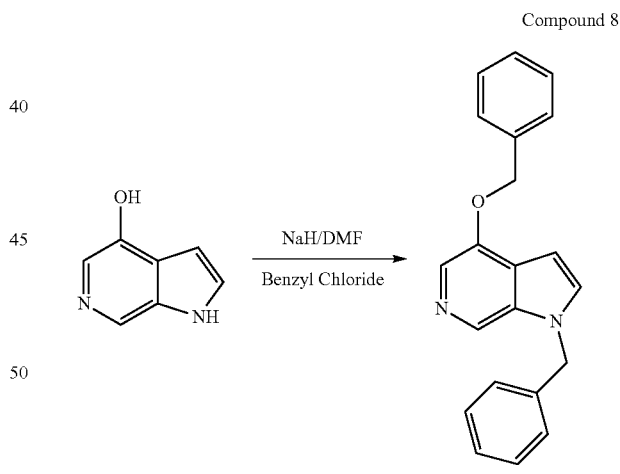

To a suspension of sodium hydride (156 mg, 0.0065 mol) in N,N-dimethylformamide (25 mL) was added 1H-pyrrolo[2,3-c]pyridine-4-ol (400 mg, 0.003 mmol) and freshly distilled dry benzyl chloride (0.76 g, 0.006 mol) at 0° C. The reaction mixture was allowed to warm to ambient temperature and stirred for 12 hours. The reaction mixture was quenched with ice and extracted with ethyl acetate. The organic layer was washed with water, brine and dried over anhydrous sodium sulfate, filtered and concentrated in vacuo. The crude material was purified using flash chromatography (20% ethyl acetate/hexane). Yield 410 mg, 44%, Compound 8 (1-benzyl-4-(benzyloxy)-1H-pyrrolo[2,3-c]pyridine). LC/MS M+H=315.2. In certain embodiments, the invention includes Compounds 8, 9, 10, and 11 and methods for synthesizing Compounds 8, 9, 10, and 11 as described above. In other embodiments, according to the following scheme:

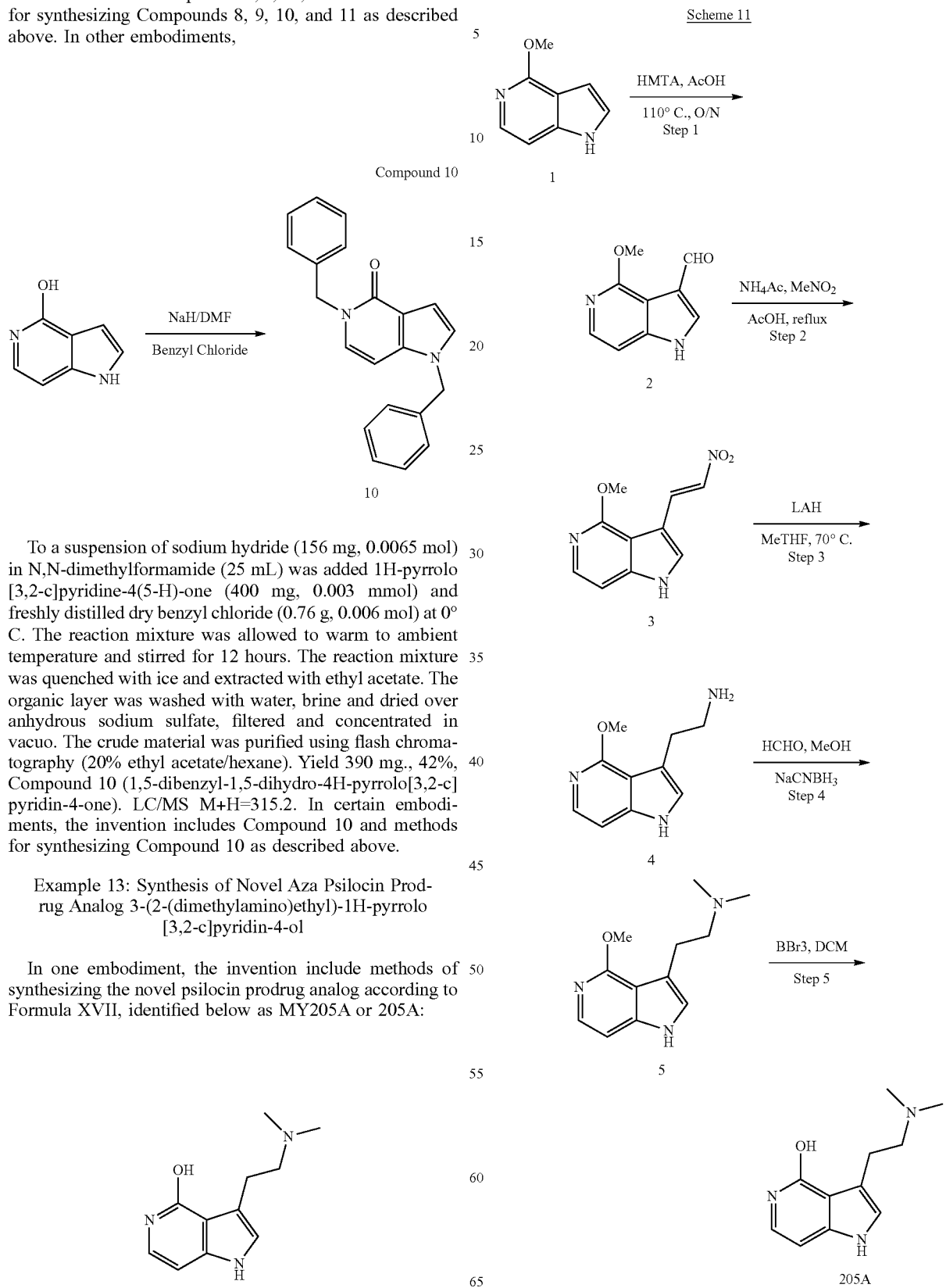

To a suspension of sodium hydride (156 mg, 0.0065 mol) in N,N-dimethylformamide (25 mL) was added 1H-pyrrolo[3,2-c]pyridine-4(5-H)-one (400 mg, 0.003 mmol) and freshly distilled dry benzyl chloride (0.76 g, 0.006 mol) at 0° C. The reaction mixture was allowed to warm to ambient temperature and stirred for 12 hours. The reaction mixture was quenched with ice and extracted with ethyl acetate. The organic layer was washed with water, brine and dried over anhydrous sodium sulfate, filtered and concentrated in vacuo. The crude material was purified using flash chromatography (20% ethyl acetate/hexane). Yield 390 mg., 42%, Compound 10 (1,5-dibenzyl-1,5-dihydro-4H-pyrrolo[3,2-c]pyridin-4-one). LC/MS M+H=315.2. In certain embodiments, the invention includes Compound 10 and methods for synthesizing Compound 10 as described above.

Example 13: Synthesis of Novel Aza Psilocin Prodrug Analog 3-(2-(dimethylamino)ethyl)-1H-pyrrolo[3,2-c]pyridin-4-ol In one embodiment, the invention include methods of synthesizing the novel psilocin prodrug analog according to Formula XVII, identified below as MY205A or 205A:

Synthesis of Novel Psilocin Prodrug Analog Intermediate 4-methoxy-1H-pyrrolo[3,2-c]pyridine-3-carbaldehyde (2)

As described in Scheme 11 above, in this embodiment, the present inventors demonstrated the synthesis of the novel psilocin prodrug analog intermediate compound 2. In this embodiment, to a stirred suspension of 4-methoxy-1H-pyrrolo[3,2-c]pyridine 1 (2.6 g, 17.0 mmol, 1.0 eq) in acetic acid (15 mL) and water (15 mL) was added hexamethylenetetramine (2.5 g, 17.0 mmol, 1.0 eq). The resultant mixture was stirred and heated at 90° C. for 15 hours. TLC indicated the reaction was completed. The reaction mixture was neutralized with NaOH to pH=7, extracted with 10% MeOH in EtOAc and concentrated under vacuum to afford the residue, which was purified by chromatography (silica gel, 10% MeOH in DCM) to provide compound 2 (0.72 g, 24% yield, Lot #: MNC-4R-94) as yellow solid. $^1$H NMR (600 MHz, CDCl$_3$): δ 12.51 (br s, 1H), 10.26 (s, 1H), 8.14 (s, 1H), 7.80 (d, J=6.0 Hz, 1H), 7.16 (d, J=6.0 Hz, 1H), 4.06 (s, 3H).

Synthesis of 4-methoxy-3-(2-nitrovinyl)-1H-pyrrolo[3,2-c]pyridine (3)

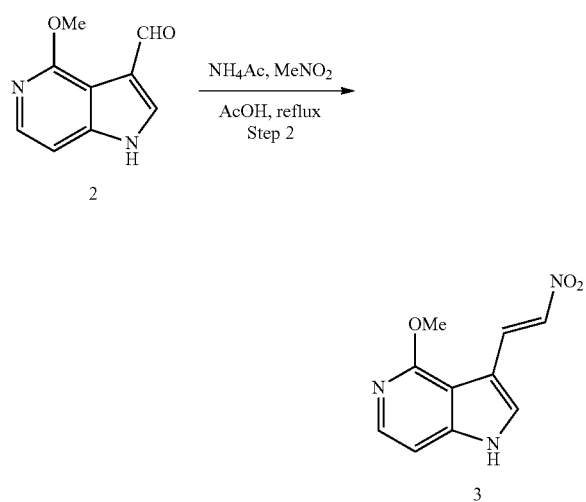

As described in Scheme 11 above, in this embodiment, the present inventors demonstrated the synthesis of the novel psilocin prodrug analog intermediate compound 3. In this embodiment, to a suspension of 2 (0.72 g, 4.1 mmol, 1.0 eq) in acetic acid (4.5 mL) was added nitromethane (1.4 mL, 28.7 mmol, 7.0 eq) followed by ammonium acetate (0.38 g, 4.9 mmol, 1.2 eq). The resultant mixture was stirred and heated at 100° C. for 1.5 h and TLC indicated that the reaction was completed. The reaction mixture was cooled to room temperature, quenched with water, stirred for 2h, filtered and died to provide compound 3 (0.60 g, 67% yield, Lot #: MNC-4R-95) as yellow solid. $^1$H NMR (600 MHz, DMSO-d$_6$): d 12.47 (br s, 1H), 8.45 (d, J=13.2 Hz, 1H), 8.28 (s, 1H), 8.21 (d, J=13.2 Hz, 1H), 7.89 (d, J=6.0 Hz, 1H), 7.15 (d, J=6.0 Hz, 1H), 4.06 (s, 3H).

Synthesis of 2-(4-methoxy-1H-pyrrolo[3,2-c]pyridin-3-yl)-N,N-dimethylethanamine

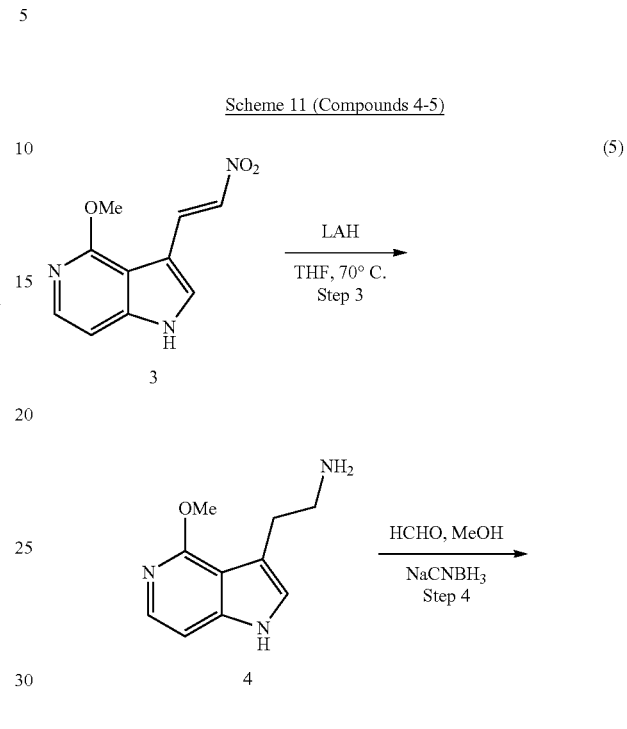

As described in Scheme 11 above, in this embodiment, the present inventors demonstrated the synthesis of the novel psilocin prodrug analog intermediate compounds 4-5. In this embodiment, to a stirred solution of compound 3 (0.60 g, 2.74 mmol, 1.0 eq) in THF (anhydrous, 200 mL) under nitrogen at 0° C. to 5° C. was added LAH (1M in THF, 16.5 mL, 16.4 mmol, 6.0 eq) slowly via a syringe. The resulting yellow suspension was stirred at 70° C. for 16 hours. After cooling to 0° C. to 5° C., the reaction was quenched with water and NaOH, filtered and concentrated to provide colorless oil (0.54 g). To this oil in MeOH (30 mL) was added HCHO (4.5 mL), HOAc (0.63 mL) and NaCNBH3 (0.86 g) in portions. The mixture was stirred at rt for 1.5 h and concentrated to provide the residue, which was purified by chromatography (silica gel, DCM/MeOH/NH4OH=8/1/0.1) to provide compound 5 (0.47 g, 78% yield, Lot #: MNC-4R-103) as a colorless oil. $^1$H NMR (600 MHz, CDCl$_3$): δ 8.29 (s, 1H), 7.71 (d, J=6.0 Hz, 1H), 6.81 (s, 1H), 6.79 (d, J=6.0 Hz, 1H), 4.00 (s, 1H), 2.99 (m, 2H), 2.58 (m, 2H), 2.29 (s, 6H).

Synthesis of 3-(2-(dimethylamino)ethyl)-1H-pyrrolo[3,2-c]pyridin-4-ol (205A)

according to the following scheme:

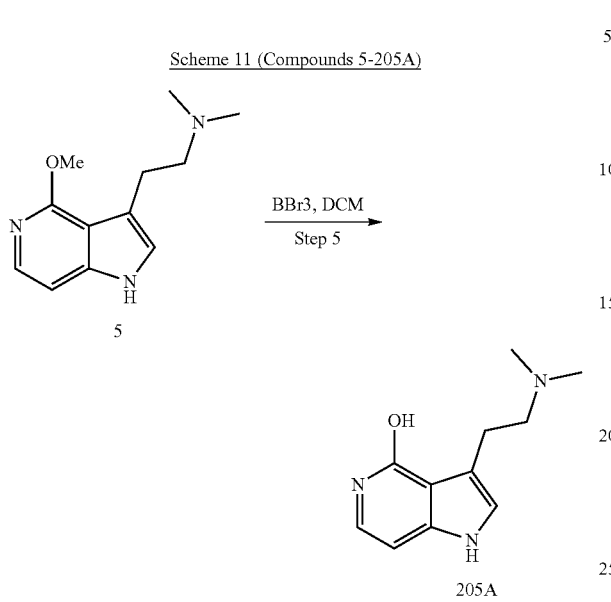

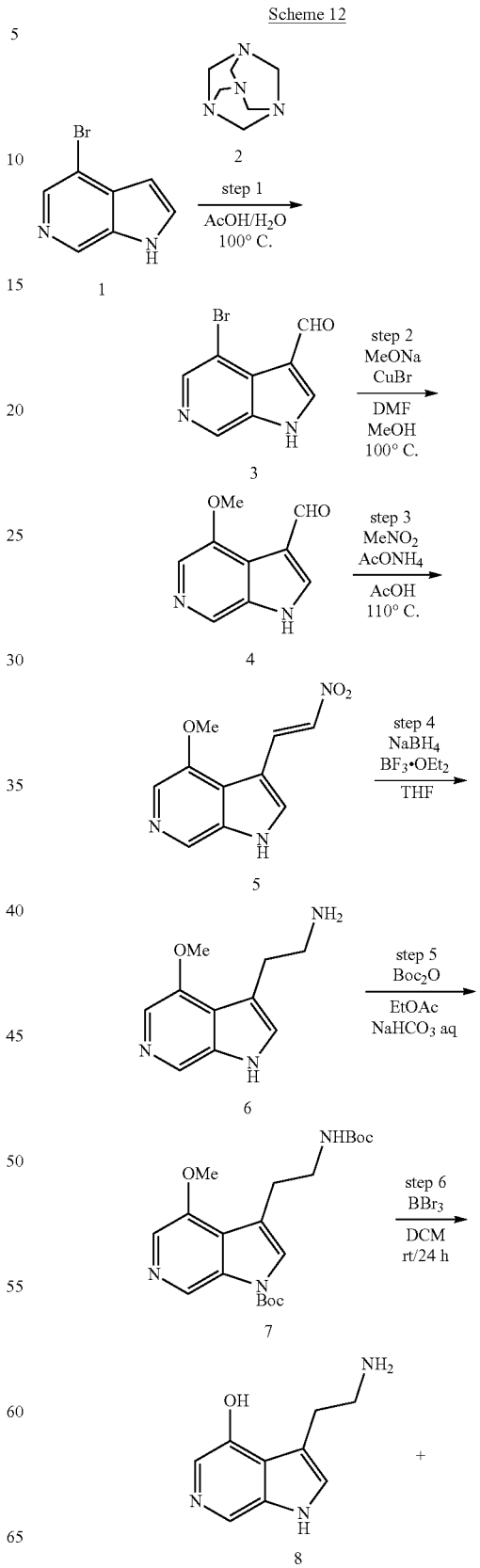

As described in Scheme 11 above, in this embodiment, the present inventors demonstrated the synthesis of the novel psilocin prodrug analog compound 205A (also described herein as MY205A, and Formula XVII). In this embodiment, a solution of 5 (0.11 g, 0.50 mmol) in dichloroethane (4 mL) under nitrogen was added boron tribromide (0.4 mL) slowly via a syringe. The resultant suspension was stirred at 0° C. to room temperature for 24 hours. After cooling to 0° C. to 5° C., the reaction mixture was quenched by adding MeOH and concentrated under vacuum to give a residue, which was purified by chromatography (silica gel, DCM/MeOH/NH4OH=5/1/0.1) to provide compound MY205A (0.065 g, 63% yield, Lot #: MNC-4R-102-1) as off-white solid. $^1$H NMR (600 MHz, CH$_3$OD): d 7.02 (d, J=7.2 Hz, 1H), 6.96 (s, 1H), 6.52 (d, J=7.2 Hz, 1H), 3.34 (t, J=7.2 Hz, 2H), 3.13 (t, J=7.2 Hz, 2H), 2.82 (s, 6H). $^{13}$C NMR (150 MHz, DMSO-d$_6$): δ 160.96, 140.25, 127.91, 121.23, 115.26, 113.33, 96.21, 58.63, 42.93, 21.51. LCMS (ES) m/z calc. for C$_{11}$H$_{16}$N$_3$O (M+1)$^+$, 206.1; found, 206.0

Example 14: Synthesis of Novel Aza Analog 3-(2-(dimethylamino)ethyl)-1H-pyrrolo[2,3-c]pyridin-4-ol As shown in Scheme 12 below, the present invention provides for the step wise production of novel Aza analog 3-(2-(dimethylamino)ethyl)-1H-pyrrolo[2,3-c]pyridin-4-ol also referred to herein as MY205B and Formula XVIII:

-continued

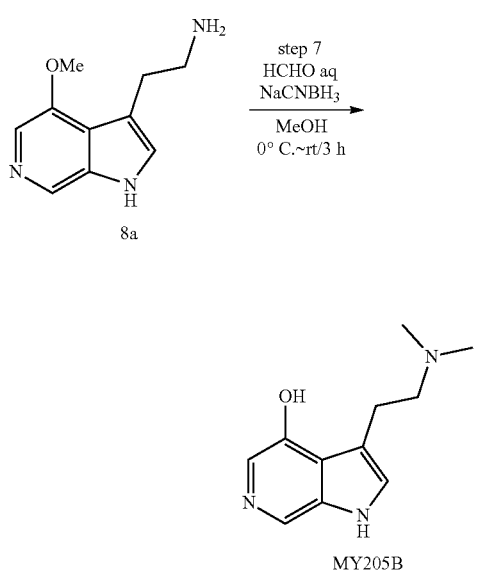

8a

Synthesis of 4-bromo-1H-pyrrolo[2,3-c]pyridine-3-carbaldehyde (3)

Scheme 12 (Compounds 1-3)

As described in Scheme 12 above, in this embodiment, the present inventors demonstrated the synthesis of the novel psilocin prodrug analog intermediate compounds 2-3. In this embodiment, to a stirred suspension of 4-bromo-1H-pyrrolo[2,3-c]pyridine 1 (2.0 g, 10.15 mmol, 1 eq) in acetic acid (15 mL) and water (15 mL) was added hexamethylenetetramine 2 (2.19 g, 15.33 mmol, 1.5 eq). The resultant mixture was stirred and heated at 100° C. for 16 hours. TLC indicated the reaction was completed. The reaction mixture was concentrated under vacuum to remove solvents. The residue was dissolved in ethyl acetate (100 mL), washed with sat. sodium bicarbonate (NaHCO$_3$) aqueous (100 mL×2), brine (100 mL×1), dried over sodium sulphate (Na$_2$SO$_4$), concentrated under vacuum to afford the crude 4-bromo-1H-pyrrolo[2,3-c]pyridine-3-carbaldehyde 3 (1.50 g, yield: 65%) as yellow solid which was used for next step without further purification. $^1$H NMR (600 MHz, DMSO-d$_6$): δ 13.00 (br s, 1H), 10.61 (s, 1H), 8.87 (s, 1H), 8.53 (s, 1H), 8.47 (s, 1H).

Synthesis of 4-methoxy-1H-pyrrolo[2,3-c]pyridine-3-carbaldehyde (4)

Scheme 12 (Compounds 3-4)

As described in Scheme 12 above, in this embodiment, the present inventors demonstrated the synthesis of the novel psilocin prodrug analog intermediate compound 4. In this embodiment, to a suspension of 3 (1.50 g, 6.66 mmol, 1 eq), cupper (I) bromide (1.76 g, 12.27 mmol, 1.8 eq) in dimethylformamide (anhydrous, 40 mL) and methanol (25 mL) was added sodium methoxide solid (15.0 g, 277.7 mmol, 41.6 eq) in portions. The resultant mixture was stirred and heated at 100° C. for 1.5 hours and TLC indicated that the reaction was completed. The reaction mixture was cooled to room temperature, poured into ice-water (400 mL), and extracted with ethyl acetate (100 mL×3). The combined organic layer was washed with brine (100 mL×1), dried over Na$_2$SO$_4$, and concentrated under vacuum to give a crude solid. The crude was purified by silica gel column chromatography eluting with 1% conc. ammonium hydroxide aqueous/10% methanol/ethyl acetate to afford the product 4-methoxy-1H-pyrrolo[2,3-c]pyridine-3-carbaldehyde 4 (0.60 g, yield 51%) as yellow solid. $^1$H NMR (600 MHz, DMSO-d$_6$): δ 12.73 (br s, 1H), 10.32 (s, 1H), 8.59 (s, 1H), 8.32 (s, 1H), 8.11 (s, 1H), 4.09 (s, 3H).

Synthesis of (E)-4-methoxy-3-(2-nitrovinyl)-1H-pyrrolo[2,3-c]pyridine (5)

Scheme 12 (Compounds 4-5)

As described in Scheme 12 above, in this embodiment, the present inventors demonstrated the synthesis of the novel psilocin prodrug analog intermediate compound 5. In this embodiment, to a suspension of 4 (0.6 g, 3.4 mmol, 1 eq) in acetic acid (20 mL) was added nitromethane (1.0 mL, 18.3 mmol, 5.4 eq) followed by ammonium acetate (0.54 g, 7.0 mmol, 2.05 eq). The resultant mixture was stirred and heated at 100° C. for 3 hours and TLC indicated that the reaction was completed. The reaction mixture was cooled to room temperature and concentrated under vacuum to give a crude yellow solid. The crude solid was suspended in water (10 mL), neutralized to pH 7 to 8 with sat. NaHCO$_3$ aqueous, stirred at room temperature for 1 hour, filtered, washed with water (10 mL×3), dried in air to give product (E)-4-methoxy-3-(2-nitrovinyl)-1H-pyrrolo[2,3-c]pyridine 5 (0.64 g, yield 85%) as yellow solid. $^1$H NMR (600 MHz, DMSO-d$_6$): δ 12.69 (br s, 1H), 8.58 (s, 1H), 8.54 (d, J=13.2 Hz, 1H), 8.48 (s, 1H), 8.20 (d, J=13.2 Hz, 1H), 8.08 (s, 1H), 4.11 (s, 3H). LCMS (ES) m/z calc. for $C_{10}H_{10}N_3O_3$ [M+1]$^+$, 220.07; found, 219.96

Synthesis of tert-butyl 3-(2-((tert-butoxycarbonyl)amino)ethyl)-4-methoxy-1H-pyrrolo[2,3-c]pyridine-1-carboxylate (7)

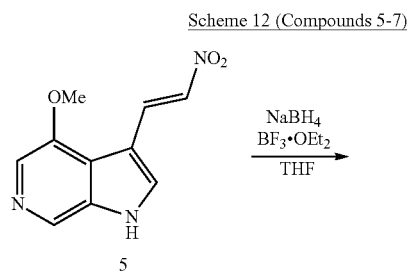

Scheme 12 (Compounds 5-7)

7 to 8 with sat. NaHCO$_3$ aqueous, diluted with THF (20 mL) and ethyl acetate (20 mL), and di-tert-butyl dicarbonate (Boc$_2$O) (1.6 g, 7.3 mmol, 2.5 eq) was added. After stirred at room temperature for 1 hour, another portion of Boc$_2$O (1.6 g, 7.3 mmol, 2.5 eq) was added. The reaction mixture was stirred at room temperature for 16 hours, the layers were separated. The aqueous layer was extracted with ethyl acetate (30 mL×2). The combined organic layers were washed with brine (100 mL×1), dried over Na$_2$SO$_4$, and concentrated under vacuum to give a crude solid. The crude was purified by silica gel column chromatography eluting with hexanes/ethyl acetate (3:1 to 1:2) to afford the product tert-butyl 3-(2-((tert-butoxycarbonyl)amino)ethyl)-4-methoxy-1H-pyrrolo[2,3-c]pyridine-1-carboxylate 7 (0.74 g, yield 64%) as white solid. $^1$H NMR (600 MHz, CDCl$_3$): δ 8.99 (s, 1H), 7.94 (s, 1H), 7.34 (s, 1H), 4.64 (br s, 1H), 3.94 (s, 3H), 3.36-3.37 (m, 2H), 2.91-2.93 (m, 2H), 1.61 (s, 9H), 1.34 (s, 9H). LCMS (ES) m/z calc. for $C_{20}H_{30}N_3O_5$ [M+1]$^+$, 392.22; found, 392.19

Synthesis of 3-(2-aminoethyl)-1H-pyrrolo[2,3-c]pyridin-4-ol (8)

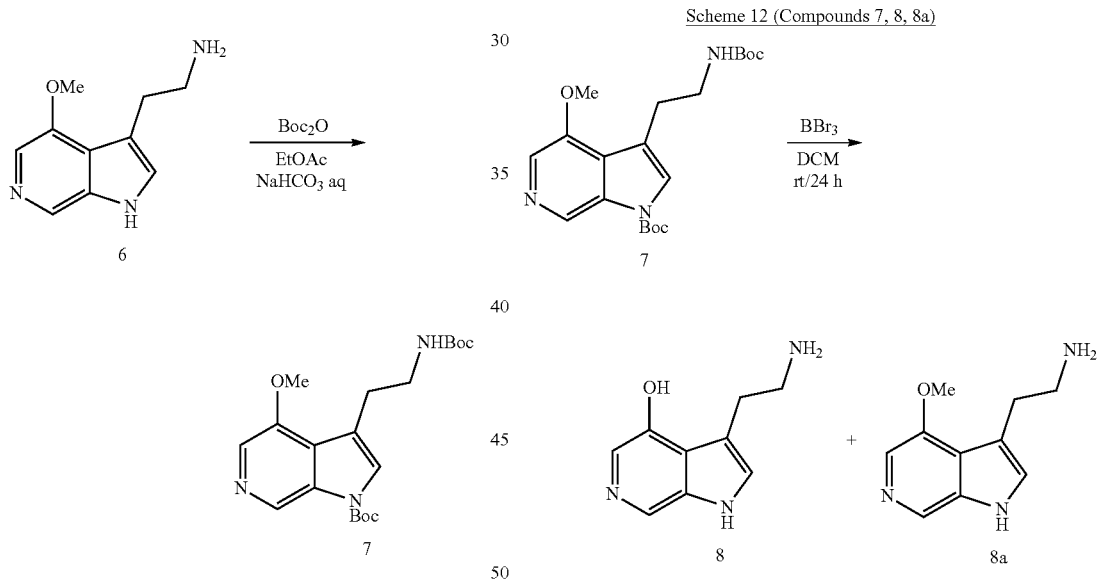

Scheme 12 (Compounds 7, 8, 8a)

As described in Scheme 12 above, in this embodiment, the present inventors demonstrated the synthesis of the novel psilocin prodrug analog intermediate compounds 6-7. In this embodiment, to a stirred suspension of sodium borohydride (0.9 g, 23.8 mmol, 8.1 eq) in THF (anhydrous, 50 mL) under nitrogen at 0° C. to 5° C. was added boron trifluoride diethyl etherate (3.5 mL, 28.3 mmol, 9.7 eq) slowly via a syringe. After stirred for 15 minutes, solid 5 was added in portions over a period of 5 minutes. The resultant mixture was stirred at 0° C. to 5° C. for 0.5 hour and heated slowly to 65° C. and keep at that temperature for 16 hours. After cooling to 0° C. to 5° C., water (5 mL) was added slowly to quench the reaction, and 2 N HCl aqueous (100 mL) was then added. The reaction mixture was heated to reflux and kept reflux for 2 hours, concentrated under vacuum to remove solvents. The residue was suspended in water (10 mL), neutralized to pH As described in Scheme 12 above, in this embodiment, the present inventors demonstrated the synthesis of the novel psilocin prodrug analog intermediate compound 8. In this embodiment, to a solution of 7 (0.74 g, 1.89 mmol, 1 eq) in dichloromethane (DCM) (anhydrous, 40 mL) at 0° C. to 5° C. under nitrogen was added boron tribromide (4.0 mL, 41.5 mmol, 21.9 eq) slowly via a syringe. The resultant suspension was stirred at 0° C. to room temperature for 24 hours. After cooling to 0° C. to 5° C., the reaction mixture was quenched by adding cold water (10 mL) slowly and neutralized to pH 7 to 8 by 10% sodium hydroxide aqueous. The reaction mixture was stirred for 0.5 hour, concentrated under vacuum to dry to give a crude solid (3 g, with inorganic salt) which was used for next step without further purification. The $^1$HNMR indicated that the product was a mixture of 8 and 8a (ratio~3:2).

Synthesis of 3-(2-(dimethylamino)ethyl)-1H-pyrrolo[2,3-c]pyridin-4-ol (MY205B)

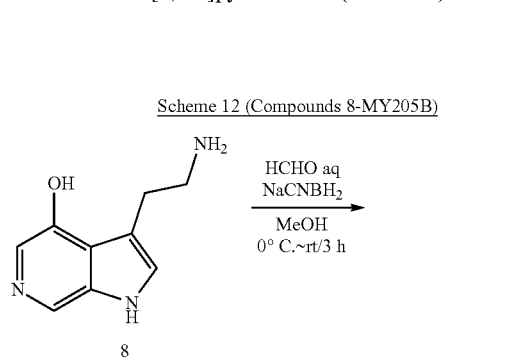

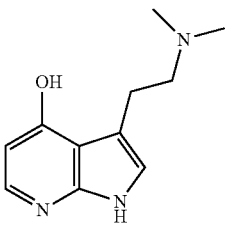

according to the following scheme:

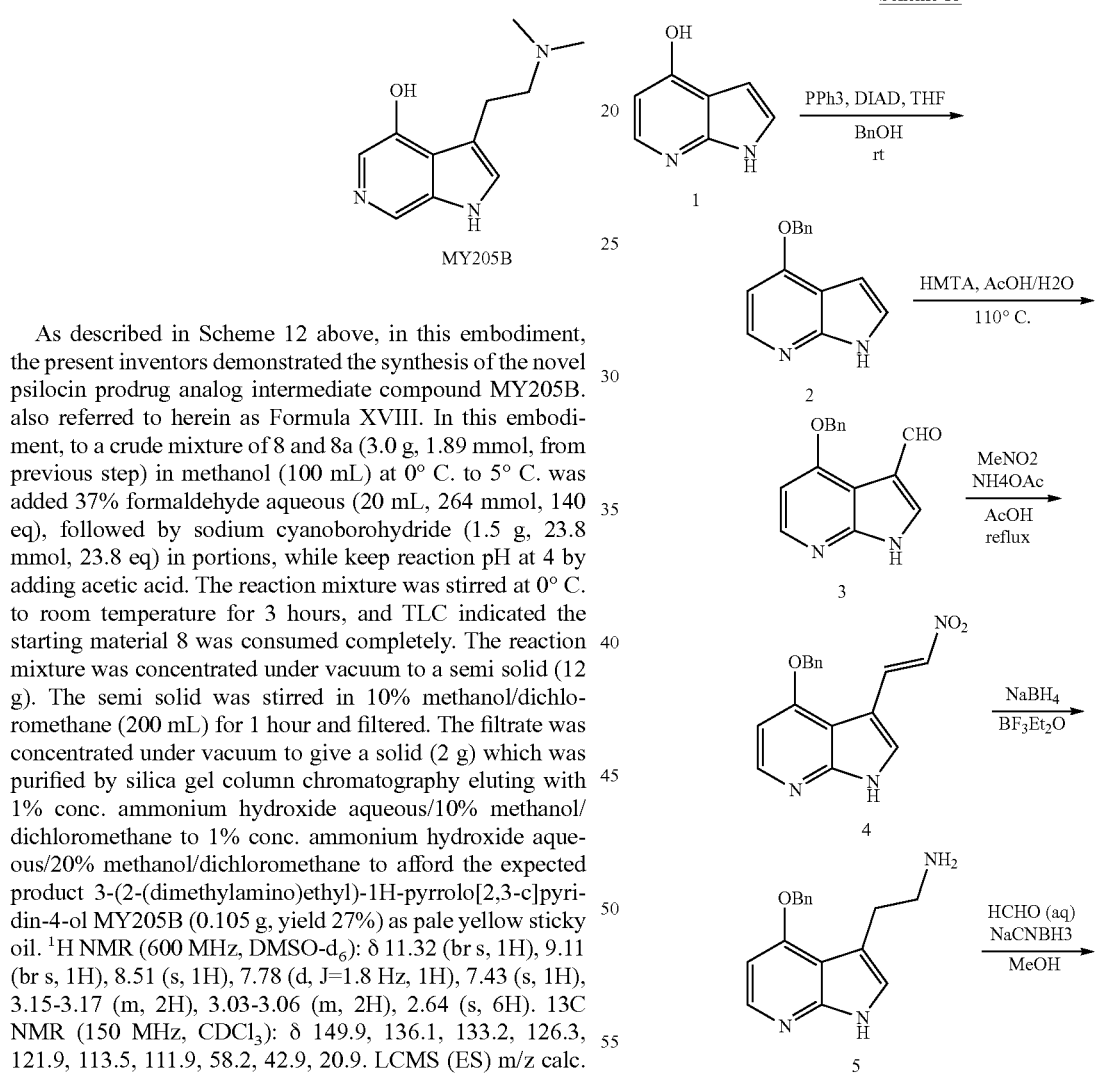

As described in Scheme 12 above, in this embodiment, the present inventors demonstrated the synthesis of the novel psilocin prodrug analog intermediate compound MY205B. also referred to herein as Formula XVIII. In this embodiment, to a crude mixture of 8 and 8a (3.0 g, 1.89 mmol, from previous step) in methanol (100 mL) at 0° C. to 5° C. was added 37% formaldehyde aqueous (20 mL, 264 mmol, 140 eq), followed by sodium cyanoborohydride (1.5 g, 23.8 mmol, 23.8 eq) in portions, while keep reaction pH at 4 by adding acetic acid. The reaction mixture was stirred at 0° C. to room temperature for 3 hours, and TLC indicated the starting material 8 was consumed completely. The reaction mixture was concentrated under vacuum to a semi solid (12 g). The semi solid was stirred in 10% methanol/dichloromethane (200 mL) for 1 hour and filtered. The filtrate was concentrated under vacuum to give a solid (2 g) which was purified by silica gel column chromatography eluting with 1% conc. ammonium hydroxide aqueous/10% methanol/dichloromethane to 1% conc. ammonium hydroxide aqueous/20% methanol/dichloromethane to afford the expected product 3-(2-(dimethylamino)ethyl)-1H-pyrrolo[2,3-c]pyridin-4-ol MY205B (0.105 g, yield 27%) as pale yellow sticky oil. $^1$H NMR (600 MHz, DMSO-$d_6$): δ 11.32 (br s, 1H), 9.11 (br s, 1H), 8.51 (s, 1H), 7.78 (d, J=1.8 Hz, 1H), 7.43 (s, 1H), 3.15-3.17 (m, 2H), 3.03-3.06 (m, 2H), 2.64 (s, 6H). 13C NMR (150 MHz, CDCl$_3$): δ 149.9, 136.1, 133.2, 126.3, 121.9, 113.5, 111.9, 58.2, 42.9, 20.9. LCMS (ES) m/z calc. for $C_{11}H_{16}N_3O$ [M+1]$^+$, 206.13; found, 206.01

Example 15: Synthesis of Novel Aza Analog 3-(2-(dimethylamino)ethyl)-1H-pyrrolo[2,3-b]pyridin-4-ol As shown in Scheme 13 below, the present invention provides for the step wise production of novel Aza analog 3-(2-(dimethylamino)ethyl)-1H-pyrrolo[2,3-c]pyridin-4-ol also referred to herein as MY205C and Formula XIX:

δ 12.74 (br s, 1H), 10.19 (s, 1H), 8.23 (d, J=5.4 Hz, 1H), 8.17 (s, 1H), 7.53 (m, 2H), 7.44 (m, 2H), 7.36 (m, 1H), 7.00 (d, J=5.4 Hz, 1H), 5.40 (s, 2H).

Synthesis of 4-(benzyloxy)-3-(2-nitrovinyl)-1H-pyrrolo[2,3-b]pyridine (4)

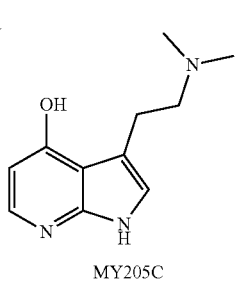

MY205C

Synthesis of 4-(benzyloxy)-1H-pyrrolo[2,3-b]pyridine (2)

Scheme 13 (Compounds 3-4)

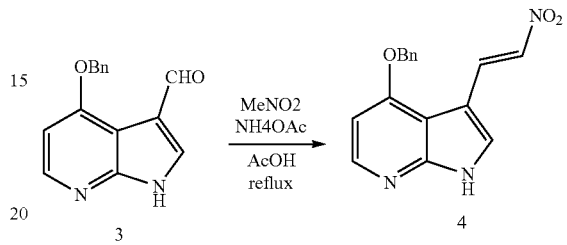

Scheme 13 (Compounds 1-2)

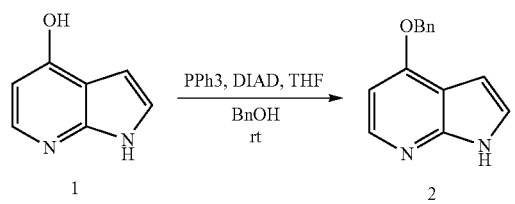

As described in Scheme 13 above, in this embodiment, the present inventors demonstrated the synthesis of the novel psilocin prodrug analog intermediate compound 2. In this embodiment, to a stirred solution of PPh3 (17.5 g, 67.0 mmol, 2.0 eq) in THF (100 mL) was added DIAD (11.7 g, 67.0 mmol, 2.0 eq) at 5° C. The resultant mixture was added to a solution of compound 1 (4.5 g, 33.5 mmol, 1.0 eq) and benzyl alcohol (4.2 mL, 40.2 mmol, 1.2 eq) in THF (200 mL). The mixture was stirred for 3 h, concentrated, washed with EtOAc/Hexanes (1:2, 300 mL) and filtrated to provide 28 g yellow solid as a mixture of 2 and TPPO, which was used in the next step without further purification.

Synthesis of 4-(benzyloxy)-1H-pyrrolo[2,3-b]pyridine-3-carbaldehyde (3)

As described in Scheme 13 above, in this embodiment, the present inventors demonstrated the synthesis of the novel psilocin prodrug analog intermediate compound 4. In this embodiment, to a suspension of 3 (2.24 g, 8.23 mmol, 1.0 eq) in acetic acid (30 mL) was added nitromethane (2.24 mL, 41.15 mmol, 5.0 eq) followed by ammonium acetate (0.63 g, 8.23 mmol, 1.0 eq). The resultant mixture was stirred and heated at 125° C. for 4 h and TLC indicated that the reaction was complete. The reaction mixture was cooled to room temperature, quenched with water, stirred for 0.5 h, filtered and died to provide compound 4 (2.45 g, 94% yield, Lot #: MNC-4R-41) as yellow solid. $^1$H NMR (600 MHz, DMSO-$d_6$): δ 12.66 (br s, 1H), 8.44 (d, J=13.2 Hz, 1H), 8.32 (s, 1H), 8.24 (d, J=5.4 Hz, 1H), 8.06 (d, J=13.2 Hz, 1H), 7.57 (m, 2H), 7.46 (m, 2H), 7.40 (m, 1H), 7.00 (d, J=5.4 Hz, 1H), 5.41 (s, 2H).

Synthesis of 2-(4-(benzyloxy)-1H-pyrrolo[2,3-b]pyridin-3-yl)-N,N dimethylethanamine (6)

Scheme 13 (Compounds 2-3)

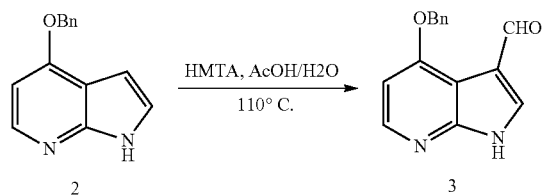

As described in Scheme 13 above, in this embodiment, the present inventors demonstrated the synthesis of the novel psilocin prodrug analog intermediate compound 3. In this embodiment, to a stirred suspension of crude compound 2 (28 g) in acetic acid (28 mL) and water (28 mL) was added hexamethylenetetramine (4.7 g, 33.5 mmol, 1.0 eq). The resultant mixture was stirred and heated at 110° C. for 16 hours. The reaction mixture was filtered to provide compound 3 (2.24 g, 24% yield in 2 steps, Lot #: MNC-4R-39, 40) as light-yellow solid. $^1$H NMR (600 MHz, DMSO-$d_6$):

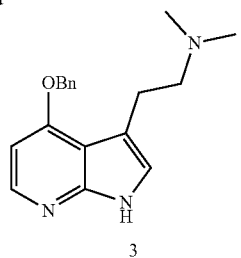

3

As described in Scheme 13 above, in this embodiment, the present inventors demonstrated the synthesis of the novel psilocin prodrug analog intermediate compound 6. In this embodiment, to a stirred solution of compound 4 (1.0 g, 3.2 mmol, 1.0 eq) in Me-THF (anhydrous, 80 mL) under nitrogen at 0° C. to 5° C. was added LAH (1M in THF, 19.0 mL, 19.0 mmol, 6.0 eq) slowly via a syringe. The resulting yellow suspension was stirred at 70° C. for 16 hours. After cooling to 0° C. to 5° C., the reaction was quenched with water and NaOH, filtered and concentrated to provide colorless oil. To this oil in MeOH (50 mL) was added HCHO (5.0 mL), HOAc (0.70 mL) and NaCNBH3 (1.0 g) in portions. The mixture was stirred at rt for 1.5 h and concentrated to provide the residue, which was purified by chromatography (silica gel, DCM/MeOH/NH4OH=20/1/0.1) to provide compound 6 (0.50 g, 53% yield, Lot #: MNC-4R-50) as a white solid. $^1$H NMR (600 MHz, CDCl$_3$): δ 8.05 (d, J=6.0 Hz, 1H), 7.29-7.43 (m, 5H), 6.95 (s, 1H), 6.51 (m, 1H), 5.16 (s, 2H), 2.94 (m, 2H), 2.61 (m, 2H), 2.29 (s, 6H).

Synthesis of 3-(2-(dimethylamino)ethyl)-1H-pyrrolo[2,3-b]pyridin-4-ol (MY205C)

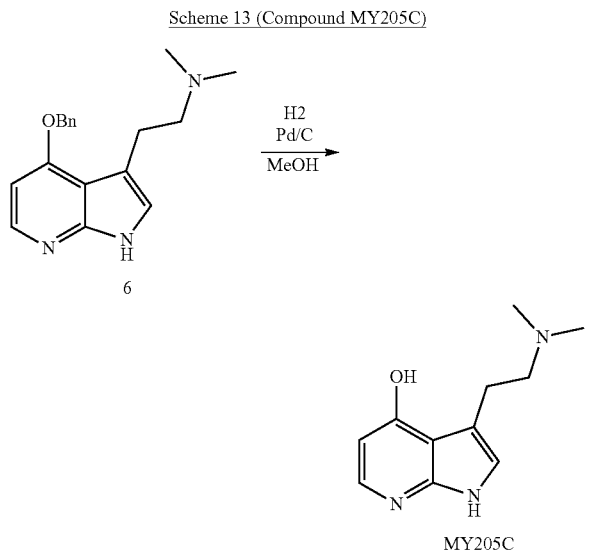

As described in Scheme 13 above, in this embodiment, the present inventors demonstrated the synthesis of the novel psilocin prodrug analog compound MY205C, also referred to herein as Formula XIX. In this embodiment, to a solution of compound 6 (0.5 g) in MeOH (30 mL) under nitrogen was added Pd/C (10% wet, 0.45 g) slowly. The mixture was hydrogenated at 1 atm for 16 h, filtered through celite pad, washed with MeOH and concentrated to provide the residue, which was purified by chromatography (silica gel, DCM/MeOH/NH4OH=20/1/0.1) to provide compound MY205C (0.086 g, 25% yield, Lot #: MNC-4R-52) as a white solid. $^1$H NMR (600 MHz, CDCl$_3$): δ 8.05 (d, J=5.4 Hz, 1H), 6.88 (s, 1H), 6.51 (d, J=5.4 Hz, 1H), 2.95 (m, 2H), 2.79 (m, 2H), 2.46 (s, 6H). $^{13}$C NMR (150 MHz, CDCl$_3$): δ 160.84, 151.25, 144.86, 119.57, 112.44, 109.80, 104.73, 61.00, 44.89, 25.10. LCMS (ES) m/z calc. for $C_{11}H_{16}N_3O$ (M+1)$^+$, 206.1; found, 206.0

Example 16: Synthesis of Novel Aza Analog 3-(2-(dimethylamino)ethyl)-1H-pyrrolo[2,3-b]pyridin-4-ol As shown in Scheme 14 below, the present invention provides for the step wise production of novel Aza analog 3-(2-(dimethylamino)ethyl)-1H-pyrrolo[2,3-c]pyridin-4-ol also referred to herein as MY205DT and Formula XX:

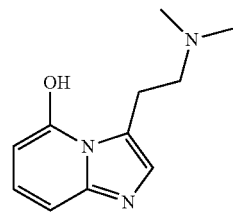

according to the following scheme.

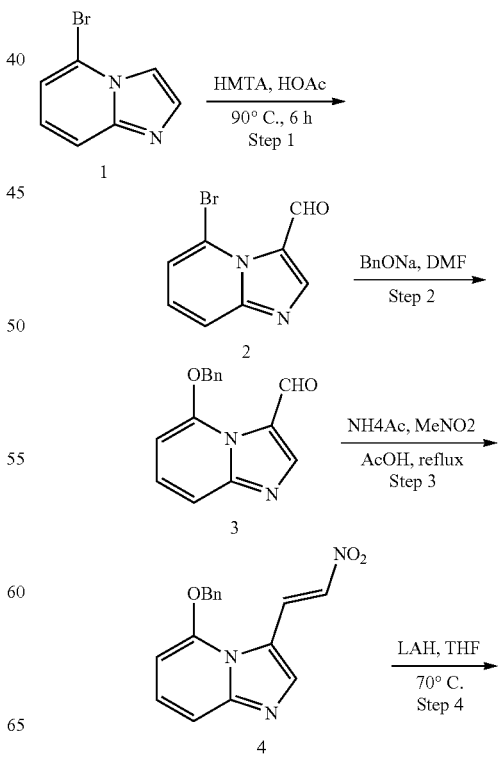

Synthesis of 5-(benzyloxy)imidazo[1,2-a]pyridine-3-carbaldehyde (3)

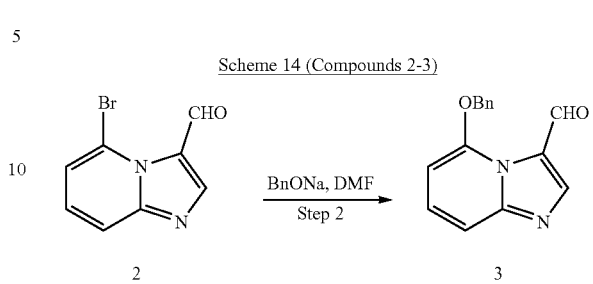

Scheme 14 (Compounds 2-3)

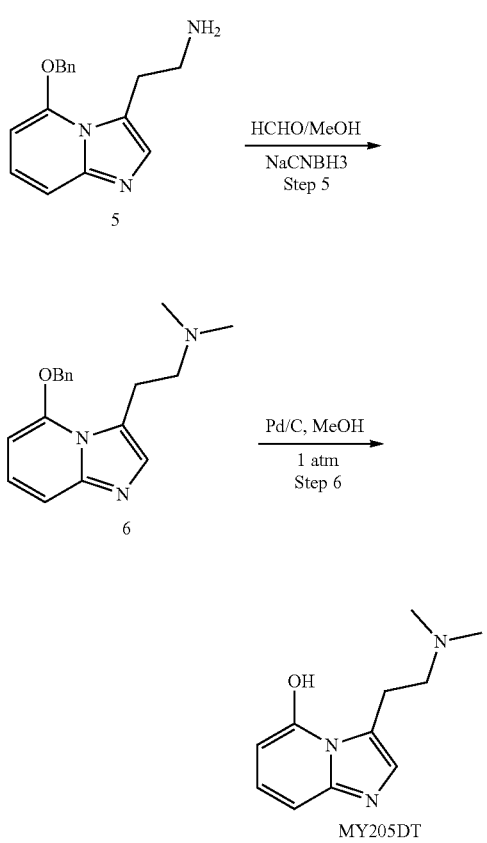

As described in Scheme 14 above, in this embodiment, the present inventors demonstrated the synthesis of the novel psilocin prodrug analog intermediate compound 3. In this embodiment, to a stirred suspension of compound 2 (2.0 g, 8.88 mmol, 1.0 eq) in DMF (17 mL) was added NaOBn in BnOH (1.4 eq). The resultant mixture was stirred and heated at 40° C. for 1 hour. The reaction mixture was quenched with water, extracted with EtOAc and concentrated under vacuum to afford the residue, which was purified by chromatography (silica gel, 1:1 Hexane:EtOAc to EtOAc) to provide compound 3 (0.45 g, 7.1% yield in 2 steps, Lot #: MNC-4R-124) as brown solid. $^1$H NMR (600 MHz, CDCl$_3$): δ 10.38 (s, 1H), 8.49 (s, 1H), 7.48 (m, 7H), 6.54 (m, 1H), 5.44 (s, 2H).

Synthesis of 5-(benzyloxy)-3-(2-nitrovinyl)imidazo[1,2-a]pyridine (4)

Scheme 14 (Compounds 3-4)

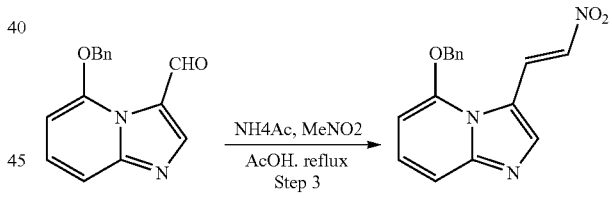

As described in Scheme 14 above, in this embodiment, the present inventors demonstrated the synthesis of the novel psilocin prodrug analog intermediate compound 4. In this embodiment, to a suspension of 3 (1.31 g, 5.2 mmol, 1.0 eq) in acetic acid (7.0 mL) was added nitromethane (1.8 mL, 36.8 mmol, 7.1 eq) followed by ammonium acetate (0.48 g, 6.2 mmol, 1.2 eq). The resultant mixture was stirred and heated at 100° C. for 2 h and TLC indicated that the reaction was complete. The reaction mixture was cooled to room temperature, quenched with water, stirred for 2h, filtered and died to afford the residue, which was purified by chromatography (silica gel short column, 20% MeOH in EtOAc) to provide compound 4 (0.57 g, 37% yield, Lot #: MNC-4R-130) as orange solid. $^1$H NMR (600 MHz, DMSO-d$_6$): 8.90 (d, J=13.2 Hz, 1H), 8.61 (s, 1H), 8.13 (d, J=13.2 Hz, 1H), 7.62 (m, 3H), 7.47 (m, 4H), 6.87 (d, J=7.2 Hz, 1H), 5.57 (s, 2H).

Synthesis of 5-bromoimidazo[1,2-a]pyridine-3-carbaldehyde (2)

Scheme 14 (Compounds 1-2)

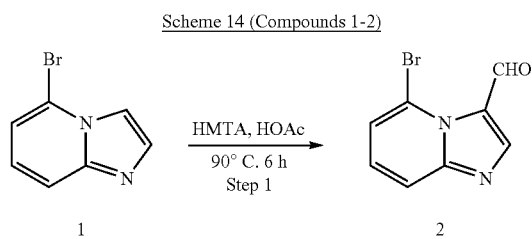 [SMILES: Brc1cccc2nccn12 ; O=Cc1cnc2cccc(Br)n12]

As described in Scheme 14 above, in this embodiment, the present inventors demonstrated the synthesis of the novel psilocin prodrug analog intermediate compound 2. In this embodiment, to a stirred suspension of 5-bromoimidazo[1,2-a]pyridine 1 (5.0 g, 25.3 mmol, 1.0 eq) in acetic acid (15 mL) was added hexamethylenetetramine (7.1 g, 50.7 mmol, 2.0 eq). The resultant mixture was stirred and heated at 90° C. for 6 hours. The reaction mixture was neutralized with NaOH to pH=7, extracted with EtOAc and concentrated under vacuum to afford the residue, which was purified by chromatography (silica gel, EtOAc) to provide compound 2 (2.2 g, 38% yield, Lot #: MNC-4R-122) as yellow solid. $^1$H NMR (600 MHz, CDCl$_3$): δ 10.87 (s, 1H), 8.45 (s, 1H), 7.75 (m, 1H), 7.03 (m, 2H).

Synthesis of 2-(5-(benzyloxy)imidazo[1,2-a]pyridin-3-yl)-N,N-dimethylethanamine (6)

Synthesis of 3-(2-(dimethylamino)ethyl)imidazo[1,2-a]pyridin-5-ol (205DT)

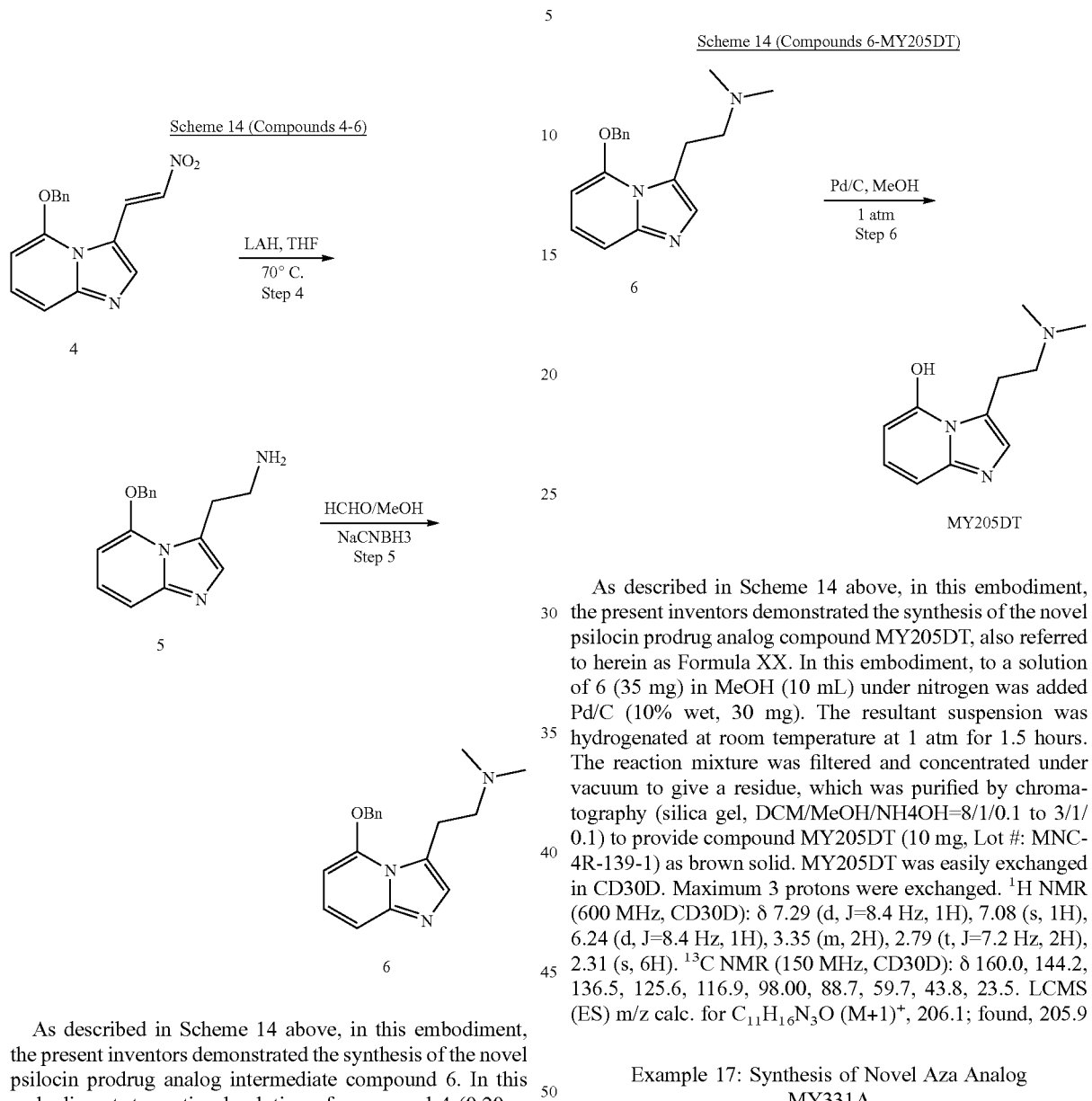

As described in Scheme 14 above, in this embodiment, the present inventors demonstrated the synthesis of the novel psilocin prodrug analog intermediate compound 6. In this embodiment, to a stirred solution of compound 4 (0.20 g, 0.68 mmol, 1.0 eq) in THF (anhydrous, 30 mL) under nitrogen at 0° C. to 5° C. was added LAH (1M in THF, 4.0 mL, 4.0 mmol, 6.0 eq) slowly via a syringe. The resulting yellow suspension was stirred at 70° C. for 1 h. After cooling to 0° C. to 5° C., the reaction was quenched with water and NaOH, filtered and concentrated to provide colorless oil. To this oil in MeOH (10 mL) was added HCHO (1.1 mL), HOAc (0.18 mL) and NaCNBH3 (0.22 g) in portions. The mixture was stirred at rt for 1.5 h and concentrated to provide the residue, which was purified by chromatography (silica gel, DCM/MeOH/NH4OH=10/1/0.1) to provide compound 6 (35 mg, Lot #: MNC-4R-136) as a yellow solid. $^1$H NMR (600 MHz, CDCl$_3$): δ 7.42 (m, 2H), 7.35 (m, 3H), 7.29 (s, 1H), 7.11 (d, J=7.2 Hz, 1H), 6.98 (t, J=7.2 Hz, 1H), 6.81 (s, 1H), 5.98 (d, J=7.2 Hz, 1H), 5.16 (s, 2H), 3.17 (t, J=7.8 Hz, 2H), 2.51 (t, J=7.8 Hz, 2H), 2.05 (s, 6H).

As described in Scheme 14 above, in this embodiment, the present inventors demonstrated the synthesis of the novel psilocin prodrug analog compound MY205DT, also referred to herein as Formula XX. In this embodiment, to a solution of 6 (35 mg) in MeOH (10 mL) under nitrogen was added Pd/C (10% wet, 30 mg). The resultant suspension was hydrogenated at room temperature at 1 atm for 1.5 hours. The reaction mixture was filtered and concentrated under vacuum to give a residue, which was purified by chromatography (silica gel, DCM/MeOH/NH4OH=8/1/0.1 to 3/1/0.1) to provide compound MY205DT (10 mg, Lot #: MNC-4R-139-1) as brown solid. MY205DT was easily exchanged in CD3OD. Maximum 3 protons were exchanged. $^1$H NMR (600 MHz, CD3OD): δ 7.29 (d, J=8.4 Hz, 1H), 7.08 (s, 1H), 6.24 (d, J=8.4 Hz, 1H), 3.35 (m, 2H), 2.79 (t, J=7.2 Hz, 2H), 2.31 (s, 6H). $^{13}$C NMR (150 MHz, CD3OD): δ 160.0, 144.2, 136.5, 125.6, 116.9, 98.00, 88.7, 59.7, 43.8, 23.5. LCMS (ES) m/z calc. for $C_{11}H_{16}N_3O$ $(M+1)^+$, 206.1; found, 205.9

Example 17: Synthesis of Novel Aza Analog MY331A

As shown in Scheme 15 below, the present invention provides for the step wise production of novel Aza analog MY331A also referred to herein and Formula XXI:

according to the following scheme:

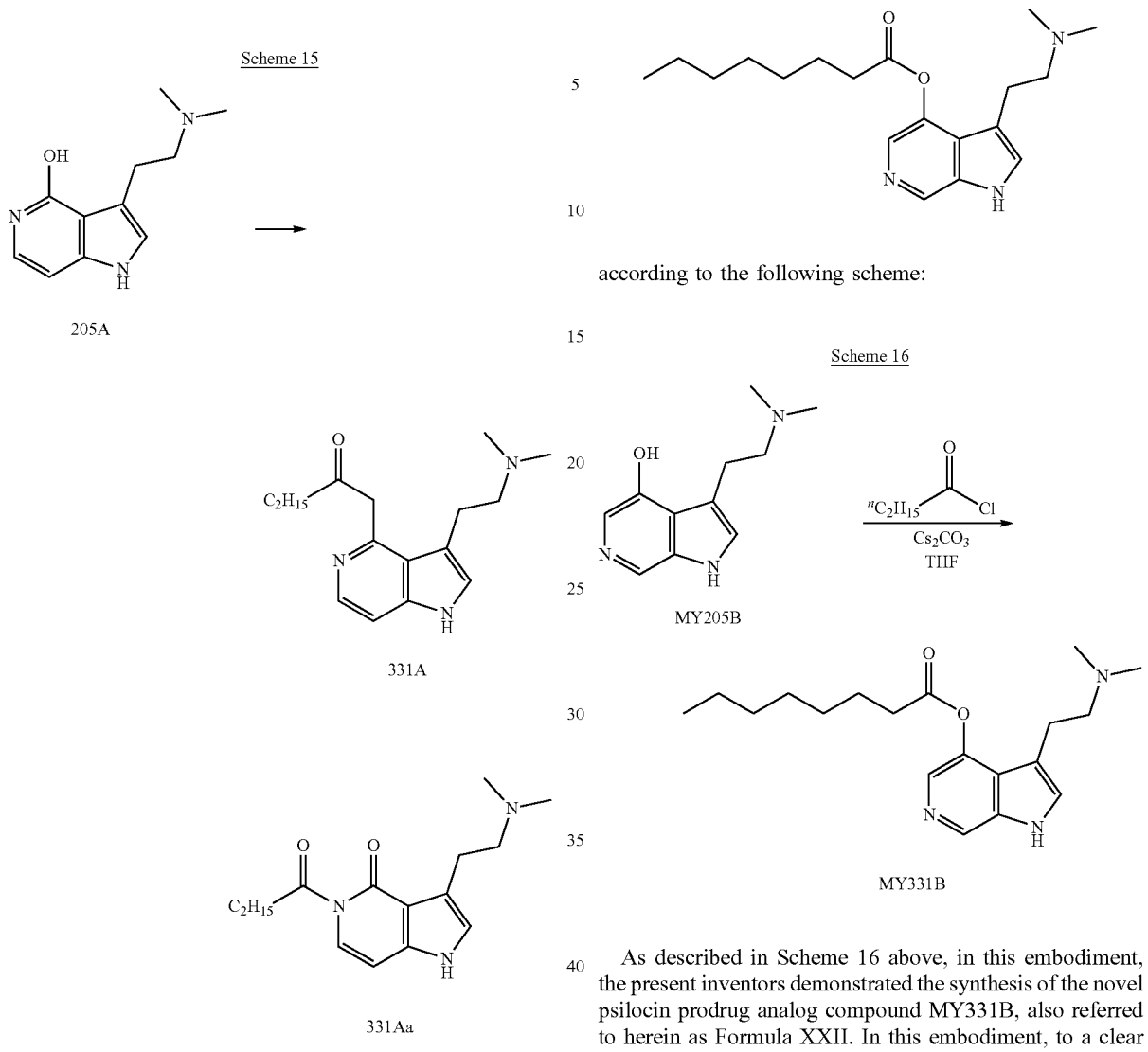

As described in Scheme 15 above, in this embodiment, the present inventors demonstrated the synthesis of the novel psilocin prodrug analog compound MY331A, also referred to herein as Formula XXI. In this embodiment, to a clear solution of 205A (0.060 g, 0.29 mmol, 1 eq) in anhydrous DCM (5 mL) at (0 to 5) ° C. under nitrogen were added n-Octanoyl chloride (0.046 g, 0.29 mmol, 1.0 eq) and trimethylamine (0.080 mL, 0.58 mmol, 2 eq) slowly via a syringe. The resultant mixture is allowed to warm to rt and concentrated under vacuum to get the crude product (oil), which was purified by chromatography (silica gel, DCM/MeOH/NH4OH=8/1/0.1) to provide compound MY331A and MY331Aa (8.4 mg, Lot #: MNC-4R-110) as oil. LCMS (ES) m/z calc. for $C_{19}H_{30}N_3O_2$ (M+1)$^+$, 332.2; found, 332.2.

Example 18: Synthesis of Novel Aza Analog 3-(2-(dimethylamino)ethyl)-1H-pyrrolo[2,3-c]pyridin-4-yl octanoate As shown in Scheme 16 below, the present invention provides for the step wise production of novel Aza analog MY331B also referred to herein and Formula XXII:

As described in Scheme 16 above, in this embodiment, the present inventors demonstrated the synthesis of the novel psilocin prodrug analog compound MY331B, also referred to herein as Formula XXII. In this embodiment, to a clear solution of MY205B (50 mg, 0.24 mmol, 1 eq) in anhydrous tetrahydrofuran (2 mL) at 0° C.~5° C. under nitrogen was added Cesium carbonate (0.124 g, 0.38 mmol, 1.5 eq) power followed by a solution of octanoyl chloride (38 mg, 0.23 mmol, 0.95 eq) in THF (3 mL) slowly via a syringe. The resultant mixture was stirred at 0° C.~5° C. for 1 h. TLC indicated that the reaction was near finished (desired product Rf 0.3; starting material MY205B Rf 0.1; Silica plate, 1% concentrated NH4OH aq/10% MeOH in DCM). The reaction mixture was filtered to remove inorganic salt. The filtrate was concentrated under vacuum to give a crude yellow solid. The crude solid was treated with TBME (1 mL), stirred at rt overnight, filtered, washed with TBME (0.5 mL), hexanes (1 mL×2), dried in air to afford the desired product 3-(2-(dimethylamino)ethyl)-1H-pyrrolo[2,3-c]pyridin-4-yl octanoate (MY331B) as pale yellow solid (32 mg, yield 40%). $^1$H NMR (600 MHz, CDCl$_3$): δ 9.00 (s, 1H), 0.7.87 (s, 1H), 7.76 (s, 1H), 2.98 (t, J=7.2 Hz, 2H), 2.69 (t, J=6.6 Hz, 2H), 2.62 (t, J=6.6 Hz, 2H), 2.27 (s, 6H), 1.67-1.70 (m, 2H), 1.24-1.38 (m, 8H), 0.88 (t, J=7.2 Hz, 3H). $^{13}$C NMR (150 MHz, CDCl$_3$): δ 171.1, 148.6, 134.7, 131.6, 129.0, 124.5, 124.0, 119.3, 60.0, 44.9, 35.4, 31.6, 29.0, 28.9, 25.0, 24.5, 22.5, 14.1 LCMS m/z=332 [M+1]$^+$

Example 19: Synthesis of Novel Aza Analog MY333B

As shown in Scheme 17 below, the present invention provides for the step wise production of novel Aza analog MY333B also referred to herein and Formula XXIII:

according to the following scheme:

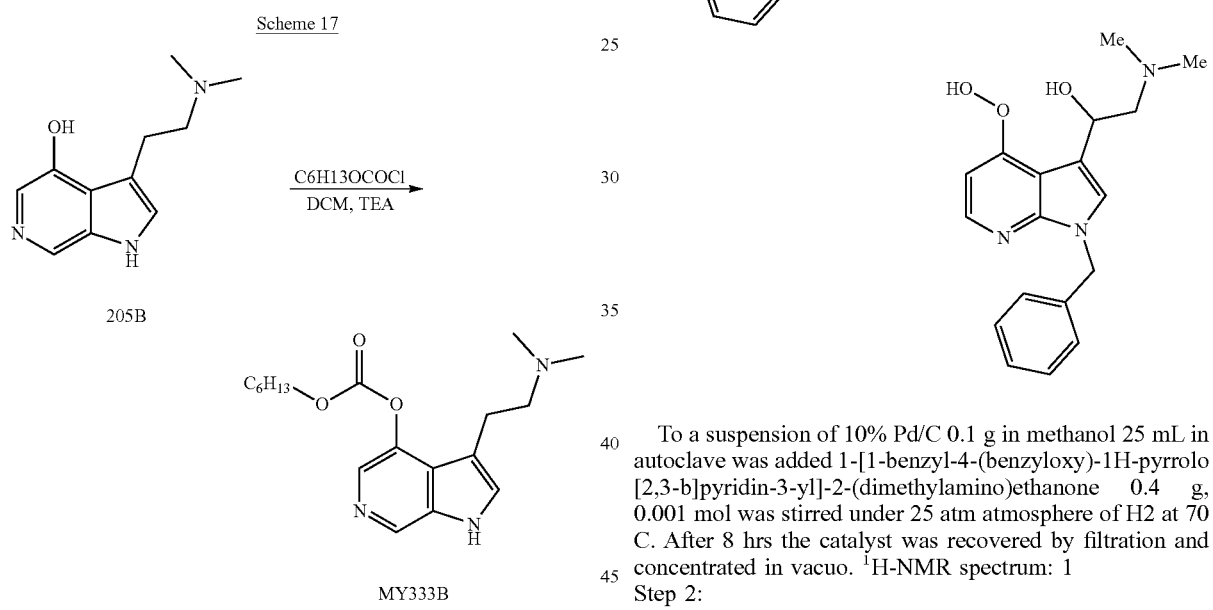

MY333B

As described in Scheme 17 above, in this embodiment, the present inventors demonstrated the synthesis of the novel psilocin prodrug analog compound MY333B, also referred to herein as Formula XXIII. In this embodiment, to a clear solution of 205B (0.060 g, 0.29 mmol, 1 eq) in anhydrous DCM (35 mL) at (0 to 5) ° C. under nitrogen were added $C_6H_{13}OCOCl$ (0.057 g, 0.35 mmol, 1.2 eq) and trimethylamine (0.080 mL, 0.58 mmol, 2 eq) slowly via a syringe. The resultant mixture is allowed to warm to rt and concentrated under vacuum to get the crude product, which was purified by chromatography (silica gel, DCM/MeOH=10/1) to provide compound MY333B (13.9 mg, Lot #: MNC-4R-107) as beige oil. $^1$H NMR (600 MHz, CDCl$_3$): δ 8.86 (s, 1H), 7.98 (s, 1H), 7.35 (s, 1H), 4.37 (t, J=6.6 Hz, 2H), 2.87 (m, 2H), 2.70 (m, 2H), 2.36 (s, 6H), 1.78 (m, 2H), 1.40 (m, 2H), 1.27 (m, 4H), 0.84 (m, 3H). LCMS (ES) m/z calc. for $C_{18}H_{28}N_3O_3$ (M+1)$^+$, 334.2; found, 334.2.

Example 20. Step-Wise Synthesis of Novel Aza Analog Intermediates

The present invention describes the step-wise synthesis of key intermediate compounds aza substituted psilocin analog.

Step 1:

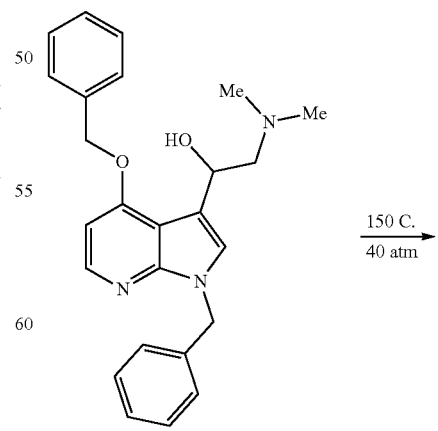

To a suspension of 10% Pd/C 0.1 g in methanol 25 mL in autoclave was added 1-[1-benzyl-4-(benzyloxy)-1H-pyrrolo[2,3-b]pyridin-3-yl]-2-(dimethylamino)ethanone 0.4 g, 0.001 mol was stirred under 25 atm atmosphere of H2 at 70 C. After 8 hrs the catalyst was recovered by filtration and concentrated in vacuo. $^1$H-NMR spectrum: 1

Step 2:

To a suspension of 10% Pd/C 0.1 g in methanol 25 mL in autoclave was added 1-[1-benzyl-4-(benzyloxy)-1H-pyrrolo

[2,3-b]pyridin-3-yl]-2-(dimethylamino)ethanone 0.4 g, 0.001 mol was stirred under 40 atm atmosphere of H2 at 150 C. After 8 hrs the catalyst was recovered by filtration and concentrated in vacuo.

Step 3:

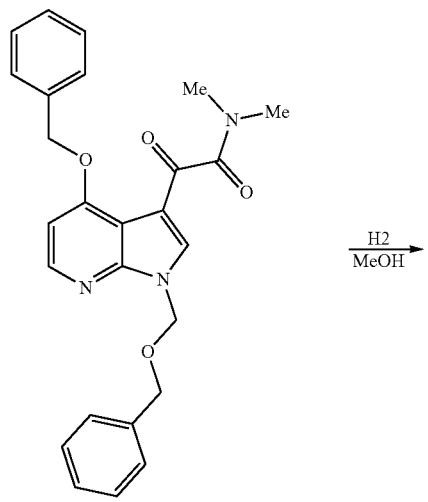

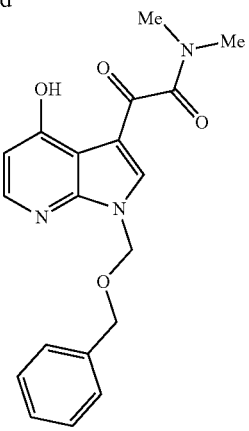

To a suspension of 10% Pd/C 0.01 g in methanol 25 mL in autoclave was added 2-[1-BOM-4-(benzyloxy)-1H-pyrrolo[2,3-b]pyridin-3-yl]-N,N-dimethyl-2-oxoacetamide 0.04 g, 0.0001 mol was stirred under atmosphere of H2 at RT. After 6 hrs the catalyst was recovered by filtration and concentrated in vacuo. 1H-NMR: 4

Step 5:

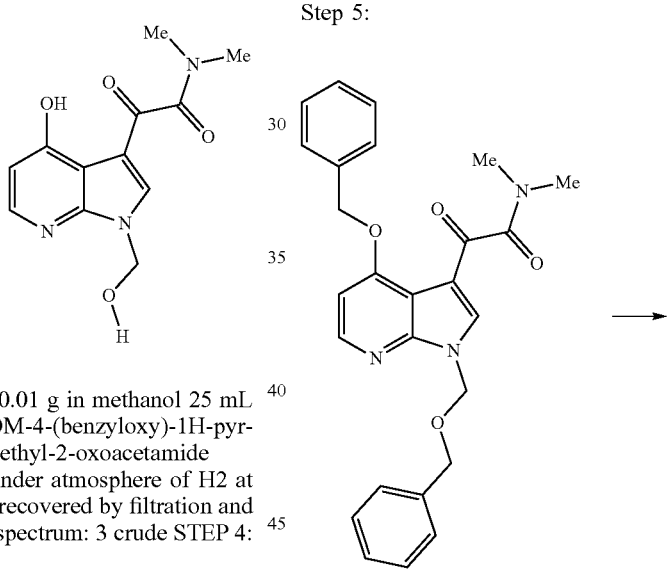

To a suspension of 10% Pd/C 0.01 g in methanol 25 mL in autoclave was added 2-[1-BOM-4-(benzyloxy)-1H-pyrrolo[2,3-b]pyridin-3-yl]-N,N-dimethyl-2-oxoacetamide 0.04 g, 0.0001 mol was stirred under atmosphere of H2 at RT. After 48 hrs the catalyst was recovered by filtration and concentrated in vacuo. ¹H-NMR spectrum: 3 crude STEP 4:

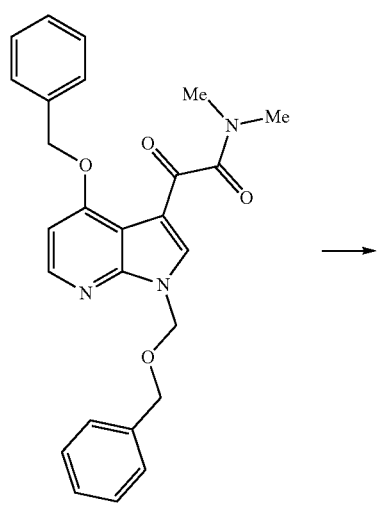

To a suspension of 10% Pd/C 0.1 g in methanol 25 mL in autoclave was added 2-[1-BOM-4-(benzyloxy)-1H-pyrrolo[2,3-b]pyridin-3-yl]-N,N-dimethyl-2-oxoacetamide 0.4 g, 0.001 mol was stirred under atmosphere of H2 at 50 C. After 6 hrs the catalyst was recovered by filtration and concentrated in vacuo. 1H-NMR: 5

Step 6:

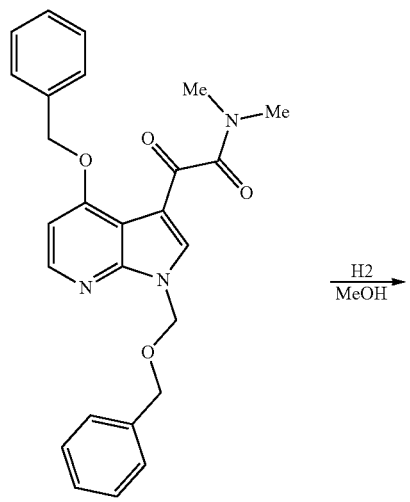

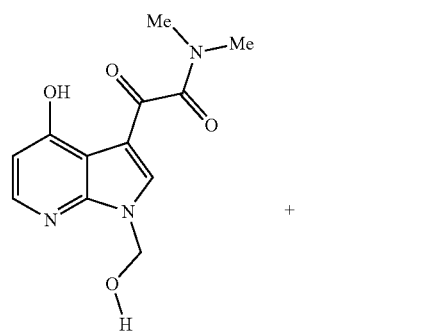

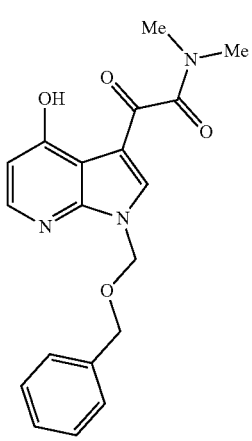

To a suspension of 10% Pd/C 0.1 g in methanol 25 mL in autoclave was added 2-[1-BOM-4-(benzyloxy)-1H-pyrrolo[2,3-b]pyridin-3-yl]-N,N-dimethyl-2-oxoacetamide 0.4 g, 0.001 mol was stirred under atmosphere of H2 at 50 C. After 12 hrs the catalyst was recovered by filtration and concentrated in vacuo. 1H-NMR: 6

Step 7:

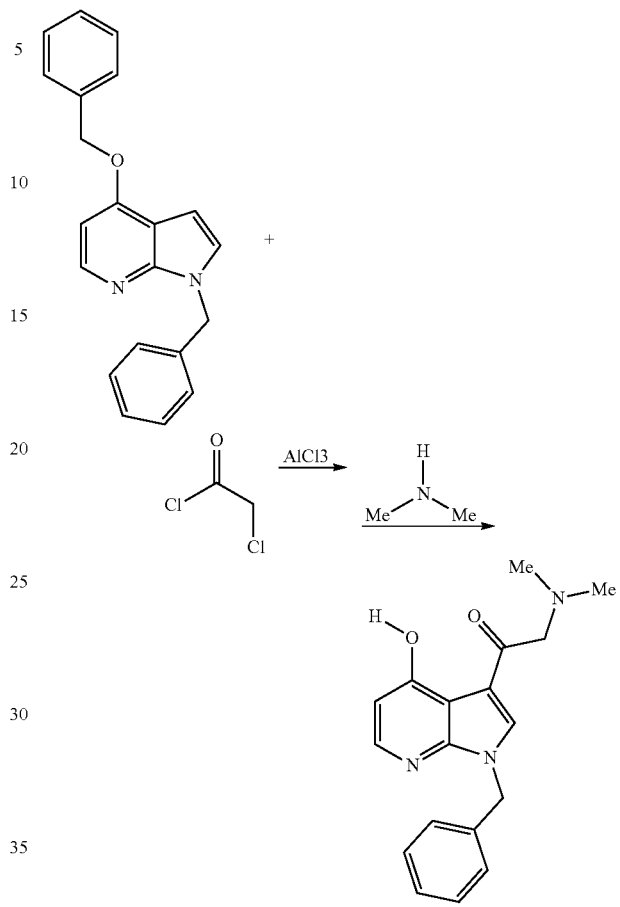

To a solution of 4-benzyl-oxo-1-((2-(benzyl)-1H-pyrrolo[2,3-b]pyridine (1.00 g, 0.003 mol) in DCE (100 mL) at RT was added aluminum chloride (2.5 g, 0.019 mol). The reaction mixture was stirred at rt for I h and then treated with chloroacetyl chloride (0.7 g, 0.006 mol) and the resulting solution was stirred at RT for 3 h. The reaction mixture concentrated in vacuo, resuspended in dioxane (15 ml) and added in cooled dimethylamine solution (40% in H2O), the reaction mixture was again evaporated. Added 100 ml EtOAc, the mixture was boiled under reflux and concentrated in vacuo.

1H-NMR: 7

Definitions

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention. The term "stereoisomer" refers to a molecule that is an enantiomer, diastereomer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

As used herein the singular forms "a", "an", and "the" include plural referents unless the context clearly dictates otherwise. Thus, for example, reference to "a compound" includes a plurality of such compounds, and reference to "the method" includes reference to one or more methods, method steps, and equivalents thereof known to those skilled in the art, and so forth. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value.

The term "compound," "active compound," or "composition," or "compound of the invention" includes all solvates, complexes, polymorphs, radiolabeled derivatives, tautomers, stereoisomers, and optical isomers of the novel psilocin analog compounds generally described herein, and salts thereof, unless otherwise specified. Notably, if the compound is anionic, or has a functional group which may be anionic (e.g., —COH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic or has a functional group which may be cationic (e.g., $NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc. It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999). For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)$CH_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—$CH_3$); a benzyloxy amide (—NHCO—$OCH_2C_6H_5$, —NH—Cbz); as a t-butoxy amide (—NHCO—OC($CH_3$)$_3$, —NH-Boc); a 2-biphenyl-2-propoxy amide (—NHCO—OC($CH_3$)$_2C_6H_4C_6H_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases, as an N-oxide (>NO). For example, a carboxylic acid group may be protected as an ester for example, as: a $C_{1-7}$ alkyl ester (e.g., a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g., a benzyl ester; a nitrobenzyl ester); or as an amide, for example, as a methyl amide. In a preferred embodiment an amine, such as (CH3)2NH (dimethylamine), or CH3CH(CH3)NHCH(CH3)CH3 (diisopropylamine) may be coupled with a an linear alkane, such as CH2CH2.

For example, a thiol group may be protected as a thioether (—SR), for example, as: a benzyl thioether; an acetamidomethyl ether (—S—$CH_2$NHC(=O)$CH_3$).

It may be convenient or desirable to prepare, purify, and/or handle the active compound in the form of a prodrug. The term "prodrug", as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required. Examples of such metabolically labile esters include, but are not limited to, those wherein R is $C_{1-20}$ alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl) carbonyloxymethyl; and 1-(4-tetrahydropyranyl) carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group O P(═O)(OH)$_2$. Such a group can be cleaved by phosphatase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate or may be an amino acid ester derivative.

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. For convenience, the IUPAC numbering of the positions of representative pyrrolopyridinyl compounds described herein are shown by the formula

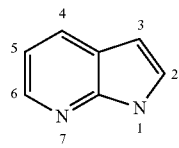

The positional numbering of pyrrolopyridinyl compounds remains the same for compounds in which the aza substitution shown at the 7-position in the above formula is moved to the 4-, 5- or 6-position of the above formula. Whenever a chiral carbon is present in a chemical structure, it is intended that all stereoisomers associated with that chiral carbon are encompassed by the structure.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-group s/substituents include alkyl groups, hydroxyl groups, alkoxy groups, acyloxy groups, mercapto groups, and aryl groups.

The term "acyl" as used herein refers to a group of the formula C(═O)-D, where the acyl may be O-linked, and where D represents an alkyl, alkenyl, alkynyl, cycloalkyl, aryl, heteroaryl, cycloalkyl, or heterocycle, among others. Also, as used herein an "O-lined" acyl may also be referred to as an "O-linked ester". Typical examples are groups wherein D is a C1-C10 alkyl, C2-C10 alkenyl or alkynyl, or phenyl, each of which is optionally substituted. In some embodiments, D can be H, Me, Et, isopropyl, propyl, butyl, C1-C4 alkyl substituted with OH, OMe, or NH$_2$, phenyl, halophenyl, alkylphenyl, and the like. As noted above, an acyl may be an N- or O-linked acyl. Additional examples are groups wherein D is a H, $C_{1-12}$ alkyl (e.g., $C_{1-8}$, $C_{1-6}$, $C_{1-4}$, $C_{2-7}$, $C_{3-12}$, or $C_{3-6}$ alkyl), $C_{2-12}$ alkenyl (e.g., $C_{2-8}$, $C_{2-6}$, $C_{2-4}$, $C_{3-12}$, or $C_{3-6}$ alkenyl), $C_{6-20}$ aryl (e.g., $C_{6-15}$, $C_{6-10}$, $C_{8-20}$, or $C_{8-15}$ aryl), monocyclic $C_{1-6}$ heteroaryl (e.g., monocyclic $C_{1-4}$ or $C_{2-6}$ heteroaryl), $C_{4-19}$ heteroaryl (e.g., $C_{4-10}$ heteroaryl), $(C_{6-15})$aryl$(C_{1-6})$alkyl, $(C_{1-6})$heteroaryl$(C_{1-6})$alkyl, or $(C_{4-19})$heteroaryl$(C_{1-6})$alkyl. As used herein, "unsaturated" means that the compound has at least one degree of unsaturation (eg, at least one multiple bond) and includes partially and fully unsaturated compounds. As used herein, "saturated" means that the compound has no degree of unsaturation (eg, at least one multiple bond) and unless stated otherwise "saturated" means "fully saturated."

The term "acyloxy," as used herein means a group-OR, where R is each independently selected from substituted alkenyl, alkynyl, aryl, aralkyl, heteroaryl, aralkyl and acyl.

The term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc. In one preferred embodiment, an "alkyl" refers to a branched or unbranched saturated hydrocarbon group of 1 to 24 carbon atoms, such as branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or (Ci-$C_6$)alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (Ci-$C_6$)alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; (Ci-$C_6$)alkanoyl can be acetyl, propanoyl or butanoyl; halo(Ci-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy(Ci-$C_6$)alkyl can be hydroxymethyl, 1-hydroxy ethyl, 2-hydroxy ethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; (Ci-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; (Ci-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

As noted above, alkyl groups can be unsubstituted, Typical substituents include, but are not limited to, halo, $=O$, $=N-CN$, $=N-OR$, $=NR^a-OR^a$, $-NR^a_2$, $SR^a$, $SO_2R^a$, $SO_2NR^a_2$, $NR^aSO_2R^a$, $-NR^aCONR^a_2$, $-NaCOOR^a$, $-NR^aCOR^a$, $CN$, $COOR^a$, $CONR^a_2$, $OOCR^a$, $COR^a$, and $NO_2$, wherein each $R^a$ is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each $R^a$ is optionally substituted with halo, $=O$, $=N-CN$, $=N-OR^b$, $=NR^bOR^b$, $R^b_2$, $SR^b$, $SO_2R^b$, $SO_2NR_2$, $NR^bSO_2R^b$, $NR^b$-$CONR^b_2$, $NR^bCOOR^b$, $NR^bCOR^b$, $CN$, $COOR^b$, $CONR^b_2$, $OOCR^b$, $COR^b$, and $NO_2$, wherein each $R^b$ is independently H, C1-C8 alkyl, C2-C8 heteroalkyl, C3-C8 heterocyclyl, C4-C10 heterocyclyclalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two $R^a$ or $R^b$ groups on the same or adjacent atoms (e.g., $-NR^b_2$, or $NR^b-C(O)R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein. Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are optionally substituted by groups suitable for alkyl groups as set forth herein.

The term "aryl" or "aromatic moiety" as used herein refers to an aromatic ring system, which may further include one or more non-carbon atoms. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic C5-C6 aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically, these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, $OR^a$, $-NR^a_2$, $SR^a$, $SO_2R^a$, $SO_2NR^a_2$, $NR^aSO_2R^a$, $NR^aCONR^a_2$, $NR^aCOOR^a$, $NR^aCOR^a$, $CN$, $COOR^a$, $CONR^a_2$, $OOCR^a$, $COR^a$, and $NO_2$, wherein each $R^a$ is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each $R^a$ is optionally substituted with halo, =O, =N—CN, =N—$OR^b$, —N—$R^b$, $OR^b$, $NR^b{}_2$, $SR^b$, $SO_2R^b$, $SO_2NR^b{}_2$, $NR^bSO_2R^b$, $NR^bCONR^b$, $NR^bCOOR^b$, $NR^bCOR^b$, CN, $COOR^b$, $CONR^b{}_2$, $OOCR^b$, $COR^b$, and $NO_2$, wherein each $R^b$ is independently H, C1-C8 alkyl, C2-C8 heteroalkyl, C3-C8 heterocyclyl, C4-C10 heterocyclyclalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two $R^a$ or $R^b$ groups on the same or adjacent atoms (e.g., $NR^b{}_2$, or $NR^b$ $C(O)R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

"Aryloxy" means a moiety of the formula OR, wherein R is an aryl moiety as defined herein.

"Arylalkyl" and "Aralkyl", which may be used interchangeably, mean a radical-RaRb where Ra is an alkylene group and Rb is an aryl group as defined herein; e.g., phenylalkyls such as benzyl, phenylethyl, 3-(3-chlorophenyl)-2-methylpentyl, and the like are examples of arylalkyl.

The term "alkoxy" as used herein refers to a hydrocarbon group connected through an oxygen atom, e.g., —O-Hc, wherein the hydrocarbon portion He may have any number of carbon atoms, typically 1-10 carbon atoms, may further include a double or triple bond and may include one or two oxygen, sulfur or nitrogen atoms in the alkyl chains, and can be substituted with aryl, heteroaryl, cycloalkyl, and/or heterocyclyl groups. For example, suitable alkoxy groups include methoxy, ethoxy, propyloxy, isopropoxy, methoxyethoxy, benzyloxy, allyloxy, and the like.

Similarly, the term "alkylthio" refers to alkylsulfides of the general formula S-Hc, wherein the hydrocarbon portion He is as described for alkoxy groups. For example, contemplated alkylthio groups include methylthio, ethylthio, isopropylthio, methoxyethylthio, benzylthio, allylthio, and the like.

The term 'amino' as used herein refers to the group —$NH_2$. The term "alkylamino" refers to amino groups where one or both hydrogen atoms are replaced by a hydrocarbon group He as described above, wherein the amino nitrogen "N" can be substituted by one or two He groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group He as described above, wherein the amino nitrogen "N" can be substituted by one or two He groups as set forth for alkoxy groups described above.

As used herein, a "heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, quinolinyl, isoquinolinyl, benzofuryl, benzofuranyl, benzothiophenyl, benzothiopyranyl, benzimidazolyl, benzoxazolyl, benzoxadiazolyl, benzothiazolyl, benzothiadiazolyl, benzopyranyl, indolyl, indazolyl, azaindolyl. pyrrolopyridine, pyrrolopyrimidine, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. "Heteroarylalkyl" and "heteroaralkyl", which may be used interchangeably, mean a radical-R'$R^b$ where $R^a$ is an alkylene group and $R^b$ is a heteroaryl group as defined herein.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aryl groups, pyridyl groups and furan groups are examples of aromatic groups. The conjugated system of an aromatic group contains a characteristic number of electrons, for example, 6 or 10 electrons that occupy the electronic orbitals making up the conjugated system, which are typically un-hybridized p-orbitals.

As used herein, "Azaindole" means a group of the formula

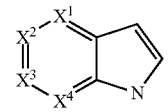

wherein one of $X^1$, $X^2$, $X^3$ and $X^4$ is N (aza), and the others are carbon. "Azaindoles" may be optionally substituted, as defined herein for heteroaryls, at position 1, 2 and 3, and at any of positions 4-through seven that are not nitrogen. "Azaindole" thus includes: "pyrrolopyridines" of the above formula wherein $X^1$ is N; "pyrrolopyridines" of the above formula wherein $X^2$ is N; "pyrrolopyridines" of the above formula wherein $X^3$ is N; and "pyrrolopyridines" of the above formula wherein $X^4$ is N;

As used herein, a "Pyrrolopyridine" may also mean a heteroaryl of the formula:

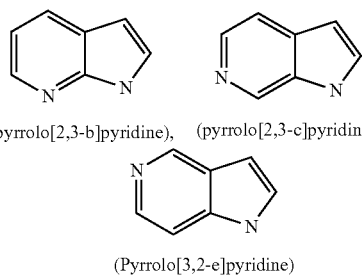

(pyrrolo[2,3-b]pyridine), (pyrrolo[2,3-c]pyridine), or (Pyrrolo[3,2-e]pyridine)

In one example, a "Pyrrolopyridine" is an "azaindole" as defined herein.

In certain embodiments, the invention includes reacting a Pyrrolopyridine or a Azaindole, and preferably a 5-5 and 6-Azaindole analogs, with an electron releasing protection group, such as a benzyl group.

As also used herein, the terms "imidazopyridine" or "imidazopyrimidine" or "thiazopyridine" or "thiazopyrimidine" herein refer to any compound in which the two designated heterocyclic rings are fused by any two adjacent atoms on the two heterocyclic rings.

The term "aryloxy" as used herein refers to an aryl group connecting to an oxygen atom, wherein the aryl group may be further substituted. For example, suitable aryloxy groups include phenyloxy, etc. Similarly, the term "arylthio" as used herein refers to an aryl group connecting to a sulfur atom, wherein the aryl group may be further substituted. For example, suitable arylthio groups include phenylthio, etc.

The hydrocarbon portion of each alkoxy, alkylthio, alkylamino, and aryloxy, etc. can be substituted as appropriate for the relevant hydrocarbon moiety.

The term "halogen" as used herein refers to fluorine, chlorine, bromine, and iodine. Where present as a substituent group, halogen or halo typically refers to F or Cl or Br, more typically F or Cl.

The term "haloalkyl" refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl and the like.

The term "haloalkoxy" refers to the group alkyl-O wherein one or more hydrogen atoms on the alkyl group have been substituted with a halo group and include, by way of examples, groups such as trifluoromethoxy, and the like.

It should further be recognized that all of the above-defined groups may further be substituted with one or more substituents, which may in turn be substituted with hydroxy, amino, cyano, C1-C4 alkyl, halo, or C1-C4 haloalkyl. For example, a hydrogen atom in an alkyl or aryl can be replaced by an amino, halo or C1-4 haloalkyl or alkyl group.

The term "substituted" as used herein refers to a replacement of a hydrogen atom of the unsubstituted group with a functional group, and particularly contemplated functional groups include nucleophilic groups (e.g., —NH$_2$, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —NH$_3^+$), and halogens (e.g., —F, —Cl), NHCOR, NHCONH$_2$, OCH$_2$COOH, OCH$_2$CONH$_2$, OCH$_2$CONHR, NHCH$_2$COOH, NHCH$_2$CONH$_2$, NHSO$_2$R, OCH$_2$-heterocycles, PO$_3$H, SO$_3$H, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties. In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

As used herein, substituted with reference to an acyl, or a "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

As used herein and unless otherwise indicated, the term "glucuronide" means a compound bearing a glycoside of glucuronic acid, having a general formula:

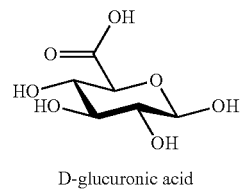

D-glucuronic acid

The term "modulation" as used herein in the context of serotonin, or other receptor binding, refers to a change in activation state as compared to the absence of a compound of the invention, or a patent compound of one or more of the compounds of the invention.

The term "beneficial" as used herein in the context of treating a condition, refers to extended relieve of symptoms (duration) and/or a more significant reduction of symptoms (magnitude).

As used herein, a "therapeutically effective amount" for treating "a disease or condition for which modulation of serotonin receptor activity is beneficial" may include, but not be limited to: for schizophrenia, a therapeutically effective amount is an amount which causes a significant reduction in psychopathology as determined by clinical improvement; for depression, a therapeutically effective amount is an amount that leads to stabilization and remission of symptoms as measured by the Patient Health Questionnaire-9; for OCD, a therapeutically effective amount is an amount that leads to stabilization and remission of symptoms as measured by the Yale-Brown Obsessive Compulsive Scale; for ADHD, a therapeutically effective amount is an amount that leads to stabilization and remission of symptoms as measured by either the ADHD Rating Scale V or ADHD Self-Report Scale; for eating disorders, a therapeutically effective amount is an amount that leads to stabilization and remission of symptoms as measured by the Eating Disorder Examination Questionnaire; for autism spectrum disorders a therapeutically effective amount is an amount that leads to stabilization and remission of symptoms as measured by physicians' assessment; for PTSD a therapeutically effective amount is an amount that leads to stabilization and remission of symptoms as measured by the Clinician-Administered PTSD Scale for DSM-5; for anxiety, a therapeutically effective amount is an amount that leads to stabilization and remission of symptoms as measured by the General Anxiety Disorder-7; for addiction, a therapeutically effective amount is an amount that leads to stabilization and remission of symptoms as measured by physicians' assessment; for cluster headaches, a therapeutically effective amount is an amount that leads to stabilization and remission of symptoms as measured by the Cluster Headache Severity Scale (CHSS); for dementia, a therapeutically effective amount is an amount that leads to stabilization and remission of symptoms as measured by the Dementia Rating Scale (DRS); for Alzheimer's disease, a therapeutically effective amount is an amount that leads to stabilization and remission of symptoms as measured by the Alzheimer's Disease Assessment Scale-Cognitive Subscale (ADAS-Cog); for paralysis, a therapeutically effective amount is an amount that leads to stabilization and remission of symptoms as measured by physicians' assessment.

The term "treatment", as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition). The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt. For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely, these salt forms can be converted into the free base form by treatment with an appropriate base. The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine, and the like.

TABLE 1

Exemplary Saturated linear esters at $R^1$

| # Carbons | Name | Structure |
|---|---|---|
| 1 | Formic | $HCO_2$ |
| 2 | Acetic | $H_3CCO_2$ |
| 3 | Propanoic | $H_3C(CH_2)CO_2$ |
| 4 | Butyric | $H_3C(CH_2)_2CO_2$ |
| 5 | Valeric | $H_3C(CH_2)_3CO_2$ |
| 6 | Caproic | $H_3C(CH_2)_4CO_2$ |
| 7 | n-Heptoic | $H_3C(CH_2)_5CO_2$ |
| 8 | Caprylic | $H_3C(CH_2)_6CO_2$ |
| 9 | Pelargonic | $H_3C(CH_2)_7CO_2$ |
| 10 | Capric | $H_3C(CH_2)_8CO_2$ |
| 11 | Undecanoic | $H_3C(CH_2)_9CO_2$ |
| 12 | Lauric | $H_3C(CH_2)_{10}CO_2$ |
| 13 | Tridecanoic | $H_3C(CH_2)_{11}CO_2$ |
| 14 | Myristic | $H_3C(CH_2)_{12}CO_2$ |
| 15 | Pentadecanoic | $H_3C(CH_2)_{13}CO_2$ |
| 16 | Palmitic | $H_3C(CH_2)_{14}CO_2$ |
| 17 | Heptadecanoic | $H_3C(CH_2)_{15}CO_2$ |
| 18 | Stearic | $H_3C(CH_2)_{16}CO_2$ |

TABLE 2

Exemplary Mono and poly-unsaturated linear fatty acid esters at $R^1$.

| # Carbon | Name | Structure |
|---|---|---|
| 12 | Cis/trans Lauroleic | $CH_3(CH_2)CH=CH(CH_2)_7CO_2$ |
| 14 | Cis/trans Myristoleic | $CH_3(CH_2)_3CH=CH(CH_2)_7CO_2$ |
| 16 | Cis/trans Palmitoleic | $CH_3(CH_2)_5CH=CH(CH_2)_7CO_2$ |
| 18 | Cis/trans alfa Linolenic | $CH_3CH_2CH=CHCH_2CH=CHCH_2CH=CH(CH_2)_7CO_2$ |
| 18 | Cis/trans gamma linolenic | $CH_3(CH_2)_4CH=CHCH_2CH=CH(CH_2)_7CO_2$ |
| 18 | Cis/trans Stearidonic | $CH_3CH_2CH=CHCH_2CH=CHCH_2CH=CHCH_2CH=CH(CH)_4CO_2$ |
| 18 | Cis/trans Oleic | $CH_3(CH_2)_6CH=CH(CH_2)_7CO_2$ |
| 18 | Cis/trans Linoleic | $CH_3(CH_2)_4CH=CHCH_2CH=CH(CH_2)_7CO_2$ |

REFERENCES

1. C Lenz et al, *Angew. Chem., Int. Ed.,* 2019, DOI: 10.1002/anie.201910175.
2. Carhart-Harris, R., Goodwin, G. The Therapeutic Potential of Psychedelic Drugs: Past, Present, and Future. Neuropsychopharmacol 42, 2105-2113 (2017).
3. D. Nutt, et al., Psychedelic Psychiatry's Brave New World. Cell 181, 24-28 (2020)

What is claimed is:

1. A psilocin analog compound comprising:

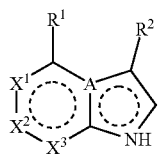

Formula (XVI)

wherein
  $X^1$ is CH;
  $X^2$ is CH;
  $X^3$ is N, or NH;
  A is C;
  $R^1$ is O, or —OH;
  $R^2$ is linear alkane-$R^3$, wherein $R^3$ is (CH3)2NH (dimethylamine); and wherein said dashed lines represents possible double bond positions according to the configuration of X being N or CH, and $R^1$ being O or —OH; or
  a pharmaceutically acceptable salt thereof.

2. The compound of claim 1, wherein said compound is selected from:

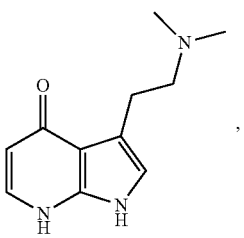

(Formula XIX)

(Formula XIII)

-continued a pharmaceutically acceptable salt thereof.

3. The compound of claim 1, further comprising at least one pharmaceutically acceptable carrier, forming a pharmaceutical composition.

4. The compound of claim 2, further comprising at least one pharmaceutically acceptable carrier, forming a pharmaceutical composition.

5. A psilocin analog compound comprising:

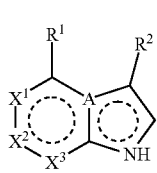

Formula (XVI)

wherein
X¹ is CH;
X is CH;
X³ is N, or NH;
A is C;
R¹ is O, or —OH;
R² is linear alkane-R³, wherein R³ is (CH3CH(CH3)NHCH(CH3)CH3 (diisopropylamine);
and wherein said dashed lines represents possible double bond positions according to the configuration of X being N or CH, and R¹ being O or —OH; or
a pharmaceutically acceptable salt thereof.

6. The compound of claim 5, further comprising at least one pharmaceutically acceptable carrier, forming a pharmaceutical composition.

* * * * *